US011835522B2

(12) United States Patent
Bhatia et al.

(10) Patent No.: US 11,835,522 B2
(45) Date of Patent: Dec. 5, 2023

(54) SENSORS FOR DETECTING AND IMAGING OF CANCER METASTASIS

(71) Applicant: Massachusetts Institute of Technology, Cambridge, MA (US)

(72) Inventors: Sangeeta N. Bhatia, Lexington, MA (US); Liangliang Hao, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 11 days.

(21) Appl. No.: 16/745,748

(22) Filed: Jan. 17, 2020

(65) Prior Publication Data

US 2020/0232986 A1 Jul. 23, 2020

Related U.S. Application Data

(60) Provisional application No. 62/793,805, filed on Jan. 17, 2019.

(51) Int. Cl.
| | | |
|---|---|---|
| *G01N 33/573* | (2006.01) | |
| *G01N 33/534* | (2006.01) | |
| *G01N 33/574* | (2006.01) | |

(52) U.S. Cl.
CPC ......... *G01N 33/573* (2013.01); *G01N 33/534* (2013.01); *G01N 33/574* (2013.01)

(58) Field of Classification Search
None
See application file for complete search history.

(56) References Cited

U.S. PATENT DOCUMENTS

| | | | |
|---|---|---|---|
| 5,500,161 A | 3/1996 | Andrianov et al. | |
| 5,811,252 A | 9/1998 | Verheijen | |
| 5,885,775 A | 3/1999 | Haff et al. | |
| 6,312,390 B1 | 11/2001 | Phillips | |
| 6,335,429 B1 | 1/2002 | Cai et al. | |
| 6,339,069 B1 | 1/2002 | Meers et al. | |
| 6,592,847 B1 | 7/2003 | Weissleder et al. | |
| 6,597,996 B1 | 7/2003 | Venkataraman et al. | |
| 6,629,040 B1 | 9/2003 | Goodlett et al. | |
| 6,824,981 B2 | 11/2004 | Chait et al. | |
| 7,041,453 B2 | 5/2006 | Yang | |
| 7,045,296 B2 | 5/2006 | Parker et al. | |
| 7,169,892 B2 | 1/2007 | Atsushi et al. | |
| 7,179,655 B2 | 2/2007 | Patricelli | |
| 7,329,506 B2 | 2/2008 | William | |
| 7,412,332 B1 | 8/2008 | Venkataraman et al. | |
| 7,456,269 B2 | 11/2008 | Gurney et al. | |
| 7,468,258 B2 | 12/2008 | Owen | |
| 7,544,518 B2 | 6/2009 | Aebersold et al. | |
| 7,595,155 B2 | 9/2009 | Murakami | |
| 7,820,108 B2 | 10/2010 | Lampotang et al. | |
| 7,879,574 B2 | 2/2011 | Packard et al. | |
| 7,985,401 B2 | 7/2011 | Jiang et al. | |
| 8,673,267 B2 | 3/2014 | Bhatia et al. | |
| 8,841,085 B2 | 9/2014 | Kwon et al. | |
| 8,969,027 B2 | 3/2015 | Bossmann et al. | |
| 9,006,415 B2 | 4/2015 | Ren et al. | |
| 9,072,792 B2 | 7/2015 | Jiang et al. | |
| 9,155,471 B2 | 10/2015 | Lee et al. | |
| 9,416,195 B2 | 8/2016 | Sagi et al. | |
| 9,657,326 B2 | 5/2017 | Ruether et al. | |
| 9,808,532 B2 | 11/2017 | Tsien et al. | |
| 9,913,917 B2 * | 3/2018 | Groves | A61K 49/0093 |
| 9,970,941 B2 | 5/2018 | Bhatia et al. | |
| 10,006,916 B2 | 6/2018 | Kwong et al. | |
| 10,253,365 B1 | 4/2019 | Doudna et al. | |
| 10,527,619 B2 | 1/2020 | Bhatia et al. | |
| 10,702,474 B2 | 7/2020 | Sailor et al. | |
| 10,883,998 B2 | 1/2021 | Bhatia et al. | |
| 11,054,428 B2 | 7/2021 | Bhatia et al. | |
| 11,428,689 B2 | 8/2022 | Bhatia et al. | |
| 11,448,643 B2 | 9/2022 | Bhatia et al. | |

(Continued)

FOREIGN PATENT DOCUMENTS

| | | |
|---|---|---|
| AU | 2005227364 A1 | 11/2005 |
| CN | 102558362 A | 7/2012 |

(Continued)

OTHER PUBLICATIONS

EMBOSS—SeqAlign (EMBOSS Needle Sequence Alignment, 2021). (Year: 2021).*
Amidase (Amidase, Protein Classification, InterPro Webpage, 2021 (Year: 2021).*
Garcia-Echeverria, C., et al. "A new Antennapedia-derived vector for intracellular delivery of exogenous compounds." Bioorganic & medicinal chemistry letters 11.11 (2001): 1363-1366. (Year: 2001).*
Pasut, G., & Veronese, F. M. (2009). PEG conjugates in clinical development or use as anticancer agents: an overview. Advanced drug delivery reviews, 61(13), 1177-1188. (Year: 2009).*
International Search Report and Written Opinion for PCT/US2020/014007 dated Jun. 3, 2020.
[No Author Listed] Summary for peptidase S01.010: granzyme B. Merops. Retrieved from <https://www.ebi.ac.uk/merops/cgi-bin/pepsum?id=S01.010;type=P>. Apr. 26, 2019. 2 pages.

(Continued)

*Primary Examiner* — Robert J Yamasaki
*Assistant Examiner* — Trevor Kane
(74) *Attorney, Agent, or Firm* — Wolf, Greenfield & Sacks, P.C.

(57) ABSTRACT

In some aspects, the disclosure relates to compositions and method for detection, classification, and treatment of cancer. In some embodiments, the disclosure relates to protease imaging sensors comprising a scaffold linked to an enzyme-specific substrate that includes a first detectable marker capable of being released from the prostate protease sensor when exposed to an enzyme present in cancer and a tumor imaging agent comprising a second detectable marker that is linked to the scaffold. In some embodiments, the disclosure relates to methods of monitor progression of a tumor in a subject based upon detection of detectable markers in a sample obtained from a subject who has been administered a protease imaging sensor, upon detection of a tumor imaging agent, or any combination thereof.

19 Claims, 18 Drawing Sheets

Specification includes a Sequence Listing.

(56) References Cited

U.S. PATENT DOCUMENTS

| | | |
|---|---|---|
| 11,519,905 B2 | 12/2022 | Bhatia et al. |
| 11,549,947 B2 | 1/2023 | Bhatia et al. |
| 11,549,951 B2 | 1/2023 | Bhatia et al. |
| 2002/0119490 A1 | 8/2002 | Aebersold et al. |
| 2003/0059952 A1 | 3/2003 | Chait et al. |
| 2004/0014652 A1 | 1/2004 | Dubois et al. |
| 2004/0091943 A1 | 5/2004 | Schneider |
| 2005/0107583 A1 | 5/2005 | Jiang et al. |
| 2005/0260695 A1 | 11/2005 | Fleming et al. |
| 2006/0008856 A1 | 1/2006 | Singh et al. |
| 2006/0257883 A1 | 11/2006 | Bjoraker et al. |
| 2006/0292631 A1 | 12/2006 | Broberg et al. |
| 2007/0010433 A1 | 1/2007 | Albrechtsen et al. |
| 2007/0048752 A1 | 3/2007 | Yan et al. |
| 2007/0207555 A1 | 9/2007 | Guerra et al. |
| 2007/0258894 A1 | 11/2007 | Melker et al. |
| 2008/0026480 A1 | 1/2008 | Guerra |
| 2008/0064607 A1 | 3/2008 | Yang |
| 2008/0095758 A1 | 4/2008 | Lee et al. |
| 2008/0113875 A1 | 5/2008 | Chaurand et al. |
| 2008/0213377 A1 | 9/2008 | Bhatia et al. |
| 2008/0226562 A1 | 9/2008 | Groves et al. |
| 2008/0241955 A1 | 10/2008 | Purkayastha et al. |
| 2008/0253960 A1* | 10/2008 | Zheng ............... A61K 47/6929 424/9.4 |
| 2009/0016988 A1 | 1/2009 | Buckley |
| 2009/0088332 A1 | 4/2009 | Ju et al. |
| 2009/0156424 A1 | 6/2009 | Thompson |
| 2009/0230300 A1 | 9/2009 | Trevejo et al. |
| 2009/0246142 A1 | 10/2009 | Bhatia et al. |
| 2009/0252677 A1* | 10/2009 | Bogyo ................... A61P 35/00 424/9.1 |
| 2010/0022408 A1 | 1/2010 | Singh et al. |
| 2010/0124757 A1 | 5/2010 | Kwon et al. |
| 2010/0190193 A1 | 7/2010 | Calatzis et al. |
| 2010/0240050 A1 | 9/2010 | Bhatia et al. |
| 2010/0317542 A1 | 12/2010 | Lim et al. |
| 2011/0014125 A1 | 1/2011 | Bossmann et al. |
| 2011/0021908 A1 | 1/2011 | Lee et al. |
| 2011/0104052 A1* | 5/2011 | Barnett ................ A61K 9/1635 424/1.25 |
| 2011/0104071 A1 | 5/2011 | Lee et al. |
| 2011/0277538 A1 | 11/2011 | Haick |
| 2012/0039990 A1* | 2/2012 | Reshetnyak ......... A61K 31/711 514/44 R |
| 2012/0150164 A1 | 6/2012 | Lee et al. |
| 2012/0183949 A1 | 7/2012 | Hyde et al. |
| 2013/0078188 A1 | 3/2013 | Tsein et al. |
| 2013/0295129 A1 | 11/2013 | Irvine et al. |
| 2013/0315906 A1 | 11/2013 | Lowman et al. |
| 2014/0207129 A1 | 7/2014 | Lee |
| 2014/0234431 A1 | 8/2014 | Bhatia et al. |
| 2014/0255313 A1 | 9/2014 | Vasiljeva et al. |
| 2014/0276102 A1 | 9/2014 | Lee et al. |
| 2014/0276103 A1 | 9/2014 | Lee et al. |
| 2014/0301950 A1 | 10/2014 | Lee et al. |
| 2014/0303014 A1 | 10/2014 | Kwong et al. |
| 2014/0363833 A1* | 12/2014 | Bhatia ............ G01N 33/54306 435/7.92 |
| 2014/0364368 A1 | 12/2014 | Lin et al. |
| 2015/0051153 A1* | 2/2015 | Reshetnyak ........... A61K 51/08 514/19.2 |
| 2015/0080721 A1 | 3/2015 | Novak et al. |
| 2015/0104381 A1* | 4/2015 | Maina-Nock ........ A61P 35/00 424/1.45 |
| 2015/0165062 A1 | 6/2015 | Liao et al. |
| 2015/0344523 A1 | 12/2015 | Deyle et al. |
| 2016/0025632 A1 | 1/2016 | Lee et al. |
| 2016/0096869 A1 | 4/2016 | Hansen et al. |
| 2016/0184459 A1* | 6/2016 | Ueki ................ A61K 49/0004 536/27.22 |
| 2016/0289324 A1 | 10/2016 | Moore et al. |
| 2016/0317037 A1 | 11/2016 | Lee et al. |
| 2017/0267727 A1* | 9/2017 | Thevenin ............... C07K 14/00 |
| 2017/0305968 A1 | 10/2017 | Tsein et al. |
| 2018/0021090 A1 | 1/2018 | Lee et al. |
| 2018/0196058 A1 | 7/2018 | Kwong et al. |
| 2018/0328941 A1 | 11/2018 | Bhatia et al. |
| 2018/0335429 A1 | 11/2018 | Bhatia et al. |
| 2019/0076081 A1 | 3/2019 | Hyde et al. |
| 2019/0128873 A1 | 5/2019 | Bhatia et al. |
| 2019/0144917 A1 | 5/2019 | Bhatia et al. |
| 2019/0212291 A1 | 7/2019 | Dudani et al. |
| 2019/0271704 A1 | 9/2019 | Bhatia et al. |
| 2019/0345534 A1 | 11/2019 | Kwong et al. |
| 2019/0376113 A1 | 12/2019 | Kwong et al. |
| 2020/0096514 A1 | 3/2020 | Bhatia et al. |
| 2020/0116725 A1 | 4/2020 | Bhatia et al. |
| 2020/0225231 A1 | 7/2020 | Bhatia et al. |
| 2020/0249194 A9 | 8/2020 | Dudani et al. |
| 2021/0148926 A1 | 5/2021 | Bhatia et al. |
| 2021/0262025 A1 | 8/2021 | Bhatia et al. |
| 2022/0128571 A1 | 4/2022 | Bhatia et al. |
| 2023/0194544 A1 | 6/2023 | Bhatia et al. |

FOREIGN PATENT DOCUMENTS

| | | | |
|---|---|---|---|
| CN | 103012595 A | 4/2013 | |
| CN | 108484847 A | 9/2018 | |
| EP | 1808188 A1 | 7/2007 | |
| JP | 2004-506900 | 3/2004 | |
| JP | 2004-129651 | 4/2004 | |
| JP | 2004-533610 A | 11/2004 | |
| JP | 2005-315688 A | 11/2005 | |
| JP | 2007-024631 A2 | 2/2007 | |
| JP | 2007-206054 A | 8/2007 | |
| JP | 2009-108037 | 5/2009 | |
| JP | 2009-524688 | 7/2009 | |
| JP | 2009-538430 A | 11/2009 | |
| JP | 2013-060452 | 4/2013 | |
| JP | 2016-520327 | 7/2016 | |
| WO | WO 2002/014867 A2 | 2/2002 | |
| WO | WO 2006/034370 A2 | 3/2006 | |
| WO | WO 2006/067221 A2 | 6/2006 | |
| WO | WO 2007/060921 A1 | 5/2007 | |
| WO | WO 2007/063300 A2 | 6/2007 | |
| WO | WO 2007/072070 A1 | 6/2007 | |
| WO | WO 2008/072676 A1 | 6/2008 | |
| WO | WO 2008/093513 A1 | 8/2008 | |
| WO | WO 2008/127019 A1 | 10/2008 | |
| WO | WO 2009/124265 A1 | 10/2009 | |
| WO | WO 2010/101628 A2 | 9/2010 | |
| WO | WO 2011/008996 A2 | 1/2011 | |
| WO | WO 2012/031250 A2 | 3/2012 | |
| WO | WO-2012047354 A2 * | 4/2012 | ........... A61K 33/242 |
| WO | WO 2012/085080 A1 | 6/2012 | |
| WO | WO 2012/125808 A1 | 9/2012 | |
| WO | WO 2013/019681 A2 | 2/2013 | |
| WO | WO 2014/107599 A2 | 7/2014 | |
| WO | WO 2014/120619 A2 | 8/2014 | |
| WO | WO 2014/120974 A1 | 8/2014 | |
| WO | WO 2014/176284 A1 | 10/2014 | |
| WO | WO 2014/197816 A1 | 12/2014 | |
| WO | WO 2014/197840 A1 | 12/2014 | |
| WO | WO 2015/042202 A1 | 3/2015 | |
| WO | WO 2017/044894 A2 | 3/2017 | |
| WO | WO 2017/120410 A1 | 7/2017 | |
| WO | WO 2017/177115 A1 | 10/2017 | |
| WO | WO 2017/180789 A2 | 10/2017 | |
| WO | WO 2017/181149 A1 | 10/2017 | |
| WO | WO 2017/193070 A1 | 11/2017 | |
| WO | WO 2018/049285 A1 | 3/2018 | |
| WO | WO 2018/064383 A1 | 4/2018 | |
| WO | WO 2018/187688 A1 | 10/2018 | |
| WO | WO 2018/227132 A1 | 12/2018 | |
| WO | WO 2019/071051 A1 | 4/2019 | |
| WO | WO 2019/075292 A1 | 4/2019 | |
| WO | WO 2019/089804 A1 | 5/2019 | |
| WO | WO 2019/089820 A1 | 5/2019 | |
| WO | WO 2019/126577 A2 | 6/2019 | |
| WO | WO 2019/126716 A1 | 6/2019 | |
| WO | WO 2019/126762 A2 | 6/2019 | |
| WO | WO 2019/148206 A1 | 8/2019 | |

(56) References Cited

FOREIGN PATENT DOCUMENTS

| WO | WO 2019/173332 A1 | 9/2019 |
|---|---|---|
| WO | WO 2020/068920 A1 | 4/2020 |
| WO | WO 2020/081635 A1 | 4/2020 |
| WO | WO 2020/150560 A1 | 7/2020 |

OTHER PUBLICATIONS

[No Author Listed] Summary for peptidase S01.135: granzyme A. Merops. Retrieved from <https://www.ebi.ac.uk/merops/cgi-bin/pepsum?id=S01.135;type=P>. Apr. 26, 2019. 2 pages.

[No Author Listed] Summary for peptidase S01.146: granzyme K. Merops. Retrieved from <https://www.ebi.ac.uk/merops/cgi-bin/pepsum?id=S01.146;type=P>. Apr. 26, 2019. 2 pages.

[No Author Listed], DQ™ Gelatin From Pig Skin, Fluorescein Conjugate—Special Packaging. ThermoFisher Scientific. ENZCHEK® Gelatinase/Collagenase Assay Kit Product Information Sheet. Accessed on Jul. 14, 2020. Retrieved from: <https://www.thermofisher.com/order/catalog/product/D12054#/D12054>. 4 pages.

Aalipour et al., Engineered immune cells as highly sensitive cancer diagnostics. Nat Biotechnol. 2019;37:531-9.

Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.

Abudayyeh, Nanoparticle-Chaperoned Urinary "Synthetic Biomarkers" for Profiling Proteases in Cancer. Thesis. Department of Mechanical Engineering. Jun. 2012.

Acharige et al., Breath-based diagnosis of fungal infections. J Breath Res. Feb. 6, 2018;12(2):027108. doi: 10.1088/1752-7163/aa98a1.

Adiguzel et al., Breath sensors for lung cancer diagnosis. Biosens Bioelectron. Mar. 15, 2015;65:121-38. doi: 10.1016/j.bios.2014.10.023. Epub Oct. 19, 2014.

Amstad et al., Photo- and thermoresponsive polymersomes for triggered release. Angew Chem Int Ed. 2012;51:1-6.

Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.

Asai et al., A colorimetric assay for plasma antithrombin III using a new synthetic peptide substrate (PS-915). Clin Chim Acta. Dec. 29, 1984;144(2-3):163-71.

Bartlett, Diagnostic tests for agents of community-acquired pneumonia. Clin Infect Dis. May 2011;52 Suppl 4:S296-304. doi: 10.1093/cid/cir045.

Baruch et al., Enzyme activity—it's all about image. Trends Cell Biol. Jan. 2004;14(1):29-35.

Bascomb et al., Use of Enzyme Tests in Characterization and Identification of Aerobic and Facultatively Anaerobic Gram-Positive Cocci. Clin Microbiol Rev. Apr. 1998; 11(2): 318-340.

Beauchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.

Becker et al., Thrombin: Structure, Biochemistry, Measurement, and Status in Clinical Medicine. J Thromb Thrombolysis. Jul. 1998;5(3):215-229

Berger, Helicobacter pylori breath tests. BMJ. 2002;324:1263.

Blum et al., Noninvasive optical imaging of cysteine protease activity using fluorescently quenched activity-based probes. Nat Chem Biol. Oct. 2007;3(10):668-77. Epub Sep. 9, 2007.

Bohm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.

Bonomi et al., Detection of enzyme activity through catalytic signal amplification with functionalized gold nanoparticles. Angew Chem Int Ed. 2011;50:2307-12.

Bounameaux et al., Plasma measurement of D-dimer as diagnostic aid in suspected venous thromboembolism: an overview. Thromb Haemost. Jan. 1994;71(1):1-6.

Buss et al., Protease activity sensors noninvasively classify bacterial infections and antibiotic responses. EBioMedicine. Dec. 2018;38:248-56. doi:10.1016/j.ebiom.2018.11.031.

Caliendo et al., Better Tests, Better Care: Improved Diagnostics for Infectious Diseases. Clin Infect Dis. Dec. 2013;57(3):S139-S170.

Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.

Chan et al., Engineering synthetic breath biomarkers for respiratory disease. Nature Nanotechnol. Jul. 20, 2020;15:792-800.

Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.

Chen et al., A unique substrate recognition profile for matrix metalloproteinase-2. J Biol Chem. Feb. 8, 2002;277(6):4485-91.

Chen et al., CRISPR-Cas12a target binding unleashes indiscriminate single-stranded DNase activity. Science. Apr. 27, 2018;360(6387):436-439. doi: 10.1126/science.aar6245. Epub Feb. 15, 2018. Erratum in: Science. Feb. 19, 2021;371(6531).

Cheng et al., Multifunctional nanoparticles: Cost versus benefit of adding targeting and imaging capabilities. Sci. Nov. 16, 2012;338(6109):903-10.

Cheng et al., Ultrasensitive scanometric strategy for detection of matrix metalloproteinases using a histidine tagged peptide—Au nanoparticle probe. Chem Commun. 2011;47:2877-9.

Coelho et al., Usefulness of C-reactive protein in monitoring the severe community-acquired pneumonia clinical course. Crit Care. Aug. 2007; 11(4):R92.

Cohen et al., Detection and localization of surgically resectable cancers with a multi-analyte blood test. Science. 2018;3247(80):1-10.

Daniel et al., Implantable diagnostic device for cancer monitoring. Biosens Bioelectron. Jul. 15, 2009;24(11):3252-7. Epub Apr. 16, 2009.

Danino et al., Programmable probiotics for detection of cancer in urine. Sci Transl Med. May 27, 2015;7(289):289ra84. doi: 10.1126/scitranslmed.aaa3519. PMID: 26019220; PMCID: PMC4511399.

De la Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.

Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.

Dennis et al., Albumin binding as a general strategy for improving the pharmacokinetics ofproteins. J Biol Chem. Sep. 20, 2002;277(38):35035-43. Epub Jul. 15, 2002.

Deshpande et al., Current trends in the use of liposomes for tumor targeting. Nanomedicine (Lond). Sep. 2013;8(9):1509-28. doi: 10.2217/nnm.13.118.

Dranoff, Cytokines in cancer pathogenesis and cancer therapy. Nat Rev Cancer. Jan. 2004;4(1):11-22.

D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.

Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.

Dudani et al., Harnessing Protease Activity to Improve Cancer Care. Ann Rev Cancer Biol. Mar. 2018;2:353-376.

Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.

Dudani et al., Sustained-release synthetic biomarkers for monitoring thrombosis and inflammation using point-of-care compatible

(56) References Cited

OTHER PUBLICATIONS readouts. Adv Funct Mater. May 3, 2016;26(17):2919-2928. doi: 10.1002/adfm.201505142. Epub Mar. 22, 2016.

El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.

Elegbede et al., Mechanistic studies of the triggered release of liposomal contents by matrix metalloproteinase-9. J Am Chem Soc. Aug. 1, 20083;130(32):10633-42. doi: 10.1021/ja801548g. Epub Jul. 2, 20082.

Elston et al., New continuous and specific fluorometric assays for Pseudomonas aeruginosa elastase and LasA protease. Anal Biochem. Sep. 2007;368(1):87-94.

Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.

Farwell et al., PET/CT imaging in cancer: current applications and future directions. Cancer. Nov. 15, 2014;120(22):3433-45. doi: 10.1002/cncr.28860. Epub Jun. 19, 2014. PMID: 24947987.

Fernandez et al., Volatile Biomarkers in Breath Associated With Liver Cirrhosis—Comparisons of Pre- and Post-liver Transplant Breath Samples. EBIOM. 2015;2:1243-50.

Figueiredo et al., Folic acid and prevention of colorectal adenomas: a combined analysis of randomized clinical trials. Int J Cancer. Jul. 1, 2011;129(1):192-203. doi: 10.1002/ijc.25872. Epub Apr. 1, 2011.

Figueiredo et al., Near infrared thoracoscopy of tumoral protease activity for improved detection of peripheral lung cancer. Int J Cancer. Jun. 2006;118(11):2672-7. doi:10.1002/ijc.21713.

Fowlkes et al., Proteolysis of insulin-like growth factor binding protein-3 during rat pregnancy: a role for matrix metalloproteinases. Endocrinology. Dec. 1994; 135(6):2810-3.

Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.

Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.

Galati et al., Increased resistance of peptides to serum proteases by modification of their amino groups. Resist peptides against serum proteases. Jan. 8, 2003:58:558-61.

Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015; 12(1). doi:10.1038/nrclinonc.2014.70.

Genbank Submission; NIH/NCBI, Accession No. 2WV1_A; Kovalevskiy et al.; Mar. 24, 2010.

Genbank Submission; NIH/NCBI, Accession No. CAG01641; Mar. 17, 2004.

Genbank Submission; NIH/NCBI, Accession No. NP_731669; Hoskins et al.; Dec. 18, 2009.

Genbank Submission; NIH/NCBI, Accession No. NP_938673; Cerdeno-Tarraga et al.; Jun. 3, 2010.

GenPept NCBI, Accession No. XP_001385378; Jeffries et al.; Apr. 11, 2008.

GenPept NCBI, Accession No. XP_002097000; Clark et al.; Aug. 12, 2009.

GenPept NCBI, Accession No. XP_00234527.; Jul. 7, 2006.

GenPept NCBI, Accession No. ZP_03507634; Gonzalez et al.; Dec. 19, 2008.

GenPept NCBI, Accession No. ZP_06431346; Small et al.; Jun. 9, 2010.

Ghadiali et al., Enzyme-Responsive Nanoparticle Systems. Advanced Materials, 2008 vol. 20(22):4359-4363.

Ghoshal et al., How to Interpret Hydrogen Breath Tests. J Neurogastroenterol Motil. 2011;17:312-7.

Giljohann et al., Drivers of biodiagnostic development. Nature. Nov. 26, 2009;462(7272):461-4. doi: 10.1038/nature08605.

Ginsberg et al., Sensitivity and specificity of a rapid whole-blood assay for D-dimer in the diagnosis of pulmonary embolism. Ann Intern Med. Dec. 15, 1998;129(12):1006-11.

Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.

Grayson et al., Multi-pulse drug delivery from a resorbable polymeric microchip device. Nat Mater. Nov. 2003;2(11):767-72.

Grimm et al., Use of Gene Expression Profiling to Direct in Vivo Molecular Imaging of Lung Cancer. PNAS. Oct. 4, 2005;102(40):14404-9.

Gross, Mass Spectrometry: A Textbook. Springer. $2^{nd}$ ed. Mar. 1, 2011. Chapter 9. 415-452.

Guimaraes et al., Site-specific C-terminal internal loop labeling of proteins using sortase-mediated reactions. Nat Protoc. 2013;8:1787-99.

Haiko et al., The omptins of Yersinia pestis and *Salmonella enterica* cleave the reactive center loop of plasminogen activator inhibitor 1. J Bacteriol. Sep. 2010;192(18):4553-61. doi:10.1128/JB.00458-10. Epub Jul. 16, 2010.

Haro et al., Matrix metalloproteinase-7-dependent release of tumor necrosis factor-alpha in a model of herniated disc resorption. J Clin Invest. Jan. 2000;105(2):143-50.

Harris et al., Protease-triggered unveiling of bioactive nanoparticles. Small. 2008;4(9):1307-12. doi: 10.1002/smll.200701319. Epub Aug. 8, 2008.

Haskins, The application of stable isotopes in biomedical research. Biomed Mass Spectrom. Jul. 1982;9(7):269-77.

Haun et al., Micro-NMR for rapid molecular analysis of human tumor samples. Sci Transl Med. Feb. 23, 2011;3(71):71ra16. doi: 10.1126/scitranslmed.3002048.

Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.

Herbig et al., Towards standardization in the analysis of breath gas volatiles. J Breath Res. 2014;8:1-11.

Holliday et al., Rapid Identification of Staphylococcus aureus by Using Fluorescent Staphylocoagulase Assays. J Clin Microbiol. Apr. 1999;37(4):1190-2.

Imai et al., Degradation of decorin by matrix metalloproteinases: identification of the cleavage sites, kinetic analyses and transforming growth factor-beta1 release. Biochem J. Mar. 15, 1997;322 (Pt 3):809-14.

Ito et al., Degradation of interleukin 1beta by matrix metalloproteinases. J Biol Chem. Jun. 21, 1996;271(25):14657-60.

Iwasaki et al., Control of adaptive immunity by the innate immune system. Nat Immunol. Mar. 19, 2015;16(4):343-53.

Jaffer et al., In vivo imaging of thrombin activity in experimental thrombi with thrombin-sensitive near-infrared molecular probe. Arterioscler Thromb Vasc Biol. Nov. 1, 2002;22(11):1929-35.

Janzen et al., Colorimetric sensor arrays for volatile organic compounds. Anal Chem. Jun. 1, 2006;78(11):3591-600.

Jiang et al., Tumor imaging by means of proteolytic activation of cell-penetrating peptides. Proc. Natl. Acad. Sci. U. S. A. 2004;101:17867-17872.

Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.

Johnson et al., Computer program (SEQPEP) to aid in the interpretation of high-energy collision tandem mass spectra of peptides. Biomed Environ Mass Spectrom. Nov. 1989;18(11):945-57.

Kalinska et al., Substrate specificity of Staphylococcus aureus cysteine proteases—Staphopains A, B and C. Biochimie. Feb. 2012;94(2):318-27. doi: 10.1016/j.biochi.2011.07.020. Epub Jul. 23, 2011.

(56) References Cited

OTHER PUBLICATIONS

Kaman et al., Evaluation of a FRET-Peptide Substrate to Predict Virulence in Pseudomonas aeruginosa. PLoS One; Nov. 2013;8(11):e81428.
Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.
Kasperkiewicz et al., Design of ultrasensitive probes for human neutrophil elastase through hybrid combinatorial substrate library profiling. PNAS. 2014;111:2518-23.
Kastelic et al., Stefin B, the major low molecular weight inhibitor in ovarian carcinoma. Cancer Lett. Jul. 15, 1994;82(1):81-8.
Kim et al., Applications of stable, nonradioactive isotope tracers in in vivo human metabolic research. Exp Mol Med. Jan. 2016; 48(1): e203. Epub Jan. 15, 2016. doi: 10.1038/emm.2015.97.
Kircher et al., A dual fluorochrome probe for imaging proteases. Bioconjug Chem. Mar.-Apr. 2004;15(2):242-8.
Kirkpatrick et al., Noninvasive lung cancer detection via pulmonary protease profiling. bioRxiv. 36 pages. doi: https://doi.org/10.1101/495259.
Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.
Krebs et al., Molecular analysis of circulating tumour cells—biology and biomarkers. Nat Rev Clin Oncol. 2014;11:129-44.
Krilaviciute et al., Detection of cancer through exhaled breath : a systematic review Literature search. Oncotarget. 2015;6:38643-57.
Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kulkarni et al., MMP-9 Responsive PEG Cleavable Nanovesicles for Efficient Delivery of Chemotherapeutics to Pancreatic Cancer. Mol Pharm. Jul. 7, 2014; 11(7): 2390-2399. doi: 10.1021/mp500108p.
Kwak et al., Volatile disease biomarkers in breath: a critique. Curr Pharm Biotechnol; 2011;12:1067-74.
Kwon et al., Porous Silicon Nanoparticle Delivery of Tandem Peptide Anti-Infectives for the Treatment of Pseudomonas aeruginosa Lung Infections. Adv Mat. Sep. 20, 2017;29(35). 21pages.
Kwon et al., Ultrasensitive tumour-penetrating nanosensors of protease activity. Nat Biomed Eng. 2017;1. pii: 0054. doi:10.1038/s41551-017-0054. Epub Apr. 10, 2017.
Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.
Kwong et al., Mathematical framework for activity-based cancer biomarkers. Proc Natl Acad Sci U S A. Oct. 13, 2015;112(41):12627-32. doi: 10.1073/pnas.1506925112. Epub Sep. 28, 2015.
Lange et al., Selected reaction monitoring for quantitative proteomics: a tutorial. Mol Syst Biol. 2008;4:222. doi: 10.1038/msb.2008.61. Epub Oct. 14, 2008.
Larsen et al., Assay of plasma heparin using thrombin and the chromogenic substrate H-D-Phe-Pip-Arg-pNA (S-2238). Thromb Res. Aug. 1978;13(2):285-8.
Laupland et al., The changing culture of the microbiology laboratory. Can J Infect Dis Med Microbiol. 2013 Autumn; 24(3):125-128. doi: 10.1155/2013/101630.
Lebeau et al., Imaging active urokinase plasminogen activator in prostate cancer. Cancer Res. Apr. 1, 2015;75(7):1225-35. doi: 10.1158/0008-5472.CAN-14-2185. Epub Feb. 11, 2015.
Levi et al., Matrix metalloproteinase 2 releases active soluble ectodomain of fibroblast growth factor receptor 1. Proc Natl Acad Sci U S A. Jul. 9, 1996;93(14):7069-74.
Lin et al., Drug-induced amplification of nanoparticle targeting to tumors. Nano Today. Oct. 2014;9(5):550-559. doi:10.1016/j.nantod.2014.09.001. Epub Sep. 23, 2014.
Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.
Liou et al., Nonisotropic Enzyme-Inhibitor Interactions: A Novel Nonoxidative Mechanism for Quantum Proteolysis by Human Neutrophils. Biochem. 1995;34(49):16171-7.
Liu et al., Structure-based programming of lymph-node targeting in molecular vaccines. Nature. Mar. 27, 2014;507(7493):519-22. doi: 10.1038/nature12978. Epub Feb. 16, 2014.
Longo et al., In Vivo Imaging of Tumor Metabolism and Acidosis by Combining PET and MRI-CEST pH Imaging. Cancer Res. Nov. 15, 2016;76(22):6463-6470. doi: 10.1158/0008-5472.CAN-16-0825. Epub Sep. 20, 2016. PMID: 27651313.
Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.
Mallick et al., Computational prediction of proteotypic peptides for quantitative proteomics. Nat Biotechnol. Jan. 2007;25(1):125-31. Epub Dec. 31, 2006.
Mañes et al., The matrix metalloproteinase-9 regulates the insulin-like growth factor-triggered autocrine response in DU-145 carcinoma cells. J Biol Chem. Mar. 12, 1999;274(11):6935-45.
Martinez et al., Diagnostics for the developing world: microfluidic paper-based analytical devices. Anal Chem. Jan. 1, 2010;82(1):3-10. doi: 10.1021/ac9013989.
Matsumoto et al., Role of bacterial proteases in pseudomonal and serratial keratitis. Biol Chem. Jan. 2004;385(11):1007-16.
McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.
McLennan et al., Subcutaneous drug delivery and the role of the lymphatics. Drug Discov Today Technol. 2005 Spring;2(1):89-96. doi:10.1016/j.ddtec.2005.05.006.
Meyer et al., Respiratory protease / antiprotease balance determines susceptibility to viral infection and can be modified by nutritional antioxidants. Am J Physiol Lung Cell Mol Physiol. 2015;308:L1189-L1201.
Mira et al., Insulin-like growth factor I-triggered cell migration and invasion are mediated by matrix metalloproteinase-9. Endocrinology. Apr. 1999;140(4):1657-64.
Mirtti et al., Expression of cystatins, high molecular weight cytokeratin, and proliferation markers in prostatic adenocarcinoma and hyperplasia. Prostate. Mar. 1, 2003;54(4):290-8.
Mitchell et al., Assay for plasma heparin using a synthetic peptide substrate for thrombin: introduction of the fluorophore aminoisophthalic acid, dimethyl ester. Thromb Res. Jul. 1978;13(1):47-52.
Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.
Morihara, Pseudolysin and other pathogen endopeptidases of thermolysin family. Methods in Enzymol. 1995;248:242-53.
Morris et al., Urine and plasma levels of fibrinopeptide B in patients with deep vein thrombosis and pulmonary embolism. Thromb Res. May 1, 2003;110(2-3):159-65.
Murray, What Is New in Clinical Microbiology—Microbial Identification by MALDI-TOF Mass Spectrometry. JMDI. 2012;14:419-23.
Nagase et al., Matrix metalloproteinases. J Biol Chem. Jul. 30, 1999;274(31):21491-4.
Nahrendorf et al., Hybrid in vivo FMT-CT imaging of protease activity in atherosclerosis with customized nanosensors. Arterioscler Thromb Vasc Biol. Oct. 2009;29(10):1444-51. doi:10.1161/ATVBAHA.109.193086. Epub Jul. 16, 2009. Supplemental Material.
Nizio et al., In vitro volatile organic compound profiling using GCxGC-TOFMS to differentiate bacteria associated with lung infections: a proof-of-concept study. J Breath Res. Apr. 27, 2016;10:026008, 12 pages.

(56) References Cited

OTHER PUBLICATIONS

Nomura et al., Activity-based protein profiling for biochemical pathway discovery in cancer. Nat Rev Cancer. Sep. 2010;10(9):630-8. doi: 10.1038/nrc2901. Epub Aug. 12, 2010.
Nouh et al., Cathepsin B: a potential prognostic marker for inflammatory breast cancer. J Transl Med. 2011;9(1):8 pages.
Olson et al., In vivo characterization of activatable cell penetrating peptides for targeting protease activity in cancer. Integr Biol (Camb). Jun. 2009; 1(5-6):382-93.
Olson et al., In vivo fluorescence imaging of atherosclerotic plaques with activatable cell-penetrating peptides targeting thrombin activity. Integr Biol (Camb). Jun. 2012;4(6):595-605. doi:10.1039/c2ib00161f. Epub Apr. 26, 2012.
Ong et al., Inhalable nanosensors for rapid breath-based pathogen identification in respiratory infection. Adv Res Technol Symp. Mar. 5, 2018.
Ong et al., Use of Mass Spectrometric Vapor Analysis To Improve Canine Explosive Detection Efficiency. Anal Chem. 2017;89:6482-90.
Park et al., Magnetic Iron Oxide Nanoworms for Tumor Targeting and Imaging. Adv Mater. May 5, 2008;20(9):1630-1635.
Park et al., Systematic surface engineering of magnetic nanoworms for in vivo tumor targeting. Small. Mar. 2009;5(6):694-700. doi: 10.1002/smll.200801789.
Parks et al., Matrix metalloproteinases as modulators of inflammation and innate immunity. Nat Rev Immunol. Aug. 2004;4(8):617-29.
Patton et al., Inhaling medicines: delivering drugs to the body through the lungs. Nat Rev Drug Discov. Jan. 2007;6(1):67-74.
Patton et al., The lungs as a portal of entry for systemic drug delivery. Proc Am Thorac Soc. 2004;1(4):338-44.
Peer et al., Nanocarriers as an emerging platform for cancer therapy. Nat Nanotechnol. Dec. 2007;2(12):751-60.
Peng et al., Diagnosing lung cancer in exhaled breath using gold nanoparticles. Nat Nanotechnol. Oct. 2009;4(10):669-73. doi: 10.1038/nnano.2009.235. Epub Aug. 30, 2009.
Phillips et al., Variation in volatile organic compounds in the breath of normal humans. J Chromatogr B. 1999;729:75-88.
Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.
Posthuma-Trumpie et al., Lateral flow (immuno)assay: its strengths, weaknesses, opportunities and threats. A literature survey. Anal Bioanal Chem. Jan. 2009;393(2):569-82. doi:10.1007/s00216-008-2287-2. Epub Aug. 13, 2008.
Potempa et al., Corruption of innate immunity by bacterial proteases. J Innate Immun. 2009;1(2):70-87.
Powell et al., The metalloproteinase matrilysin proteolytically generates active soluble Fas ligand and potentiates epithelial cell apoptosis. Curr Biol. Dec. 16-30, 1999;9(24):1441-7.
Prensner et al., Beyond PSA: the next generation of prostate cancer biomarkers. Sci Transl Med. Mar. 28, 2012;4(127):127rv3. doi: 10.1126/scitranslmed.3003180.
Rajah et al., Elevated levels of the IGF-binding protein protease MMP-1 in asthmatic airway smooth muscle. Am J Respir Cell Mol Biol. Feb. 1999;20(2):199-208.
Rashidian et al., Noninvasive imaging of immune responses. Proc Natl Acad Sci U S A. May 12, 2015;112(19):6146-51. doi: 10.1073/pnas.1502609112. Epub Apr. 20, 2015. Erratum in: Proc Natl Acad Sci U S A. Jul. 3, 2018;115(27):E6387. PMID: 25902531; PMCID: PMC4434737.
Rashidian et al., Predicting the response to CTLA-4 blockade by longitudinal noninvasive monitoring of CD8 T cells. J Exp Med. Aug. 7, 2017;214(8):2243-2255. doi: 10.1084/jem.20161950. Epub Jun. 30, 2017. PMID: 28666979; PMCID: PMC5551571.
Rawlings et al., The MEROPS database of proteolytic enzymes, their substrates and inhibitors in 2017 and a comparison with peptidases in the PANTHER database. Nucleic Acid Res. Jan. 4, 2018;46(D1):D624-D632.

Rennke, How does glomerular epithelial cell injury contribute to progressive glomerular damage? Kidney Int Suppl. Feb. 1994;45:S58-63.
Rijkers et al., Design and synthesis of thrombin substrates with modified kinetic parameters. Thromb Res. Sep. 15, 1995;79(5-6):491-9.
Roepstorff et al., Proposal for a common nomenclature for sequence ions in mass spectra of peptides. Biomed Mass Spectrom. Nov. 1984;11(11):601.
Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.
Ross et al., Volatile compounds in blood headspace and nasal breath. J Breath Res. Sep. 13, 2017;11(4):046001. doi: 10.1088/1752-7163/aa7d10.
Rousalova et al., Granzyme B-induced apoptosis in cancer cells and its regulation (review). Int J Oncol. Dec. 2010;37(6):1361-78. doi: 10.3892/ijo_00000788. PMID: 21042704.
Roy et al., Matrix metalloproteinases as novel biomarkers and potential therapeutic targets in human cancer. J Clin Oncol. 2009;27:5287-97.
Ruoslahti et al., Targeting of drugs and nanoparticles to tumors. J Cell Biol. Mar. 22, 2010;188(6):759-68. doi: 10.1083/jcb.200910104. Epub Mar. 15, 2010.
Salaun et al., MMP-13 In-Vivo Molecular Imaging Reveals Early Expression in Lung Adenocarcinoma. Plos One. 2015;10(7):e0132960, 19 pages. Epub Jul. 20, 2015. doi: 10.1371/journal.pone.0132960.
Santini et al., A controlled-release microchip. Nature. Jan. 28, 1999;397(6717):335-8.
Sawyers, The cancer biomarker problem. Nature. Apr. 3, 2008;452(7187):548-52. doi:10.1038/nature06913.
Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.
Schonbeck et al., Generation of biologically active IL-1 beta by matrix metalloproteinases: a novel caspase-1-independent pathway of IL-1 beta processing. J Immunol. Oct. 1, 1998;161(7):3340-6.
Schuerle et al., Magnetically Actuated Protease Sensors for in Vivo Tumor Profiling. Nano Lett. Oct. 12, 2016;16(10):6303-6310. Epub Sep. 13, 2016.
Schulenburg et al., A FRET-based biosensor for the detection of neutrophil elastase. Analyst. Mar. 7, 2016;141(5):1645-8. doi: 10.1039/c5an01747e.
Sethi et al., Clinical application of volatile organic compound analysis for detecting infectious diseases. Clin Microbiol Rev. Jul. 2013;26(3):462-75. doi: 10.1128/CMR.00020-13.
Shariat et al., Urine detection of survivin is a sensitive marker for the noninvasive diagnosis of bladder cancer. J Urol. Feb. 2004; 171(2 Pt 1):626-30.
Shaw et al., The role and regulation of the extracellular proteases of *Staphylococcus aureus*. Microbiol. Jan. 2004;150:217-28. doi: 10.1099/mic.0.26634-0.
Shibuya et al., Pseudomonas aeruginosa alkaline proteinase might share a biological function with plasmin. Biochim Biophys Acta. Apr. 29, 1991; 1077(3):316-24.
Smith et al., Rapid identification of highly active and selective substrates for stromelysin and matrilysin using bacteriophage peptide display libraries. J Biol Chem. Mar. 24, 1995;270(12):6440-9.
Stach et al., Unique Substrate Specificity of SplE Serine Protease from *Staphylococcus aureus*. Structure. Apr. 3, 2018;26(4):572-579. e4. doi: 10.1016/j.str.2018.02.008. Epub Mar. 8, 2018.
Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.
Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.
Sun et al., A PET imaging approach for determining EGFR mutation status for improved lung cancer patient management. Sci Transl Med. Mar. 7, 2018;10(431):eaan8840. doi:10.1126/scitranslmed.aan8840. PMID: 29515002.

(56) References Cited

OTHER PUBLICATIONS

Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.
Suzuki et al., Matrix metalloproteinase-3 releases active heparin-binding EGF-like growth factor by cleavage at a specific juxtamembrane site. J Biol Chem. Dec. 12, 1997;272(50):31730-7.
Sweeney et al., Robust classification of bacterial and viral infections via integrated host gene expression diagnostics. Sci Transl Med. Jul. 2016;8(346):346ra91.
Tascilar et al., Role of tumor markers and mutations in cells and pancreatic juice in the diagnosis of pancreatic cancer. Ann Oncol. 1999;10 Suppl 4:S107-10.
Taylor et al., Integrative genomic profiling of human prostate cancer. Cancer Cell. Jul. 13, 2010;18(1):11-22. doi: 10.1016/j.ccr.2010.05.026. Epub Jun. 24, 2010.
Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.
Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].
Thorek et al., Internalization of secreted antigen-targeted antibodies by the neonatal Fc receptor for precision imaging of the androgen receptor axis. Sci Transl Med. Nov. 30, 2016;8(367):367ra167.
Tockman et al., Considerations in bringing a cancer biomarker to clinical application. Cancer Res. May 1, 1992;52(9 Suppl):2711s-2718s.
Trapani et al., Killing by cytotoxic T cells and natural killer cells: multiple granule serine proteases as initiators of DNA fragmentation. Immunol Cell Biol. 1993;71(3):201-8.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.
Truong et al., Isotope-coded chemical reporter and acid-cleavable affinity reagents for monitoring protein sulfenic acids. Bioorg Med Chem Lett. Sep. 1, 2011;21(17):5015-20. doi:10.1016/j.bmcl.2011.04.115. Epub May 3, 2011.
Tung et al., A novel near-infrared fluorescence sensor for detection of thrombin activation in blood. Chembiochem. Mar. 1, 2002;3(2-3):207-11.
Van der Schee et al., Breathomics in lung disease. Chest. 2015;147:224-31.
Vandooren et al., Zymography Methods for Visualizing Hydrolytic Enzymes. Nat Methods. Mar. 2013;10(3):211-20. doi: 10.1038/nmeth.2371.
Vasiljeva et al., Monitoring protease activity in biological tissues using antibody prodrugs as sensing probes. Sci Rep. Apr. 3, 2020;10(1):5894.
Vessillier et al., Hydrolysis of glycine-containing elastin pentapeptides by LasA, a metalloelastase from Pseudomonas aeruginosa. Eur J Biochem. Feb. 2001;268(4):1049-57.
Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.
Warren et al., Disease detection by ultrasensitive quantification of microdosed synthetic urinary biomarkers. J Am Chem Soc. 2014;136:13709-14.
Warren et al., Harnessing protease activity to improve cancer care. Annual Rev Cancer Biol. 2018;2:353-76.
Warren et al., Point-of-care diagnostics for noncommunicable diseases using synthetic urinary biomarkers and paper microfluidics. Proc Natl Acad Sci U S A. Mar. 11, 2014;111(10):3671-6. doi:10.1073/pnas.1314651111. Epub Feb. 24, 2014.

Weerakkody et al., Family of pH (low) insertion peptides for tumor targeting. Proc Natl Acad Sci U S A. Apr. 9, 2013;110(15):5834-9. doi: 10.1073/pnas.1303708110. Epub Mar. 25, 2013. PMID: 23530249; PMCID: PMC3625278.
Weissleder et al., In vivo imaging of tumors with protease-activated near-infrared fluorescent probes. Nat Biotechnol. Apr. 1999;17(4):375-8.
Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.
Welser et al., Protease sensing with nanoparticle based platforms. Analyst. Jan. 7, 2011;136(1):29-41. doi: 10.1039/c0an00429d. Epub Sep. 28, 2010.
Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi:10.1074/mcp.M900254-MCP200. Epub Oct. 20, 2009.
Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.
Whitney et al., Ratiometric activatable cell-penetrating peptides provide rapid in vivo readout of thrombin activation. Angew Chem Int Ed Engl. Jan. 2, 2013;52(1):325-30. doi:10.1002/anie.201205721. Epub Oct. 18, 2012.
Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.
Wilkinson et al., Ventilator-Associated Pneumonia Is Characterized by Excessive Release of Neutrophil Proteases in the Lung. Chest. Dec. 2012;142(6):1425-32.
Wilson et al., Applications and Advances in Electronic-Nose Technologies. Sensors (Basel). 2009;9(7):5099-148. doi: 10.3390/s90705099. Epub Jun. 29, 2009.
Withana et al., Labeling of active proteases in fresh-frozen tissues by topical application of quenched activity-based probes. Nat Protoc. Jan. 2016;11(1):184-91. doi:10.1038/nprot.2016.004. Epub Dec. 30, 2015.
Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.
Wu et al., Expression and clinical significance of matrix metalloproteinase-9 in lymphatic invasiveness and metastasis of breast cancer. PLOS ONE. 2014;9(5):e97804.
Xia et al., Multiplex detection of protease activity with quantum dot nanosenors prepared by Intein-Mediated specific bioconjugation. Analytical Chemistry. Nov. 15, 2008; 22(80) 8649-8655.
Yager et al., Point-of-care diagnostics for global health. Annu Rev Biomed Eng. 2008;10:107-44. doi: 10.1146/annurev.bioeng.10.061807.160524.
Yan et al., In Situ Zymography: A Molecular Pathology Technique to Localize Endogenous Protease Activity in Tissue Sections. Vet Pathol May 2003;40(3):227-36.
Yu et al., Cell surface-localized matrix metalloproteinase-9 proteolytically activates TGF-beta and promotes tumor invasion and angiogenesis. Genes Dev. Jan. 15, 2000;14(2):163-76.
Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zheng et al., Dual-reaction triggered sensitivity amplification for ultrasensitive peptide-cleavage based electrochemical detection of matrix metalloproteinase-7. Biosens Bioelectronics. 2018;103:46-52. Epub Feb. 21, 2018.
Zhou et al., Thermo-sensitive microgels supported gold nanoparticles as temperature-mediated catalyst. Chinese J Polym Sci. 2019;37:235-42. Epub Aug. 30, 2018.
Zhu et al., Detecting bacterial lung infections: in vivo evaluation of in vitro volatile fingerprints. J Breath Res. Jan. 10, 2013;7(1):016003, 7 pages.

(56) References Cited

OTHER PUBLICATIONS

Zieske, A perspective on the use of iTRAQ reagent technology for protein complex and profiling studies. J Exp Bot. 2006;57(7):1501-8. Epub Mar. 30, 2006.
Zinnhardt et al., Combined PET Imaging of the Inflammatory Tumor Microenvironment Identifies Margins of Unique Radiotracer Uptake. Cancer Res. Apr. 15, 2017;77(8):1831-1841. doi: 10.1158/0008-5472.CAN-16-2628. Epub Jan. 30, 2017. PMID: 28137769.
Zumla et al., Rapid point of care diagnostic tests for viral and bacterial respiratory tract infections—needs, advances, and future prospects. Lancet Infect Dis. 2014;14(11):1123-35.
[No Author Listed], Amidase Protein Classification Interpro. 2021. 2 pages.
Barchetta et al., Circulating dipeptidyl peptidase-4 is independently associated with the presence and severity of NAFLD/NASH in individuals with and without obesity and metabolic disease. J Endocrinol Invest. May 2021;44(5):979-988. doi: 10.1007/s40618-020-01392-5. Epub Aug. 27, 2020. PMID: 32852705; PMCID: PMC8049937.
Gatter et al., Transferrin receptors in human tissues: their distribution and possible clinical relevance. J Clin Pathol. May 1983;36(5):539-45. doi: 10.1136/jcp.36.5.539. PMID: 6302135; PMCID: PMC498283.
Hao et al., CRISPR-Cas-amplified urine biomarkers for multiplexed and portable cancer diagnostics. bioRxiv Jun. 17, 2020.
Jambunathan et al., Prolyl endopeptidase activity in bronchoalveolar lavage fluid: a novel diagnostic biomarker in a guinea pig model of invasive pulmonary aspergillosis. Med Mycol. Aug. 2013;51(6):592-602. doi: 10.3109/13693786.2012.761360. Epub Jan. 28, 2013.
Kalubowilage et al., Early detection of pancreatic cancers in liquid biopsies by ultrasensitive fluorescence nanobiosensors. Nanomedicine. Aug. 2018;14(6):1823-1832. doi:10.1016/j.nano.2018.04.020. Epub May 18, 2018. PMID: 29782949.
Klan et al., Photoremovable protecting groups in chemistry and biology: reaction mechanisms and efficacy. Chem Rev. Jan. 9, 2013;113(1):119-91. doi: 10.1021/cr300177k. Epub Dec. 21, 2012. PMID: 23256727; PMCID: PMC3557858.
Loynachan et al., Renal clearable catalytic gold nanoclusters for in vivo disease monitoring. Nat Nanotechnol. Sep. 2019;14(9):883-890. doi: 10.1038/s41565-019-0527-6. Epub Sep. 2, 2019. PMID: 31477801; PMCID: PMC7045344.
Matheeussen et al., Method comparison of dipeptidyl peptidase IV activity assays and their application in biological samples containing reversible inhibitors. Clin Chim Acta. Feb. 18, 2012;413(3-4):456-62. doi: 10.1016/j.cca.2011.10.031. Epub Nov. 7, 2011. PMID: 22093941.
Parker et al., Folate receptor expression in carcinomas and normal tissues determined by a quantitative radioligand binding assay. Anal Biochem. Mar. 15, 2005;338(2):284-93. doi:10.1016/j.ab.2004.12.026. PMID: 15745749.
Soleimany et al., Activity-Based Diagnostics: An Emerging Paradigm for Disease Detection and Monitoring. Trends Mol Med. May 2020;26(5):450-468. doi:10.1016/j.molmed.2020.01.013. Epub Apr. 5, 2020. PMID: 32359477; PMCID: PMC8290463.
Udukala et al., Early detection of non-small cell lung cancer in liquid biopsies by ultrasensitive protease activity analysis. J Cancer Metastasis Treat 2020;6:25.
Yoo et al., 2'-O-methyl-modified phosphorothioate antisense oligonucleotides have reduced non-specific effects in vitro. Nucleic Acids Res. Apr. 2, 2004;32(6):2008-16. doi:10.1093/nar/gkh516. PMID: 15064360; PMCID: PMC390367.
U.S. Appl. No. 15/842,162, filed Dec. 14, 2017, Kwong et al.
U.S. Appl. No. 16/691,788, filed Nov. 22, 2019, Bhatia et al.
U.S. Appl. No. 17/813,899, filed Jul. 20, 2022, Bhatia et al.
U.S. Appl. No. 17/816,765, filed Aug. 2, 2022, Bhatia et al.
U.S. Appl. No. 15/947,644, filed Apr. 5, 2018, Bhatia et al.
U.S. Appl. No. 16/582,053, filed Sep. 25, 2019, Bhatia et al.
U.S. Appl. No. 16/654,572, filed Oct. 16, 2019, Bhatia et al.
Kojima et al., Preparation and characterization of complexes of liposomes with gold nanoparticles. Colloids Surf B Biointerfaces. Oct. 15, 2008;66(2):246-52. doi: 10.1016/j.colsurfb.2008.06.022. Epub Jul. 9, 2008.
Pan et al., Size-dependent cytotoxicity of gold nanoparticles. Small. Nov. 2007;3(11):1941-9.
Pornpattananangkul et al., Bacterial toxin-triggered drug release from gold nanoparticle-stabilized liposomes for the treatment of bacterial infection. J Am Chem Soc. Mar. 23, 2011;133(11):4132-9. doi: 10.1021/ja111110e. Epub Feb. 23, 2011.
Ren et al., Enrichment of cysteine-containing peptides from tryptic digests using a quaternary amine tag. Anal Chem. Aug. 1, 2004;76(15):4522-30.
U.S. Appl. No. 18/056,752, filed Nov. 18, 2022, Bhatia et al.
U.S. Appl. No. 18/049,704, filed Oct. 26, 2022, Bhatia et al.
U.S. Appl. No. 18/063,162, filed Dec. 8, 2022, Kwong et al.
[No Author Listed], Bodipy. Compound Summary. Retrieved from <https://pubchem.ncbi.nlm.nih.gov/compound/Bodipy>>. Accessed Feb. 2023.
[No Author Listed], Lung cancer treatment. Accessed Feb. 2023 <https://mdanderson.org/cancer-types/lung-cancer/lung-cancer-treatment.html>.
[No Author Listed], UNIPROTKB Submission; Accession No. A0A182DWE3.
Adli, The CRISPR tool kit for genome editing and beyond. Nat Commun. May 15, 2018;9(1):1911.
Aung et al., Low protease activity in B cell follicles promotes retention of intact antigens after immunization. Science. Jan. 27, 2023;379(6630):eabn8934. doi: 10.1126/science.abn8934. Epub Jan. 27, 2023.
Aung et al., Low protease activity in B cell follicles promotes retention of intact antigens after immunization. Supplementary Materials. Science. Jan. 27, 2023;379(6630):eabn8934. doi:10.1126/science.abn8934. Epub Jan. 27, 2023.
Badeau et al., Engineered modular biomaterial logic gates for environmentally triggered therapeutic delivery. Nat Chem. Mar. 2018;10(3):251-258. doi: 10.1038/nchem.2917. Epub Jan. 15, 2018.
Bassetti et al., How to manage Pseudomonas aeruginosa infections. Drugs Context. May 29, 2018;7:212527.
Chakravarty et al., Nanobody: the "magic bullet" for molecular imaging? Theranostics. Jan. 29, 2014;4(4):386-98. doi: 10.7150/thno.8006.
Choi et al., Targeting kidney mesangium by nanoparticles of defined size. Proc Natl Acad Sci U S A. Apr. 19, 2011;108(16):6656-61. doi: 10.1073/pnas.1103573108. Epub Apr. 4, 2011.
Corey, Chemical modification: the key to clinical application of RNA interference? J Clin Invest. Dec. 2007;117(12):3615-22.
Czyzewska J et al. "The Expression of Matrix Metalloproteinase 9 And Cathepsin B in Gastric Carcinoma Is Associated With Lymph Node Metastasis, But Not With Postoperative Survival", Folia Histochemica et Cytobiologica, 46(1):57-64; Feb. 26, 2008. (Feb. 26, 2008).
Dahlman et al., Barcoded nanoparticles for high throughput in vivo discovery of targeted therapeutics. Proc Natl Acad Sci U S A. Feb. 21, 2017;114(8):2060-2065. doi:10.1073/pnas.1620874114. Epub Feb. 6, 2017.
English et al., Programmable CRISPR-responsive smart materials. Science. Aug. 23, 2019;365(6455):780-785.
Fischer et al., Structure-activity relationship of truncated and substituted analogues of the intracellular delivery vector Penetratin. J Pept Res. Feb. 2000;55(2):163-72.
Gootenberg et al., Nucleic acid detection with CRISPR-Cas13a/C2c2. Science. Apr. 28, 2017;356(6336):438-442. doi: 10.1126/science.aam9321. Epub Apr. 13, 2017.
Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.
Holt et al.,. Nanosensors to Detect Protease Activity In Vivo for Noninvasive Diagnostics. J Vis Exp. Jul. 16, 2018;(137):57937.
Kaminski et al., A CRISPR-based assay for the detection of opportunistic infections post-transplantation and for the monitoring of transplant rejection. Nat Biomed Eng. Jun. 2020;4(6):601-609. doi: 10.1038/s41551-020-0546-5. Epub Apr. 13, 2020.

(56) References Cited

OTHER PUBLICATIONS

Khvorova et al., The chemical evolution of oligonucleotide therapies of clinical utility. Nat Biotechnol. Mar. 2017;35(3):238-248. doi: 10.1038/nbt.3765. Epub Feb. 27, 2017.

Kim et al., Immunogene therapy with fusogenic nanoparticles modulates macrophage response to *Staphylococcus aureus*. Nat Commun. May 17, 2018;9(1):1969. doi: 10.1038/s41467-018-04390-7.

Kim et al., Securing the Payload, Finding the Cell, and Avoiding the Endosome: Peptide-Targeted, Fusogenic Porous Silicon Nanoparticles for Delivery of siRNA. Adv Mater. Aug. 2019;31(35):e1902952. doi: 10.1002/adma.201902952. Epub Jul. 3, 2019.

Kirkpatrick et al., Urinary detection of lung cancer in mice via noninvasive pulmonary protease profiling. Sci Transl Med. Apr. 1, 2020;12(537):eaaw0262.

Koo et al., Merging new-age biomarkers and nanodiagnostics for precision prostate cancer management. Nat Rev Urol. May 2019;16(5):302-317.

Kratschmer et al., Effect of Chemical Modifications on Aptamer Stability in Serum. Nucleic Acid Ther. Dec. 2017;27(6):335-344. doi: 10.1089/nat.2017.0680. Epub Sep. 25, 2017.

Liu et al., CasX enzymes comprise a distinct family of Rna-guided genome editors. Nature. Feb. 2019;566(7743):218-223. doi: 10.1038/s41586-019-0908-x. Epub Feb. 4, 2019. Erratum in: Nature. Apr. 2019;568(7752):E8-E10.

Lokugamage et al., Testing thousands of nanoparticles in vivo using DNA barcodes. Curr Opin Biomed Eng. Sep. 2018;7:1-8. doi: 10.1016/j.cobme.2018.08.001. Epub Aug. 21, 2018.

Myhrvold et al., Field-deployable viral diagnostics using CRISPR-Cas13. Science. Apr. 27, 2018;360(6387):444-448.

Naba et al., The matrisome: in silico definition and in vivo characterization by proteomics of normal and tumor extracellular matrices. Mol Cell Proteomics. Apr. 2012;11(4):M111.014647. doi: 10.1074/mcp.M111.014647. Epub Dec. 9, 2011.

Park et al., Pathophysiological changes induced by Pseudomonas aeruginosa infection are involved in MMP-12 and MMP-13 upregulation in human carcinoma epithelial cells and a pneumonia mouse model. Infect Immun. Dec. 2015;83(12):4791-9. doi: 10.1128/IAI.00619-15. Epub Oct. 5, 2015.

Pilcer et al., Formulation strategy and use of excipients in pulmonary drug delivery. Int J Pharm. Jun. 15, 2010;392(1-2):1-19. doi: 10.1016/j.ijpharm.2010.03.017. Epub Mar. 17, 2010.

Ronald et al., Detecting cancers through tumor-activatable minicircles that lead to a detectable blood biomarker. Proc Natl Acad Sci U S A. Mar. 10, 2015;112(10):3068-73. doi:10.1073/pnas.1414156112. Epub Feb. 23, 2015.

Shearer et al.,Targeting Liver Fibrosis with a Cell-penetrating Protease-activated Receptor-2 (PAR2) Pepducin. J Biol Chem. Oct. 28, 2016;291(44):23188-23198. doi:10.1074/jbc.M116.732743. Epub Sep. 9, 2016.

Smith et al., Therapeutic Oligonucleotides: State of the Art. Annu Rev Pharmacol Toxicol. Jan. 6, 2019;59:605-630. doi: 10.1146/annurev-pharmtox-010818-021050. Epub Oct. 9, 2018.

Yaari et al., Theranostic barcoded nanoparticles for personalized cancer medicine. Nat Commun. Nov. 10, 2016;7:13325.

Zuo et al. Institute collection and analysis of Nanobodies (iCAN): a comprehensive database and analysis platform for nanobodies. BMC Genomics. Oct. 17, 2017;18(1):797.

U.S. Appl. No. 17/570,847, filed Jan. 7, 2022, Bhatia et al.
PCT/US2020/014007, Jul. 29, 2021, International Preliminary Report on Patentability.
U.S. Appl. No. 17/091,075, filed Nov. 6, 2020, Bhatia et al.
U.S. Appl. No. 17/124,999, filed Dec. 17, 2020, Bhatia et al.
PCT/US2020/014007, Jun. 3, 2020, International Search Report and Written Opinion.

\* cited by examiner

SEQUENCE LISTING

<160> NUMBER OF SEQ ID NOS: 40

<210> SEQ ID NO 1
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 1

```
Ser Leu Lys Arg Tyr Gly Gly Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 2

Ala Ala Phe Arg Ser Arg Gly Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (7)..(8)
<223> OTHER INFORMATION: Xaa can be any amino acid

<400> SEQUENCE: 3

Xaa Xaa Phe Arg Phe Phe Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 4

Gln Ser Val Gly Phe Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Leu Gly Leu Glu Gly Ala Asp
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 6

Gly Pro Leu Asp
1

<210> SEQ ID NO 7
```

```
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 7

Leu Gly Val Leu Ile Val
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 8

Gly Leu Val Leu Val Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 9

Pro Ala Ala Leu Val Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 10

Gly Pro Ala Gly Leu Ala Gly
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 11

Gly Gly Pro Leu Gly Val Arg Gly Lys Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: D amino acid

<400> SEQUENCE: 12

Gly Gly Phe Pro Arg Ser Gly Gly Gly Lys
1               5                   10
```

<210> SEQ ID NO 13
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 13

Glu Gly Val Asn Asp Asn Glu Glu Gly Phe Phe Ser Ala Arg
1               5                   10

<210> SEQ ID NO 14
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 14

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr
            35

<210> SEQ ID NO 15
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 15

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
                20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 16

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
                20                  25                  30

<210> SEQ ID NO 17
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 17

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp

<210> SEQ ID NO 18
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 18

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 19

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 20
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 20

Cys Asp Asn Asn Asn Pro Trp Arg Ala Tyr Leu Asp Leu Phe Pro
1               5                   10                  15

Thr Asp Thr Leu Leu Leu Asp Trp
            20

<210> SEQ ID NO 21
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 21

Ala Cys Glu Glu Gln Asn Pro Trp Ala Arg Tyr Leu Glu Trp Leu Phe
1               5                   10                  15

Pro Thr Glu Thr Leu Leu Leu Glu Leu
            20                  25

<210> SEQ ID NO 22
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 22

Cys Glu Glu Gln Gln Pro Trp Ala Gln Tyr Leu Glu Leu Leu Phe Pro
1               5                   10                  15

Thr Glu Thr Leu Leu Leu Glu Trp
            20

<210> SEQ ID NO 23
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 23

Cys Glu Glu Gln Gln Pro Trp Arg Ala Tyr Leu Glu Leu Leu Phe Pro
1               5                   10                  15

Thr Glu Thr Leu Leu Leu Glu Trp
            20

<210> SEQ ID NO 24
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 24

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 25
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 25

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 26

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 27
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 27

Ala Cys Glu Glu Gln Asn Pro Trp Ala Arg Tyr Ala Glu Leu Leu Phe
1               5                   10                  15

```
Pro Thr Thr Leu Ala Trp
            20

<210> SEQ ID NO 28
<211> LENGTH: 34
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: modified with acetyl group
<220> FEATURE:
<221> NAME/KEY: MISC_FEATURE
<222> LOCATION: (34)..(34)
<223> OTHER INFORMATION: modified with amide group

<400> SEQUENCE: 28

Thr Glu Asp Ala Asp Val Leu Leu Ala Leu Asp Leu Leu Leu Pro
1               5                  10                  15

Thr Thr Phe Leu Trp Asp Ala Tyr Arg Ala Trp Tyr Pro Asn Gln Glu
            20                  25                  30

Cys Ala

<210> SEQ ID NO 29
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 29

Cys Asp Asp Asp Asp Asn Pro Asn Tyr Trp Ala Arg Tyr Ala Asn
1               5                  10                  15

Trp Leu Phe Thr Thr Pro Leu Leu Leu Asn Gly Ala Leu Leu Val
            20                  25                  30

Glu Ala Glu Glu Thr
        35

<210> SEQ ID NO 30
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 30

Cys Asp Asp Asp Asp Asn Pro Asn Tyr Trp Ala Arg Tyr Ala Pro
1               5                  10                  15

Trp Leu Phe Thr Thr Pro Leu Leu Leu Pro Gly Ala Leu Leu Val
            20                  25                  30

Glu Ala Glu Glu Thr
        35

<210> SEQ ID NO 31
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 31

Ala Ala Glu Gln Asn Pro Ile Tyr Trp Ala Arg Tyr Ala Asp Trp Leu
```

```
1               5                   10                  15
Phe Thr Thr Pro Leu Leu Leu Leu Asp Leu Ala Leu Leu Val Asp Ala
                20                  25                  30

Asp Glu Gly Thr Cys
            35

<210> SEQ ID NO 32
<211> LENGTH: 37
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (37)..(37)
<223> OTHER INFORMATION: Modified with cyanine

<400> SEQUENCE: 32

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
                20                  25                  30

Asp Glu Gly Thr Cys
            35

<210> SEQ ID NO 33
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (28)..(29)
<223> OTHER INFORMATION: D-amino acids

<400> SEQUENCE: 33

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp Lys Lys
                20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(3)
<223> OTHER INFORMATION: Modified with cyanine
<220> FEATURE:
<221> NAME/KEY: MISC_FEATURE
<222> LOCATION: (28)..(29)
<223> OTHER INFORMATION: D-amino acids

<400> SEQUENCE: 34

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp Lys Lys
                20                  25

<210> SEQ ID NO 35
<211> LENGTH: 32
<212> TYPE: PRT
```

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with azide side chain
<220> FEATURE:
<221> NAME/KEY: MISC_FEATURE
<222> LOCATION: (31)..(32)
<223> OTHER INFORMATION: D-amino acids

<400> SEQUENCE: 35

Lys Gly Gly Ala Cys Asp Asp Gln Asn Pro Trp Arg Ala Tyr Leu Asp
1               5                   10                  15

Leu Leu Phe Pro Thr Asp Thr Leu Leu Leu Asp Leu Leu Trp Lys Lys
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with azide side chain
<220> FEATURE:
<221> NAME/KEY: MISC_FEATURE
<222> LOCATION: (4)..(32)
<223> OTHER INFORMATION: D-amino acids

<400> SEQUENCE: 36

Lys Gly Gly Ala Cys Asp Asp Gln Asn Pro Trp Arg Ala Tyr Leu Asp
1               5                   10                  15

Leu Leu Phe Pro Thr Asp Thr Leu Leu Leu Asp Leu Leu Trp Lys Lys
            20                  25                  30

<210> SEQ ID NO 37
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (28)..(29)
<223> OTHER INFORMATION: D-amino acids

<400> SEQUENCE: 37

Ala Cys Asp Asp Gln Asn Pro Trp Arg Ala Tyr Leu Lys Leu Leu Phe
1               5                   10                  15

Pro Thr Lys Thr Leu Leu Leu Lys Leu Leu Trp Lys Lys
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(3)
<223> OTHER INFORMATION: Modified with cyanine
<220> FEATURE:
<221> NAME/KEY: MISC_FEATURE
<222> LOCATION: (28)..(29)
<223> OTHER INFORMATION: D-amino acids
```

```
<400> SEQUENCE: 38

Ala Cys Asp Asp Gln Asn Pro Trp Arg Ala Tyr Leu Lys Leu Leu Phe
1               5                   10                  15

Pro Thr Lys Thr Leu Leu Leu Lys Leu Leu Trp Lys Lys
                20                  25

<210> SEQ ID NO 39
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with azide side chain
<220> FEATURE:
<221> NAME/KEY: MISC_FEATURE
<222> LOCATION: (31)..(32)
<223> OTHER INFORMATION: D-amino acids

<400> SEQUENCE: 39

Lys Gly Gly Ala Cys Asp Asp Gln Asn Pro Trp Arg Ala Tyr Leu Lys
1               5                   10                  15

Leu Leu Phe Pro Thr Lys Thr Leu Leu Leu Lys Leu Leu Trp Lys Lys
                20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with azide side chain
<220> FEATURE:
<221> NAME/KEY: MISC_FEATURE
<222> LOCATION: (4)..(32)
<223> OTHER INFORMATION: D-amino acids

<400> SEQUENCE: 40

Lys Gly Gly Ala Cys Asp Asp Gln Asn Pro Trp Arg Ala Tyr Leu Asp
1               5                   10                  15

Leu Leu Phe Pro Thr Asp Thr Leu Leu Leu Asp Leu Leu Trp Lys Lys
                20                  25                  30
```

SENSORS FOR DETECTING AND IMAGING OF CANCER METASTASIS

CROSS-REFERENCE TO RELATED APPLICATIONS

This application claims the benefit of priority under 35 U.S.C. § 119(e) of U.S. provisional application Ser. No. 62/793,805, filed Jan. 17, 2019, the disclosure of which is incorporated by reference here in its entirety.

FIELD

The disclosure relates, in some aspects, to improved methods and products associated with detecting, localizing, and monitoring the activity of proteases in vivo or in vitro. These methods and products form the basis of, and may be used as, an ultrasensitive diagnostic platform.

BACKGROUND

More than 90% of all cancer-related deaths are caused by metastasis. For example, five-year survival rate of colorectal cancer (CRC) patients with large, distant metastases is significantly reduced compared to those with only localized, primary lesions. Although early detection of metastases may save many lives, their small size, multiplicity and ability to invade diverse organs make sensitive detection an elusive goal. Beyond early detection, pretreatment stratification and response assessment are critical to establishing a robust therapeutic strategy.

SUMMARY

Aspects of the present disclosure provide a protease imaging sensor comprising: (a) a scaffold linked to an enzyme-specific substrate that is attached to a first detectable marker, wherein the first detectable marker is capable of being released from the sensor when exposed to an enzyme, and, (b) a tumor imaging agent comprising a second detectable marker, wherein the tumor imaging agent is linked to the scaffold and wherein the tumor imaging agent does not include a cell penetrating domain.

In some embodiments, the tumor imaging agent further comprises a pH low insertion peptide.

In some embodiments, the scaffold comprises a protein, a polymer, or a nanoparticle. The protein, polymer, or nanoparticle may be greater than about 5 nm in diameter.

In some embodiments, the scaffold comprises a multi-arm polyethylene glycol molecule (multi-arm PEG). In some embodiments, the multi-arm PEG comprises 2-20 arms. In some embodiments, the multi-arm PEG comprises 8 arms. In some embodiments, the multi-arm PEG has a total diameter between 5 nm and 20 nm, optionally wherein the multi-arm PEG has a total diameter of about 15 nm.

In some embodiments, the scaffold comprises an iron oxide nanoparticle (IONP), optionally wherein the IONP is between about 10 nm and about 20 nm in size.

In some embodiments, each enzyme-specific substrate comprises a cancer substrate, optionally wherein the cancer substrate is cleaved by an enzyme associated with colorectal cancer (CRC). In some embodiments, the cancer substrate is a cancer metastasis substrate, optionally wherein the cancer metastasis substrate is cleaved by an enzyme associated with colorectal cancer metastasis.

In some embodiments, the first detectable marker comprises a peptide, a nucleic acid, a small molecule, a fluorophore, a carbohydrate, a particle, a radiolabel, a MRI-active compound, a ligand encoded reporter, or a isotope coded reporter molecule (iCORE).

In some embodiments, the second detectable marker comprises a radiolabel and is detectable by positron emission tomography or computerized tomography. In some embodiments, the radiolabel is selected from the group consisting of $^{64}$Cu, Gd(DOTA), $^{201}$Tl, $^{99m}$Tc, $^{18}$F-2-deoxyfluoroglucose (FDG), (18)F-fluoride, gadodiamide, radioisotopes of Pb(II), $^{111}$In, and $^{89}$Zr. In some embodiments, the second detectable marker comprises a metal chelator selected from the group consisting of 1,4,7-Triazacyclononane-1,4,7-triacetic acid (NOTA), 1,4,7,10-tetraazacyclododecane-N,N',N'',N'''-tetraacetic acid (DOTA), Diethylenetriaminepentaacetic Anhydride (DTPA), 1,4,8,11-tetraazacyclotetradecane-1,4,8,11-tetraacetic acid (TETA), and deferoxamine (e.g., for $^{89}$Zr).

In some embodiments, the pH low insertion peptide is selected from the group consisting of SEQ ID NOs: 14-40. In some embodiments, the pH low insertion peptide comprises a D-amino acid, an azide side chain, and/or cyanine. In some embodiments, the tumor imaging peptide is N-terminally linked to the scaffold.

In some embodiments, the scaffold comprises a single enzyme-specific substrate, a single tumor imaging peptide, or a combination thereof. In some embodiments, the scaffold comprises multiple enzyme-specific substrates, multiple tumor imaging peptides, or a combination thereof. In some embodiments, the ratio of the number of enzyme-specific substrates to the number of tumor imaging peptides is 1:1.

Another aspect of the present disclosure provides a method for detecting a tumor in a subject, the method comprising: (a) administering to a subject a protease imaging sensor, wherein the protease imaging sensor comprises (i) a scaffold linked to an enzyme-specific substrate that is attached to a first detectable marker, wherein the first detectable marker is capable of being released from the sensor when exposed to a cancer-associated enzyme at a site within the subject, and (ii) a tumor imaging peptide comprising a second detectable marker, wherein the tumor imaging peptide is linked to the scaffold and wherein the tumor imaging agent does not include a cell penetrating domain; and (b) detecting in a biological sample obtained from the subject the first detectable marker, wherein detection of the first detectable marker in the biological sample is indicative of the subject having a tumor and/or detecting in the subject the second detectable marker, wherein detection of the second detectable marker indicates the site of exposure to the cancer-associated enzyme.

In some embodiments, the tumor imaging peptide comprises a pH low insertion peptide.

In some embodiments, the method comprises detecting the first detectable marker and detecting the second detectable marker.

In some embodiments, the biological sample is not derived from the site of exposure to the cancer-associated enzyme, optionally wherein the sample is a urine sample, blood sample, or tissue sample.

In some embodiments, the site of exposure to the cancer-associated enzyme is a site of metastasis. In some embodiments, the site of metastasis is selected from the group consisting of lung, liver, or heart.

In some embodiments, the method further comprises quantifying the amount of the second detectable marker.

In some embodiments, the detecting of the first detectable marker comprises a method selected from mass spectrometry, PCR analysis, DNA microarray, fluorescence analysis, a capture assay (e.g., ELISA), optical imaging, magnetic resonance imaging (MRI), positron emission tomography (PET) imaging, computerized tomography (CT) imaging, intraoperative imaging or any combination thereof.

In some embodiments, the detecting of the second detectable marker comprises a method selected from fluorescence analysis, optical imaging, magnetic resonance imaging (MRI), positron emission tomography (PET) imaging, computerized tomography (CT) imaging, intraoperative imaging, or any combination thereof.

In some embodiments, the subject is suspected of having, at risk for, or has cancer, optionally wherein the cancer is colorectal cancer.

In some embodiments, the subject has been administered a therapeutic agent.

In some embodiments, the method further comprises classifying a cancer as metastatic or non-metastatic.

Another aspect of the present disclosure provides a method for monitoring tumor progression in a subject, the method comprising: (a) administering to a subject having a tumor a protease imaging sensor, wherein the protease imaging sensor comprises (i) a scaffold linked to an enzyme-specific substrate that is attached to a first detectable marker, wherein the first detectable marker is capable of being released from the sensor when exposed to a cancer-associated enzyme at a site within the subject, and (ii) a tumor imaging peptide comprising a second detectable marker, wherein the tumor imaging peptide is linked to the scaffold and wherein the tumor imaging agent does not include a cell penetrating domain; (b) detecting in a biological sample obtained from the subject the first detectable marker, wherein detection of the first detectable marker in the biological sample is indicative of the subject having a tumor and/or detecting in the subject the second detectable marker, wherein detection of the second detectable marker indicates the site of exposure to the cancer-associated enzyme; and (c) repeating (a) and (b) at least once, thereby monitoring tumor progression in the subject.

In some embodiments, the subject has been administered a first therapeutic agent, a first therapeutic intervention has been performed on the subject, or a combination thereof.

In some embodiments, the method comprises detecting the first detectable marker and detecting the second detectable marker.

In some embodiments, the tumor imaging peptide comprises a pH low insertion peptide.

In some embodiments, the biological sample is not derived from the site of exposure to the cancer-associated enzyme, optionally wherein the sample is a urine sample, blood sample, or tissue sample.

In some embodiments, the site of exposure to the cancer-associated enzyme is a site of metastasis.

In some embodiments, the site of metastasis is selected from the group consisting of lung, liver, or heart.

In some embodiments, the method further comprises quantifying the amount of the second detectable marker.

In some embodiments, the detecting of the first detectable marker comprises a method selected from mass spectrometry, PCR analysis, DNA microarray, fluorescence analysis, a capture assay (e.g., ELISA), optical imaging, magnetic resonance imaging (MRI), positron emission tomography (PET) imaging, computerized tomography (CT) imaging, intraoperative imaging or any combination thereof.

In some embodiments, the detecting of the second detectable marker comprises a method selected from fluorescence analysis, optical imaging, magnetic resonance imaging (MRI), positron emission tomography (PET) imaging, computerized tomography (CT) imaging, intraoperative imaging, or any combination thereof.

In some embodiments, the subject has colorectal cancer.

In some embodiments, the method further comprises classifying a tumor as progressing, in remission, or stable.

The details of one or more embodiments of the invention are set forth in the description below. Other features or advantages of the present invention will be apparent from the following drawings and detailed description of several embodiments, and also from the appended claims.

BRIEF DESCRIPTION OF DRAWINGS

FIG. 2A shows a structure of PRISM built on multivalent polyethylene glycol (PEG) scaffolds to carry two functional components. FIG. 2B shows that acidic pH specificity was demonstrated in MMP9-secreting MC26 cells at pH 6.5, with substantially higher cell accumulation than that observed at pH 7.4. FIG. 2C shows a typical in vivo experimental time line. FIG. 2D shows histology of sham (left) and tumor-bearing mice (right). FIG. 2E is a histological image showing the presence of metastasis in the liver. FIG. 2F is a histological image showing the presence of metastasis in the liver. FIG. 2G shows a comparison of urinary signals generated by two sets of sensors bearing pHLIP or its non-targeting counterpart (NT-pHLIP) (SEQ ID NOS: 35 and 39). FIG. 2H shows IHC staining of MMP9 in sham (right) and tumor-bearing mice (left). FIG. 2I shows Cy7-labeled PRISM specifically accumulated in metastasis in liver reflected by the fluorescent signal from the dye-labeled peptides (SEQ ID NOS: 34 and 38). The left image shows localization of pHLIP. The right image shows localization of NT-pHLIP. FIG. 2J shows quantification of fluorescence intensity of pHLIP and NT-pHLIP along the dotted lines shown in FIG. 2I.

FIG. 3A show radioactive PRISM for PET/CT imaging were constructed through chelation of radioactive isotope $^{64}$Cu through metal chelator NOTA conjugated on the cysteine of pHLIP peptide (SEQ ID NO: 35). FIG. 3B show representative images of healthy mice vs. CLM mice administered with $^{18}$F-FDG and radioactive PRISM (carrying SEQ ID NO: 35) (n=5 mice per group). FIG. 3C show relative reporter concentrations measured in the urine of healthy mice vs. CLM mice after application of PRISM (n=5 mice per group; ±SEM; Student's t-test, two-tailed, ***P<0.001, *P<0.05). FIG. 3D show urinary reporters quantification and transverse images of tumor progression in CLM mice administered with radioactive PRISM over time (n=5 mice per group). FIG. 3E shows that the standard uptake value in the major organs as indicated were comparable against the conventional PET tracer. FIG. 3F shows that similar tumor versus liver ratios were observed in mice imaged with $^{18}$F-FDG and $^{64}$Cu-PRISM. FIG. 3G shows that the PRISM sensors were colocalized with abnormal physiologic conditions such as hypoxia. FIG. 3H shows that the majority of detected MMP9 protein expression overlapped with FAM-staining that marks PRISM sensors in the tumor, presumably bound to tissue section cells via membrane insertion of pHILP.

FIG. 4A shows a typical in vivo experimental time line. FIG. 4B shows histopathology staining of lung sections from MC26 injected tumor bearing mouse and control mouse injected with saline. FIG. 4C shows urinary reporter level quantified in tumor-beading and control mice as tumor progressed. FIG. 4D shows (i-ii) PET/CT images of healthy or mice with CRC lung metastasis visualized by $^{18}$F-FDG; (iii-iv) $^{64}$Cu-PRISM (carrying SEQ ID NO: 35). FIG. 4E shows relative SUV quantification of images in FIG. 4D. FIG. 4F shows relative SUV quantification of images in FIG. 4E. FIG. 4G shows relative SUV quantification of heart uptake in tumor bearing mice imaged with FDG and PRISM, respectively. FIG. 4H shows relative SUV quantification of lung/liver ratio in sham or tumor bearing mice imaged with PRISM. FIG. 4I shows IHC and immunofluorescence staining on tissue sections from tumor bearing mice. FIG. 4J shows the high-throughput cryofluorescence tomography on whole animals (healthy control or lung tumor-bearing) after systemic administration of PRISM sensors. The localization of FAM fluorescence signal exhibits a pattern that was perfectly aligned with corresponding anatomical tumors that had formed throughout the lung. FIG. 4K shows that PRISM sensors were largely colocalized with MMP9, which present at elevated levels in the lung tumors.

FIG. 5A shows a typical in vivo experimental time line. FIG. 5B shows relative reporter concentrations measured in the urine of CLM mice with or without 5-FU treatment (n=5 mice per group; ±SEM; Student's t-test, two-tailed, *P<0.001, **P<0.0001). FIGS. 5C-5F show representative images of CLM mice with or without 5-FU treatment imaged with radioactive PRISM (carrying SEQ ID NO: 35) at 2 (FIGS. 5C and 5E) or 4 weeks (FIGS. 5D and 5F) after tumor inoculation (n=5 mice per group). FIG. 5G shows quantification of metastasis/liver ratio, indicating tumor progression in CLM mice administered with radioactive PRISM (n=5 mice per group).

FIG. 6A shows a typical in vivo experimental time line. FIG. 6B shows relative reporter concentrations measured in the urine of tumor bearing mice with or without 5-FU treatment (n=5 mice per group; ±SEM; Student's t-test, two-tailed, *P<0.001, **P<0.0001). FIGS. 6C-6F show representative images of CLM mice with or without 5-FU treatment imaged with radioactive PRISM (carrying SEQ ID NO: 35) at 2 (FIGS. 6C and 6E) or 4 weeks (FIGS. 6D and 6F) after tumor inoculation (n=5 mice per group). FIG. 6G shows quantification of lung/liver ratio, indicating tumor progression in tumor bearing mice administered with radioactive PRISM (n=5 mice per group).

DETAILED DESCRIPTION

Figure 1:
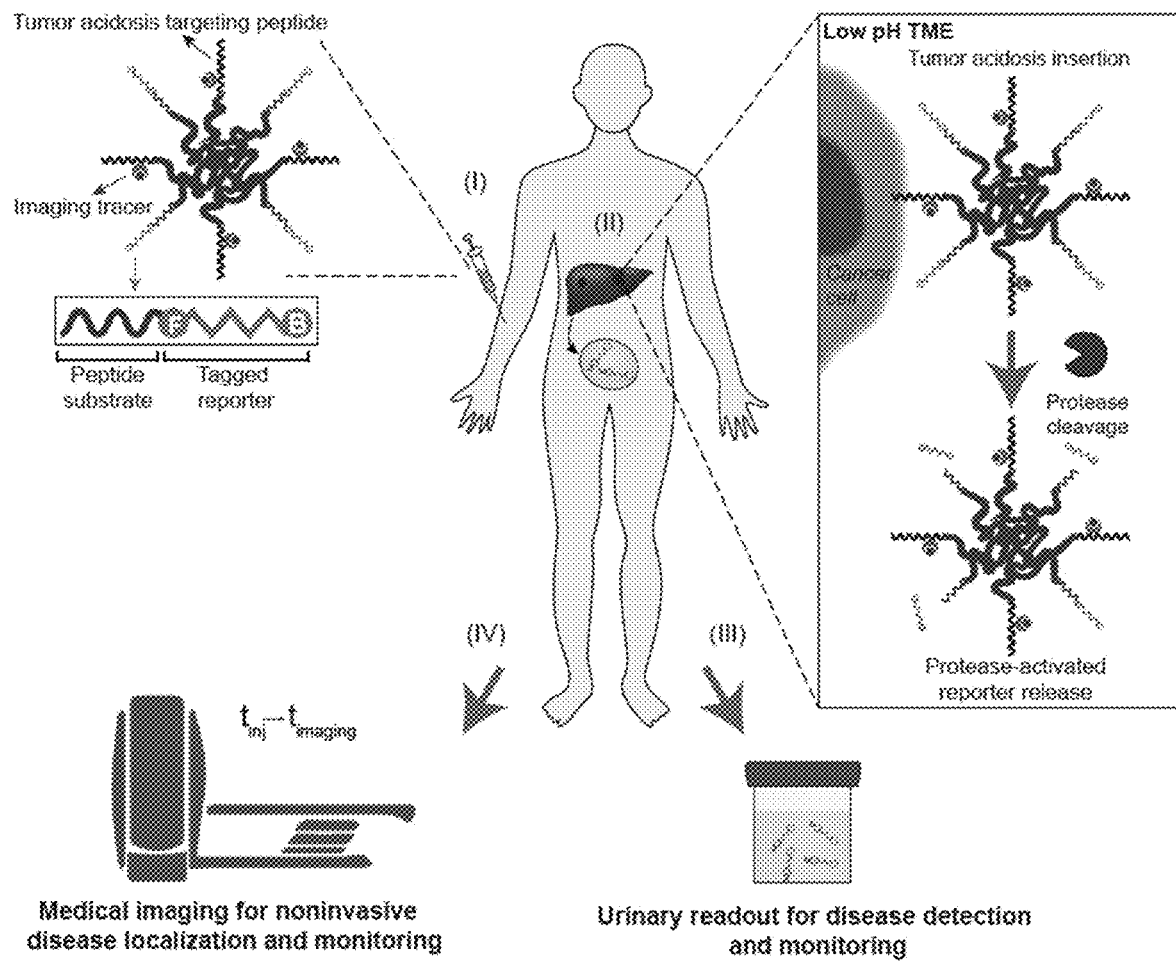
FIG. 1 shows protease-responsive imaging sensors for detection and imaging of cancer metastasis. PRISM (I) targets acidic TME. Activation of PRISM by metastasis-specific protease activity triggers (II) release of synthetic biomarker into urine for sensitive detection (III). Tumor insertion enables cancer specific imaging signal (IV).

The technology described herein allows for detection, including early detection and precise imaging of tumors. The present disclosure is based, at least in part, on the unexpected results demonstrating that a protease imaging sensor comprising (i) an enzyme-specific substrate with a first detectable marker that is capable of being released from the sensor upon exposure to an enzyme and (ii) a tumor imaging agent with a second detectable marker can be used to detect tumors with aberrant protease activity and localize to sites of metastasis in a noninvasive manner.

Reliable evidence of disseminated disease at the time of primary detection is consistent with a poor prognosis. For example, though hepatic resection is widely accepted as the optimal modality for potentially curing patients, only 10% of patients with CRC liver metastases at primary diagnosis are candidates for this intervention (Hess et al., Cancer. 2006 Apr. 1; 106(7):1624-33) Thus far, disseminated disease is still largely treated with 5-FU/Leucovorin, a standard chemotherapy which lacks curative potential due to inadequate access to sites of metastasis and emergence of resistance (Martini et al., World J Gastroenterol. 2017 Jul. 14; 23(26): 4675-4688). To increase the effectiveness of treatments, intensive surveillance protocols including medical imaging and monitoring for cancer biomarkers in blood are implemented following primary resection to detect early stage metastases (Tsikitis et al., J Clin Oncol. 2009 Aug. 1; 27(22):3671-6). However, the need for sensitive detection places a unique burden on the development of next-generation diagnostics. The small size, multiplicity, and low tumor-to-organ contrast of liver metastases render current imaging platforms (e.g. ultrasound, CT) relatively insensitive to early diseases (e.g., with standard CT scan, only 50% of 1-2 cm nodules are reliably detected, and nodules <5 mm are undetectable (Schima et al., Cancer Imaging. 2005 Nov. 23; 5 Spec No A:S149-56). Similar challenges exist for blood biomarker detection, where solid tumors could potentially remain undetectable for 10-12 years and reach spherical diameters >2.5 cm before blood biomarker levels can indicate the disease (Hori et al., Sci Transl Med. 2011 Nov. 16; 3(109):109ra116; Lutz et al., PLoS Med. 2008 Aug. 19; 5(8):e170). Moreover, inconsistencies between the mutation status estimated using blood versus tumor DNA samples also interfere with early detection and diagnosis. Beyond initial diagnosis, disease stratification is also critical to design a robust treatment strategy. Recently, for example, improvements in patient survival and reduced recurrence in CRC patients have been attributed to increased incidence of liver resection in a selected group of patients bearing a maximum four focal liver lesions (Tsikitis et al., J Clin Oncol. 2009 Aug. 1; 27(22):3671-6; Blesa et al., Curr Oncol. 2009 September; 16(5):76-80).

In some embodiments, the multi-functional protease imaging sensors integrate advances in nanoscale materials, tumor-insertion peptides, and synthetic biomarkers in order to treat metastases and sensitively detect their response beyond clinical thresholds. Unlike traditional shotgun proteomic methods which seek to identify biomarkers based on the abundance of proteins, the activity-based sensor (e.g., activity-based nanosensor, ABN) approach is based on the application of synthetic peptides to monitor protease activity. Thus, it circumvents challenges associated with shotgun methods including low target protein concentrations, low signal-to-noise ratios due to matrix complexity, and the need for rigorous protocol validation (Picotti et al., Nature methods 2012, 9, 555). In some embodiments, the protease imaging sensors comprise nanomaterial pharmacokinetics (e.g., urinary secretion) and bio-orthogonality (e.g., synthetic reporters not present in living systems). Without being bound by a particular theory, these degrees of precision are not readily amenable to endogenous biomarkers and may provide the ability to detect metastases earlier than clinically used diagnostics.

Furthermore, the key question in development of a novel therapy regimen, especially immunotherapies, remains whether it is possible to predict the outcome of therapy, based not only on the presence of cytotoxic T-cells but also on their interaction with and dynamic changes in the tumor microenvironment over time (Rashidian et al., The Journal of experimental medicine 2017, 214, 2243; Helfen et al., Journal of nuclear medicine: official publication, Society of Nuclear Medicine 2018, 59, 183). Standard PET imaging with metabolic tracers has been widely used to assess response to traditional therapy but is limited in cancer immunotherapy due to a lack of ability to accurately track changes in tumor microenvironment (TME) (Longo et al., Cancer research 2016, 76, 6463; Larimer et al., Cancer research 2017, 77, 2318). When immune cells infiltrate tumors, they can cause expansion of tumor volume or induce new detectable lesions that are indistinguishable from tumor progression (Rashidian et al., Proceedings of the National Academy of Sciences of the United States of America 2015, 112, 6146). As an extension of the methods described herein, without being bound by a particular theory, one could detect and track changes in TME noninvasively via pathologic acidosis targeting. Such level of precision would allow one to follow and visualize therapeutic responses longitudinally and also to predict outcomes. Patients may then be stratified into responders and non-responders during the course of immunotherapy, such that decisions to continue or terminate therapy might be refined in case of an equivocal response. This level of noninvasive monitoring could therefore change how therapies are applied and assessed, to the benefit of many patients.

The protease imaging sensors of the present disclosure address the foregoing challenges, in part, by allowing for robust tumor detection and providing precise localization of metastases in disseminated disease models that recapitulate important features of human disease. In some embodiments, when the first detectable marker is detected (e.g. in the urine), precise anatomical information such as size, shape, position of tumors, and their relationship with adjacent structures may be determined using the second detectable marker for clinical therapy response evaluation and treatment plan reaffirmation. The protease imaging sensors of the present disclosure may be useful in the sensitive detection of cancer metastases and in increasing efficacy of treatments. For example, in some embodiments, the protease imaging sensors harness metastasis-specific proteases as triggers to release urinary biomarkers for sensitive detection and imaging of tumor metastases.

Scaffolds

The protease imaging sensor (e.g., protease imaging sensor) comprises a modular structure having a scaffold linked to an enzyme-specific substrate that is attached to a first detectable marker and a tumor imaging agent. A modular structure, as used herein, refers to a molecule having multiple domains.

The scaffold may include a single type of substrate, such as, a single type of enzyme-specific substrate, or it may include multiple types of different substrates. For instance each scaffold may include a single (e.g., 1) type of substrate or it may include 2-1,000 different substrates, or any integer therebetween. Alternatively, each scaffold may include greater than 1,000 different substrates. Multiple copies of the protease imaging sensor are administered to the subject. In some embodiments, a composition comprising a plurality of different sensors may be administered to a subject to determine whether multiple enzymes and/or substrates are present. In that instance, the plurality of different sensors includes a plurality of first detectable markers, such that each substrate is associated with a first detectable marker.

The scaffold may serve as the core of the sensor. A purpose of the scaffold is to serve as a platform for the substrate and enhance delivery of the sensor to the subject. As such, the scaffold can be any material or size as long as it can enhance delivery and/or accumulation of the sensors to the subject. Preferably, the scaffold material is non-immunogenic, i.e. does not provoke an immune response in the body of the subject to which it will be administered. Non-limiting examples of scaffolds, include, for instance, compounds that cause active targeting to tissue, cells or molecules, microparticles, nanoparticles, aptamers, peptides (RGD, iRGD, LyP-1, CREKA, etc.), proteins, nucleic acids, polysaccharides, polymers, antibodies or antibody fragments (e.g., herceptin, cetuximab, panitumumab, etc.) and small molecules (e.g., erlotinib, gefitinib, sorafenib, etc.).

In some aspects, the disclosure relates to the discovery that delivery to a subject is enhanced by sensors having certain polymer scaffolds (e.g., poly(ethylene glycol) (PEG) scaffolds). Polyethylene glycol (PEG), also known as poly(oxyethylene) glycol, is a condensation polymer of ethylene oxide and water having the general chemical formula $HO(CH_2CH_2O)[n]H$. Generally, a PEG polymer can range in size from about 2 subunits (e.g., ethylene oxide molecules) to about 50,000 subunits (e.g., ethylene oxide molecules). In some embodiments, a PEG polymer comprises between 2 and 10,000 subunits (e.g., ethylene oxide molecules).

A PEG polymer can be linear or multi-armed (e.g., dendrimeric, branched geometry, star geometry, etc.). In some embodiments, a scaffold comprises a linear PEG polymer. In some embodiments, a scaffold comprises a multi-arm PEG polymer. In some embodiments, a multi-arm PEG polymer comprises between 2 and 20 arms. In some embodiments, a multi-arm PEG polymer comprises at least 1, 2, 3, 4, 5, 6, 7, 8, 9, 10, 15, 20, 30, 40, 50, 60, 70, 80, 90, or 100 arms. In some embodiments, a multi-arm PEG polymer comprises 8 arms. Multi-arm and dendrimeric scaffolds are generally described, for example by Madaan et al. *J Pharm Bioallied Sci.* 2014 6(3): 139-150.

Additional polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginnate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycolic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly (lactic-co-glycolic acid) (PLGA).

In some embodiments, a scaffold (e.g., a polymer scaffold, such as a PEG scaffold) has a molecular weight equal to or greater than 40 kDa. In some embodiments, a scaffold is a nanoparticle (e.g., an iron oxide nanoparticle, IONP) that is between 10 nm and 50 nm in diameter (e.g. having an average particle size between 10 nm and 50 nm, inclusive). In some embodiments, a scaffold is a high molecular weight protein, for example an Fc domain of an antibody.

As used herein the term "particle" includes nanoparticles as well as microparticles. Nanoparticles are defined as particles of less than 1.0 μm in diameter. A preparation of nanoparticles includes particles having an average particle size of less than 1.0 μm in diameter. Microparticles are particles of greater than 1.0 μm in diameter but less than 1 mm. A preparation of microparticles includes particles having an average particle size of greater than 1.0 μm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid, etc.), synthetic polymer materials (including poly-lactide-coglycolide, poly-glycerol sebacate, etc.), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide. A number of biodegradable and non-biodegradable biocompatible polymers are known in the field of polymeric biomaterials, controlled drug release and tissue engineering (see, for example, U.S. Pat. Nos. 6,123, 727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

The scaffold may be composed of inorganic materials. Inorganic materials include, for instance, magnetic materials, conductive materials, and semiconductor materials. In some embodiments, the scaffold is composed of an organic material.

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle. The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the scaffolds (e.g., based on the volume of the aqueous solution or other channel-forming reagent) or by microscopic inspection of the scaffolds post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The disclosure contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

Substrates

The enzyme-specific substrate is a portion of the modular structure that is connected to the scaffold. A substrate, as used herein, is the portion of the modular structure that promotes the enzymatic reaction in the subject, causing the release of a detectable marker. The substrate typically comprises an enzyme-sensitive portion (e.g., protease substrate) linked to a detectable marker.

The substrate is dependent on enzymes that are active in a specific disease state (e.g., cancer). For instance, tumors are associated with a specific set of enzymes. A sensor is designed with one or more substrates that match those of the enzymes expressed by the tumor, by the subject in response to the cancer or by other diseased tissue. Alternatively, the substrate may be associated with enzymes that are ordinarily present but are absent in a particular disease state. In this example, a disease state would be associated with a lack of signal associated with the enzyme, or reduced levels of signal compared to a normal reference.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

The substrate may be optimized to provide both high catalytic activity (or other enzymatic activity) for specified target enzymes but to also release optimized detectable markers for detection. Patient outcome depends on the phenotype of individual diseases at the molecular level, and this is often reflected in expression of enzymes. The recent explosion of bioinformatics has facilitated exploration of complex patterns of gene expression in human tissues (Fodor S. P. A., Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F, et al. Classification and diagnostic prediction of cancers using gene expression profiling and artificial neural networks. Nat Med 2001; 7:673-679.). This information can be accessed in order to identify enzymes and substrates associated with specific diseases. Based on this information the skilled artisan can identify appropriate enzyme or substrates to incorporate into the sensor.

In some embodiments, an enzyme-specific substrate comprises a substrate for a protease (e.g., an amino acid sequence that is cleaved by a protease). In some embodiments, the protease substrate is a substrate of a disease-associated enzyme. Examples of enzymes that are associated with disease in a subject include serine proteases, cysteine proteases, threonine proteases, aspartic proteases, glutamic proteases, metalloproteases, etc. Examples of substrates for disease-associated enzymes include but are not limited to SLKRYGGG (SEQ ID NO: 1; plasma kallikrein), AAF-RSRGA (SEQ ID NO: 2; kallikrein 1), xxFRFFxx (SEQ ID NO: 3; cathepsin B), QSVGFA (SEQ ID NO: 4; cathepsin B), LGLEGAD (SEQ ID NO: 5; cathepsin K), GPLD (SEQ ID NO: 6; subunit beta 1c), LGVLIV (SEQ ID NO: 7; cathepsin D), GLVLVA (SEQ ID NO: 8; cathepsin E), PAALVG (SEQ ID NO: 9; MMP2), GPAGLAG (SEQ ID NO: 10; MMP9), GGPLGVRGKK (SEQ ID NO: 11; MMP9), and GGfPRSGGGK (f=d-stereoisomer of phenylalanine; SEQ ID NO: 12; thrombin).

The enzyme-specific substrate may be optimized to provide both high catalytic activity (or other enzymatic activity) for specified target enzymes but to also release optimized detectable markers for detection. Patient outcome depends on the phenotype of individual diseases at the molecular level, and this is often reflected in expression of enzymes. The recent explosion of bioinformatics has facilitated exploration of complex patterns of gene expression in human tissues (Fodor, S. A. Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F, et al. Classification and diagnostic prediction of cancers using gene expression profiling and artificial neural networks. Nat Med 2001; 7:673-679.).

This information can be accessed in order to identify enzymes and substrates associated with specific diseases. Based on this information the skilled artisan can identify appropriate enzyme or substrates to incorporate into the pro-diagnostic reagent.

Table 1 provides a non-limiting list of enzymes associated with (either increased or decreased with respect to normal) disease, the type of substrate, and in some instances, the specific substrate. Table 2 provides a non-limiting list of substrates associated with disease or other conditions. Numerous other enzyme/substrate combinations associated with specific diseases or conditions are known to the skilled artisan and are useful according to the invention.

TABLE 1

Non-limiting examples of cancer-associated enzymes and substrates.

| Disease | Enzyme | Substrate |
| --- | --- | --- |
| Cancer | MMP | collagens, gelatin, various ECM proteins |
| Cancer | MMP-2 | type IV collagen and gelatin |
| Cancer | MMP-9 | type IV and V collagens and gelatin |
| Cancer | Kallikreins | kininogens, plasminogen |
| Cancer | Cathepsins | broad spectrum of substrates |
| Cancer | plasminogen activator, tPA | Plasminogen |
| Cancer | Urokinase-type plasminogen activator, uPA | Plasminogen |
| Cancer | ADAM (A Diseintegrin And Metalloprotease, also MDC, Adamalysin) | various extracellular domains of transmembrane proteins |
| Pancreatic carcinoma | MMP-7 | various, e.g. collagen 18, FasL, HLE, DCN, IGFBP-3, MAG, plasminogen, other MMPs |
| Pancreatic Cancer | ADAM9, ADAM15 | various extracellular domains of transmembrane proteins |
| Prostate adenocarcinoma | Matriptase, a type II transmembrane serine protease | unspecific, cleaves after Lys or Arg residues |
| Prostate cancer | Kallikrein 3 | kininogens, plasminogen |
| Prostate cancer | ADAM15 | various extracellular domains of transmembrane proteins |
| Ovarian carcinoma | Kallikrein 6 | kininogens, plasminogen |
| Epithelial-derived tumors (breast, prostate, ovarian, colon, oral) | Matriptase, a type II transmembrane serine protease | unspecific, cleaves after Lys or Arg residues |
| Ovarian Cancer | MMP-2, MMP-9, kallikrein-10 (hk-10) | type IV and V collagens and gelatin, kininogens, plasminogen |
| Breast, gastric, prostate cancer | cathepsins B, L and D | broad spectrum of substrates |
| Endometrial cancer | cathepsin B | unspecific cleavage of a broad spectrum of substrates without clear sequence specificity |
| esophageal adenocarcinoma | cathepsin B | unspecific cleavage of a broad spectrum of substrates without clear sequence specificity |

TABLE 1-continued

Non-limiting examples of cancer-associated enzymes and substrates.

| Disease | Enzyme | Substrate |
|---|---|---|
| Invasive cancers, metastases | type II integral serine proteases (dipeptidyl peptidase IV (DPP4/CD26), seprase/fibroblast activation protein alpha (FAPalpha) and related type II transmembrane prolyl serine peptidases)) | |
| Invasive cancers, metastases | Seprase | various ECM proteins |
| Viral Infections | | |
| All Retroviruses | viral protease | precursor GagPol fusion |
| HIV | HIV protease (HIV PR, an aspartic protease) | precursor Gag and GagPol proteins |
| Hepatitis C | NS3 serine protease | viral precursor polyprotein |
| Dengue | Dengue protease | autocleavage (NS2B/NS3), NS3/NS4A and NS4B/NS5 cleavage |
| West Nile | NS2B/NS3pro | viral precursor polyprotein |
| Bacterial Infections | | |
| *Legionella* spp. | zinc metalloprotease | Me-Arg-Pro-Tyr |
| Meningoencephalitis | histolytic cysteine protease | |
| *Streptococcus pyogenes* (Group A *Streptococcus*) | streptococcal pyrogenic exotoxin B (SpeB) | extracellular matrix, immunoglobulins, complement components |
| *Clostridium difficile* | Cwp84 | fibronectin, laminin, vitronectin and other ECM proteins |
| *Pseudomonas aeruginosa* | lasA | Leu-Gly-Gly-Gly-Ala |
| *Pseudomonas aeruginosa* | Large ExoProtease A | Cleavage of peptide ligands on PAR1, PAR2, PAR4 (Protease-activated receptor). See, e.g., Kida et al, Cell Microbiol. 2008 July; 10(7): 1491-504. |
| *Pseudomonas aeruginosa* | protease IV | complement factors, fibrinogen, plasminogen (See, e.g., Engel et al., J Biol Chem. 1998 July. 3; 273(27): 16792-7). |
| *Pseudomonas aeruginosa* | alkaline protease | Complement factor C2 (See, e.g., Laarman et al., J Immunol. 2012 January 1; 188(1): 386-93). |
| Additional Diseases | | |
| Alzheimer's disease | BACE-1,2 (Alzheimer secretase) | β-amyloid precursor protein |
| Stroke and recovery | MMP, tPA | |
| cardiovascular disease | Angiotensin Converting Enzyme (ACE) | angiotensin I, bradykinin |
| Atherosclerosis | cathepsin K, L, S | broad spectrum of substrates |
| arthritis | MMP-1 | triple-helical fibrillar collagens |
| rheumatoid arthritis | thrombin | Osteopontin |
| Malaria | SUB1 | KITAQDDEES |
| osteoarthritis | thrombin | Osteopontin |
| osteoporosis/osteoarthritis | cathepsin K, S | broad spectrum of substrates |
| Arthritis, inflammatory joint disease | Aggrecanase (ADAMTS4, ADAMTS11) | aggrecans (proteoglycans) |
| thrombosis | factor Xa (thrombokinase) | Prothrombin |
| thrombosis | ADAMTS13 | von Willebrand factor (vWF) |

TABLE 1-continued

Non-limiting examples of cancer-associated enzymes and substrates.

| Disease | Enzyme | Substrate |
| --- | --- | --- |
| thrombosis | plasminogen activator, tPA | Plasminogen |
| Stress-induced Renal pressure natriuresis | Prostasin | epithelial Na channel subunits |

TABLE 2

Non-limiting examples of substrates associated with disease and other conditions.

| DISEASE | TARGET SUBSTRATE | ENZYME |
| --- | --- | --- |
| Inflammation | Interleukin 1 beta | MMP-2, MMP-3, MMP-9, Trypsin, chymotrypsin, pepsin, Lys-C, Glu-C, Asp-N, Arg-C |
| Pituitary gland dysfunction, abnormal bone density, growth disorders | IGFBP-3 | MMP-1, MMP-3, MMP-9, Trypsin, chymotrypsin, pepsin, Lys-C, Glu-C, Asp-N, Arg-C |
| Cancer | TGF-beta | MMP-9, Trypsin, chymotrypsin, pepsin, Lys-C, Glu-C, Asp-N, Arg-C |
| Cancer, autoimmune disease | TNF | MMP-7, Trypsin, chymotrypsin, pepsin, Lys-C, Glu-C, Asp-N, Arg-C |
| Cancer, autoimmune disease | FASL | MMP-7, Trypsin, chymotrypsin, pepsin, Lys-C, Glu-C, Asp-N, Arg-C |
| Wound healing, cardiac disease | HB-EGF | MMP-3, Trypsin, chymotrypsin, pepsin, Lys-C, Glu-C, Asp-N, Arg-C |
| Pfeiffer syndrome | FGFR1 | MMP-2, Trypsin, chymotrypsin, pepsin, Lys-C, Glu-C, Asp-N, Arg-C |
| Cancer | Decorin | MMP-2, MMP-3, MMP-7, Trypsin, chymotrypsin, pepsin, Lys-C, Glu-C, Asp-N, Arg-C |
| Cancer | Tumor associated carbohydrate antigens | Endoglycosidases |
| Cancer | Sialyl Lewis$^a$ | O-glycanase |
| Cancer | Sialyl Lewis$^X$ | O-glycanase |
| Cancer/Rheumatoid Arthritis, pulmonary hypertension | VEGF | Trypsin, chymotrypsin, pepsin, Lys-C, Glu-C, Asp-N, Arg-C |
| Cancer | EGF | Trypsin, chymotrypsin, pepsin, Lys-C, Glu-C, Asp-N, Arg-C |
| Cancer | IL2 | Trypsin, chymotrypsin, pepsin, Lys-C, Glu-C, Asp-N, Arg-C |
| Cancer inflammation/angiogenesis | IL6 | Trypsin, chymotrypsin, pepsin, Lys-C, Glu-C, Asp-N, Arg-C |
| Cancer | IFN-γ | Trypsin, chymotrypsin, pepsin, Lys-C, Glu-C, Asp-N, Arg-C |
| Cancer inflammation/angiogenesis, Rheumatoid Arthritis | TNF-α | Trypsin, chymotrypsin, pepsin, Lys-C, Glu-C, Asp-N, Arg-C |
| Cancer, Pulmonary fibrosis, Asthma | TGF-β | Trypsin, chymotrypsin, pepsin, Lys-C, Glu-C, Asp-N, Arg-C |
| Cancer, Pulmonary hypertension | PDGF | Trypsin, chymotrypsin, pepsin, Lys-C, Glu-C, Asp-N, Arg-C |
| Cancer, pulmonary cystadenoma | Fibroblast growth factor (FGF) | Trypsin, chymotrypsin, pepsin, Lys-C, Glu-C, Asp-N, Arg-C |
| Cancer | Brain-derived neurotrophic factor (BDNF) | Trypsin, chymotrypsin, pepsin, Lys-C, Glu-C, Asp-N, Arg-C |
| Cancer | Interferon regulatory factors (IRF-1, IRF-2) | Trypsin, chymotrypsin, pepsin, Lys-C, Glu-C, Asp-N, Arg-C |
| Inhibitor of tumor suppressors | MIF | Trypsin, chymotrypsin, pepsin, Lys-C, Glu-C, Asp-N, Arg-C |
| Lymphomas/carcinomas, alveolar proteinosis | GM-CSF | Trypsin, chymotrypsin, pepsin, Lys-C, Glu-C, Asp-N, Arg-C |
| Cancer invasion | M-CSF | Trypsin, chymotrypsin, pepsin, Lys-C, Glu-C, Asp-N, Arg-C |
| Chemical carcinogenesis, multiple sclerosis, rheumatoid arthritis, Crohn's disease | IL-12 | Trypsin, chymotrypsin, pepsin, Lys-C, Glu-C, Asp-N, Arg-C |

TABLE 2-continued

Non-limiting examples of substrates associated with disease and other conditions.

| DISEASE | TARGET SUBSTRATE | ENZYME |
| --- | --- | --- |
| Natural Killer T cell leukemias, inflammatory bowel disease, rheumatoid arthritis | IL-15 | Trypsin, chymotrypsin, pepsin, Lys-C, Glu-C, Asp-N, Arg-C |
| Cirrhosis | Tissue inhibitor of MMPs (TIMPs) | Trypsin, chymotrypsin, pepsin, Lys-C, Glu-C, Asp-N, Arg-C |
| Cirrhosis | Collagen I, III | MMP-1, MMP-8, Trypsin, chymotrypsin, pepsin, Lys-C, Glu-C, Asp-N, Arg-C |
| Cirrhosis | Collagen IV, V | MMP-2, Trypsin, chymotrypsin, pepsin, Lys-C, Glu-C, Asp-N, Arg-C |

Non-limiting examples of enzyme cleavable linkers may also be found in WO2010/101628, entitled METHODS AND PRODUCTS FOR IN VIVO ENZYME PROFILING, which was filed on Mar. 2, 2010.

In some embodiments, the enzyme-specific substrate is a cancer substrate. As used herein, "cancer substrate" refers to a substrate that is capable of being cleaved by a protease that is present (or upregulated) in a subject having a cancer (e.g., a malignant tumor, metastatic cancer, etc.). For example, certain cancers (e.g. metastatic cancers) are associated with upregulation of specific enzymes (e.g. ADAM28, MMP9, MMP12, ACE, C2, ADAMTS5, HTRA4, MMP16, MMP1, MMP3, MMP4, MMP7, MMP8, Cathepsin B, Cathepsin L, Cathepsin S, ADAM10, ADAM12, PRSS3, uPA, etc.). In some embodiments, the cancer substrate is a cancer metastasis substrate. In some embodiments, the cancer is colorectal cancer (e.g., CRC).

A substrate may be attached directly to the scaffold. For instance it may be coated directly on the surface of microparticles using known techniques, or chemically bonded to a polymeric scaffold, such as a PEG scaffold (e.g., via a peptide bond). Additionally, the substrate may be connected to the scaffold through the use of a linker. As used herein "linked" or "linkage" means two entities are bound to one another by any physicochemical means. Any linkage known to those of ordinary skill in the art, covalent or non-covalent, is embraced. Thus, in some embodiments the scaffold has a linker attached to an external surface, which can be used to link the substrate. Another molecule can also be attached to the linker. In some embodiments, two molecules are linked using a transpeptidase, for example, Sortase A.

The substrate is preferably a polymer made up of a plurality of chemical units. A "chemical unit" as used herein is a building block or monomer which may be linked directly or indirectly to other building blocks or monomers to form a polymer (e.g., a multi-arm PEG scaffold).

Detectable Markers

A protease imaging sensor of the present disclosure comprises (i) a first detectable marker that is attached to an enzyme-specific substrate and (ii) a tumor imaging agent comprising a second detectable marker. Any of the detectable markers described herein may be capable of being released from the protease imaging when exposed to an enzyme (e.g., exposed to an in vivo or in vitro). In some embodiments, the first detectable marker is capable of being released from the sensor when exposed to an enzyme (e.g., exposed to an in vivo or in vitro). In some embodiments, at least one of the detectable markers on the protease imaging sensor is not capable of being released from the protease imaging sensor when exposed to an enzyme (e.g., exposed to an in vivo or in vitro). In some embodiments, the second detectable marker is not capable of being released from the protease imaging sensor when exposed to an enzyme (e.g., exposed to an in vivo or in vitro). In certain embodiments, a protease imaging sensor comprises (i) a scaffold linked to an enzyme-specific substrate that is attached to a first detectable marker and the first detectable marker is capable of being released from the sensor when exposed to an enzyme and (ii) a tumor imaging agent comprising a second detectable marker, the tumor imaging agent is linked to the scaffold, and the second detectable marker is not capable of being released from the protease imaging sensor when exposed to an enzyme. In some embodiments, the tumor imaging agent does not include a cell penetrating domain.

A detectable marker once released is free to travel to a remote site for detection. A remote site is used herein to refer to a site in the body that is distinct from the bodily tissue housing the enzyme where the enzymatic reaction occurs. In some embodiments, the bodily tissue housing the enzyme where the enzymatic reaction occurs is disease tissue (e.g., tumor tissue). For example, the bodily tissue housing the enzyme where the enzymatic reaction occurs may be a site of a primary cancer or may be a site of a metastasis. Sites of metastasis may vary with the type of cancer. Non-limiting sites of metastasis for various cancer types are provided in Table 3 (see, e.g., National Cancer Institute's description of metastatic cancer).

TABLE 3

Non-limiting sites of metastasis by cancer type.

| Cancer Type | Sites of Metastasis |
| --- | --- |
| Bladder | Bone, liver, lung |
| Breast | Bone, brain, liver, lung |
| Colon | Liver, lung, peritoneum |
| Kidney | Adrenal gland, bone, brain, liver, lung |
| Lung | Adrenal gland, bone, brain, liver, other lung |
| Melanoma | Bone, brain, liver, lung, skin, muscle |
| Ovary | Liver, lung, peritoneum |
| Pancreas | Liver, lung, peritoneum |
| Prostate | Adrenal gland, bone, liver, lung |
| Rectal | Liver, lung, peritoneum |
| Stomach | Liver, lung, peritoneum |
| Thyroid | Bone, liver, lung |
| Uterus | Bone, liver, lung, peritoneum, vagina |

Modification of the protease-specific substrate by an enzyme in vivo, results in the production of a first detectable marker (e.g., release or decoupling of the detectable marker from the scaffold upon cleavage of the protease-specific substrate by an enzyme). Any of the detectable markers described herein is a detectable molecule. A detectable marker can be part of the substrate, e.g. the piece that is released or added upon cleavage or it can be a separate entity. In some embodiments, a detectable marker is composed of two ligands joined by a linker (e.g., a fluorescence resonance energy transfer (FRET) pair). A detectable marker may be comprised of, for instance one or more of a peptide, nucleic acid, small molecule, fluorophore/quencher, carbohydrate, particle, radiolabel, MRI-active compound, inorganic material, or organic material, with encoded characteristics to facilitate optimal detection, or any combination thereof. In some embodiments, the detectable marker comprises a GluFib peptide (SEQ ID NO: 13; EGVNDNEEGFFSAR) conjugated to a capture ligand and/or a fluorophore (e.g., a GluFib peptide flanked by a capture ligand, such as biotin, and a fluorophore, such as FAM).

In some embodiments, a substrate comprises a capture ligand, which is a molecule that is capable of being captured by a binding partner. The detection ligand is a molecule that is capable of being detected by any of a variety of methods. While the capture ligand and the detection ligand will be distinct from one another in a particular detectable marker, the class of molecules that make us capture and detection ligands overlap significantly. For instance, many molecules are capable of being captured and detected. In some instances these molecules may be detected by being captured or capturing a probe. The capture and detection ligand each independently may be one or more of the following: a protein, a peptide, a polysaccharide, a nucleic acid, a fluorescent molecule, or a small molecule, for example. In some embodiments the detection ligand or the capture ligand may be, but is not limited to, one of the following: Alexa488, TAMRA, DNP, fluorescein, OREGON GREEN® (4-(2,7-difluoro-6-hydroxy-3-oxo-3H-xanthen-9-YL)isophthalic acid), TEXAS RED® (sulforhodamine 101 acid chloride), Dansyl, BODIPY® (boron-dipyrromethene), Alexa405, CASCADE BLUE® (Acetic acid, [(3,6,8-trisulfo-1-pyrenyl)oxy]-, 1-hydrazide, trisodium salt), Lucifer Yellow, Nitrotyrosine, HA-tag, FLAG-tag, His-tag, Myc-tag, V5-tag, S-tag, biotin or streptavidin.

In some embodiments, the capture ligand and a detection ligand are connected by a linker. The purpose of the linker is prevent steric hindrance between the two ligands. Thus, the linker may be any type of molecule that achieves this. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib (SEQ ID NO: 13; EGVNDNEEGFFSAR). Optionally, the linker may be 8 nm-100 nm, 6 nm-100 nm, 8 nm-80 nm, 10 nm-100 nm, 13 nm-100 nm, 15 nm-50 nm, or 10 nm-50 nm in length.

In some embodiments, a detectable marker is a ligand encoded reporter. Without wishing to be bound by any particular theory, a ligand encoded reporter binds to a target molecule (e.g., a target molecule present in a tumor), allowing for detection of the target molecule at a site remote from where the ligand encoded reporter bound to the target (e.g., at a sight remote from a tumor).

In some embodiments, a detectable marker is a mass encoded reporter, for example an iCORE as described in WO2012/125808, filed Mar. 15, 2012, the entire contents of which are incorporated herein by reference. Upon arrival in the diseased microenvironment, the iCORE agents interface with aberrantly active proteases to direct the cleavage and release of surface-conjugated, mass-encoded peptide substrates into host urine for detection by mass spectrometry (MS) as synthetic biomarkers of disease.

A detectable marker may be detected by any known detection methods to achieve the capture/detection step. A variety of methods may be used, depending on the nature of the detectable marker. Detectable markers may be directly detected, following capture, through optical density, radioactive emissions, non-radiative energy transfers, or detectable markers may be indirectly detected with antibody conjugates, affinity columns, streptavidin-biotin conjugates, PCR analysis, DNA microarray, optical imaging, magnetic resonance (MR) imaging, positron emission tomography (PET) imaging, intraoperative imaging, and fluorescence analysis.

A capture assay, in some embodiments, involves a detection step selected from the group consisting of an ELISA, including fluorescent, colorimetric, bioluminescent and chemiluminescent ELISAs, a paper test strip or lateral flow assay (LFA), bead-based fluorescent assay, and label-free detection, such as surface plasmon resonance (SPR). The capture assay may involve, for instance, binding of the capture ligand to an affinity agent.

The analysis (e.g., detecting) step may be performed directly on a biological sample (e.g., urine sample, blood sample, tissue sample, etc.) or the signature component may be purified to some degree first. For instance, a purification step may involve isolating the detectable marker from other components in a biological sample (e.g., urine sample, blood sample, tissue sample, etc.). Purification steps include methods such as affinity chromatography. As used herein an "isolated molecule" or "purified molecule" is a detectable marker that is isolated to some extent from its natural environment. The isolated or purified molecule need not be 100% pure or even substantially pure prior to analysis.

The methods for analyzing detectable markers by identifying the presence of a detectable marker may be used to provide a qualitative assessment of the molecule (e.g., whether the detectable marker is present or absent) or a quantitative assessment (e.g., the amount of detectable marker present to indicate a comparative activity level of the enzymes). The quantitative value may be calculated by any means, such as, by determining the percent relative amount of each fraction present in the sample. Methods for making these types of calculations are known in the art.

A detectable marker described herein may be labeled. For example, a label may be added directly to a nucleic acid when the isolated detectable marker is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidites such as fluoreprime (Pharmacia, Piscataway, NJ), fluoredite (Millipore, Bedford, MA), FAM (ABI, Foster City, CA), rhodamine, polymethadine dye derivative, phosphores, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination (e.g., "multiplexed"). Radionuclides such as $^3$H, $^{125}$I, $^{35}$S, $^{14}$C, or $^{32}$P are also useful labels according to the methods of the invention. A plurality of radioactively distinguishable radionuclides can be used. Such radionuclides can be distinguished, for example, based on the type of radiation (e.g. α, β, or δ radiation) emitted by the radionuclides. The $^{32}$P signal can be detected using a phosphoimager, which currently has a resolution of approximately 50 microns. Other known techniques, such as chemiluminescence or colormetric (enzymatic color reaction), can also be used.

Detectable markers also include diagnostic and imaging labels (e.g., radiolabels). For example, a detectable marker may be detectable by positron emission tomography or computerized tomography. Non-limiting examples of detectable markers include detectable markers that are suitable for in vivo imaging, which include magnetic resonance imaging (MRI): Gd(DOTA); for nuclear medicine: $^{201}$Tl, gamma-emitting radionuclide $^{99m}$Tc; for positron-emission tomography (PET): positron-emitting isotopes, $^{18}$F-2-deoxyfluoroglucose (FDG), (18)F-fluoride, copper-64 ($^{64}$Cu), gadodiamide, and radioisotopes of Pb(II) such as $^{203}$Pb; $^{111}$In; and $^{89}$Zr.

In some embodiments, a detectable marker comprises a metal chelator (e.g., 1,4,7-Triazacyclononane-1,4,7-triacetic acid (NOTA), 1,4,7,10-tetraazacyclododecane-N,N',N'',N'''-tetraacetic acid (DOTA), Diethylenetriaminepentaacetic Anhydride (DTPA), 1,4,8,11-tetraazacyclotetradecane-1,4,8,11-tetraacetic acid (TETA), and/or deferoxamine (e.g., for $^{89}$Zr).

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET). Cleavage of the peptide results in separation of the chromophore and fluorophore, removal of the quench, and generation of a subsequent signal measured from the donor fluorophore.

Tumor Imaging Agent

The tumor imaging agent (e.g., a tumor imaging agent) of the present disclosure comprise a detectable marker and allow for localization of tumor cells. The tumor imaging agents may be capable of associating (e.g., binding) with a target tissue.

In some embodiments, the tumor imaging agent does not include a cell penetrating domain. As used herein, a cell penetrating domain is an agent (e.g., peptide sequence or a non-peptide) that promotes cellular uptake of itself and any conjugated cargo. Non-limiting examples of cell penetrating domains include protein transduction domains (e.g., TAT and penetratin), primary amphipathic cell penetrating peptides, secondary amphipathic cell penetrating peptides, and nonamphipathic cell penetrating peptides. See, e.g., Madani et al., J Biophys. 2011; 2011: 414729.

In some embodiments, the tumor imaging agent comprises a tumor insertion agent, which allows for localization of the tumor imaging agent to a tumor (e.g., a tumor vivo). Non-limiting examples of tumor insertion agents include pH low insertion peptides. pH low insertion peptides are capable of inserting across a lipid bilayer at a low or acidic pH, but do not insert into a lipid bilayer at neutral or basic pH. In some embodiments, a low pH is a pH that is a pH value that is less than 7, less than 6, less than 5, less than 4, less than 3, less than 2 or less than 1. In some embodiments, a neutral pH is a pH value of about 7. In some embodiments, a basic pH is a pH value that is higher than 7, higher than 8, higher than 9, higher than 10, higher than 11, higher than 12, higher than 13 or higher than 14.

The tumor imaging agents of the present disclosure may comprise an amino acid sequence set forth in Table 4 and/or Table 5. In some embodiments, a tumor imaging agent comprises a sequence that is at least 70% (e.g., at least 75%, 80%, 85%, 90%, 95%, 98%, 99%, or 100%) identical to a sequence set forth in Table 4 and/or Table 5.

In some embodiments, a pH low insertion peptide may comprise D-form amino acids, an azide side chain (N3), and/or cyanine (Cy7).

In certain embodiments, a pH low insertion peptide may comprise the amino acid sequence WKK. In certain embodiments, the tryptophan in the amino acid sequence WKK is a D-amino acid. In certain embodiments, all amino acids in the WKK sequence are D-amino acids. In certain embodiments, all amino acids in the WKK sequence are L-amino acids. In certain embodiments, the lysines in the WKK sequence are D-amino acids. In certain embodiments, the tryptophan in the amino acid sequence WKK is a L-amino acid, while the lysines are D-amino acids.

TABLE 4

Non-limiting examples of pH low insertion peptide sequences.

| Sequence | SEQ ID NO: |
|---|---|
| ACEQNPIYWARYADWLFTTPLLLLDLALLVDADEGT | 14 |
| ACEDQNPYWARYADWLFTTPLLLLDLALLVDG | 15 |
| ACEDQNPYWRAYADLFTPLTLLDLLALWDG | 16 |
| ACDDQNPWRAYLDLLFPTDTLLLDLLW | 17 |
| ACEEQNPWRAYLELLFPTETLLLELLW | 18 |
| ACDDQNPWARYLDWLFPTDTLLLDL | 19 |
| CDNNNPWRAYLDLLFPTDTLLLDW | 20 |
| ACEEQNPWARYLEWLFPTETLLLEL | 21 |
| CEEQQPWAQYLELLFPTETLLLEW | 22 |
| CEEQQPWRAYLELLFPTETLLLEW | 23 |
| ACEDQNPWARYADWLFPTTLLLLD | 24 |
| ACEEQNPWARYAEWLFPTTLLLLE | 25 |
| ACEDQNPWARYADLLFPTTLAW | 26 |
| ACEEQNPWARYAELLFPTTLAW | 27 |
| Ac-TEDADVLLALDLLLLPTTFLWDAYRAWYPNQECA-Am | 28 |
| CDDDDDNPNYWARYANWLFTTPLLLLNGALLVEAEET | 29 |
| CDDDDDNPNYWARYAPWLFTTPLLLLPGALLVEAEET | 30 |

A tumor imaging agent may comprise a tumor targeting agent may be conjugated (e.g., N-terminally conjugated or C-terminally conjugated) to a detectable marker (e.g., including a fluorophore, radiolabel, or any combination thereof). In some embodiments, a tumor imaging agent comprises a detectable marker and a tumor insertion agent (e.g., a pH low insertion peptide). The tumor insertion agent may comprises two ends (e.g., a N-terminus and a C-terminus). In certain embodiments, the tumor insertion agent is conjugated to a detectable marker (e.g., a fluorophore or a radiolabel) on one end and is conjugated to a scaffold (e.g., a scaffold comprising polyethylene glycol) on the other end. Non-limiting methods of conjugation include click chemistry. See, e.g., Thirumurugan et al., Chem Rev. 2013 Jul. 10; 113(7):4905-79.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin avidin and biotin streptavidin complexation and other affinity interactions. Such means and methods of attachment are well known to those of ordinary skill in the art.

Methods to Detect Enzyme Activity

Aspects of the disclosure relate to the surprising discovery that sensors comprising a tumor imaging agent and an enzyme-specific substrate attached to a detectable marker are useful for detecting enzyme activity (e.g., in vitro and in vivo).

In some embodiments, detection of a detectable marker that has been released from the sensor in a biological sample (e.g., in vitro or in vivo) is indicative of enzyme (e.g., cancer-associated enzyme) activity. In some embodiments, detection of a detectable marker that is part of the tumor imaging agent indicates the site of exposure to the enzyme (e.g., cancer-associated enzyme).

As used herein, a biological sample is a tissue sample (such as a blood sample, a hard tissue sample, a soft tissue sample, etc.), a urine sample, mucous sample, saliva sample, fecal sample, seminal fluid sample, cerebrospinal fluid sample, etc. In preferred embodiments, the biological sample is a tissue sample. The tissue sample may be obtained from any tissue of the subject, including brain, lymph node, breast, liver, pancreas, colon, liver, lung, blood, skin, ovary, prostate, kidney, or bladder. The tissue from which the biological sample is obtained may be healthy or diseased. In some embodiments, a tissue sample comprises tumor cells or a tumor.

A tissue sample for use in methods described by the disclosure may be unmodified (e.g., not treated with any fixative, preservative, cross-linking agent, etc.) or physically or chemically modified. Examples of fixatives include aldehydes (e.g., formaldehyde, formalin, gluteraldehyde, etc.), alcohols (e.g., ethanol, methanol, acetone, etc.), and oxidizing agents (e.g., osmium tetroxide, potassium dichromate, chromic acid, potassium permanganate, etc.). In some embodiments, a tissue sample is cryopreserved (e.g., frozen). In some embodiments, a tissue sample is embedded in paraffin.

Methods for Detecting a Tumor in a Subject

In some aspects, the disclosure provides methods for a tumor in a subject. The subject may be suspected of having a tumor, at risk for having a tumor, or has a tumor. As used herein, a subject is a human, non-human primate, cow, horse, pig, sheep, goat, dog, cat, or rodent. In all embodiments human subjects are preferred. In aspects of the invention pertaining to disease diagnosis in general the subject preferably is a human suspected of having a disease, or a human having been previously diagnosed as having a disease. Methods for identifying subjects suspected of having a disease may include physical examination, subject's family medical history, subject's medical history, biopsy, or a number of imaging technologies such as ultrasonography, computed tomography, magnetic resonance imaging, magnetic resonance spectroscopy, or positron emission tomography.

In some embodiments, methods described by the disclosure result in identification (e.g., detection) of a disease in a subject prior to the onset of symptoms. In some embodiments, a tumor that is less than 1 cm, less than 0.5 cm, or less than 0.005 cm is detected using methods described by the disclosure. In some embodiments, the tumor that is detected is between 1 mm and 5 mm in diameter (e.g., about 1 mm, 2 mm, 3 mm, 4 mm, or about 5 mm) in diameter.

In some embodiments, the presence of enzyme activity (e.g., protease activity) in a subject is identified by obtaining a biological sample from a subject that has been administered a sensor as described by the disclosure and detecting the presence of a detectable marker in the biological sample. Generally, the biological sample may be a tissue sample (such as a blood sample, a hard tissue sample, a soft tissue sample, etc.), a urine sample, saliva sample, fecal sample, seminal fluid sample, cerebrospinal fluid sample, etc. In some embodiments, detection of a detectable marker (e.g., a detectable marker that was released from a sensor) is indicative of the subject having a tumor.

In some embodiments, the site of exposure to an enzyme (e.g., cancer-associated enzyme) is identified by detecting the detectable marker from the tumor imaging agent in a subject that has been administered a sensor as described by the present disclosure.

In some embodiments, the methods described herein comprise detecting at least one detectable marker. In some embodiments, the detectable marker that has been released from an enzyme-specific substrate is detected. In some embodiments, the detectable marker that is part of the tumor imaging agent is detected. In some embodiments, at least two detectable markers are detected. For example, a detectable marker may be detected in a biological sample (e.g., a detectable marker that has been released from a sensor) and a detectable marker may be detected in situ in a subject that has been administered the sensor. Any suitable method may be used to detect any of the detectable markers described herein, including fluorescence analysis, optical imaging, magnetic resonance imaging (MRI), positron emission tomography (PET) imaging, computerized tomography (CT) imaging, intraoperative imaging, or any combination thereof.

Detection of one or more detectable markers in the biological sample may be indicative of a subject having a cancer (e.g., colorectal cancer). In some instances, detection of one or more detectable markers in the biological sample is indicative of a specific stage of a disease (e.g., metastatic or non-metastatic). In some embodiments, detection of one or more detectable markers in the biological sample is indicative of a type of cancer.

Detection of one or more detectable markers in vivo in a subject (e.g., detection of a tumor imaging agent) may be indicative of whether a subject has metastatic or non-metastatic cancer.

Detection of one or more detectable markers in a biological sample from a subject administered a sensor of the present disclosure, in situ in a subject administered a sensor of the present disclosure, or any combination thereof may be used to monitor tumor progression in the subject. To practice this embodiment, one or more detectable markers is detected more than one time (e.g., at least 2, 3, 4, 5, 6, 7, 8, 9, 10, 15, 20, 30, 40, 50, 60, 70, 80, 90, or at least 100 times). In certain embodiments, the subject has been administered a first therapeutic agent, a first therapeutic intervention has been performed on the subject, or a combination thereof.

The methods of the present disclosure may further comprise continuing or modifying a subject's course of treatment (e.g., administering a second therapeutic agent, administering a different therapeutic agent, administering a first therapeutic agent, performing a therapeutic intervention, or stopping treatment) after detection one or more detectable markers. In some embodiments, lack of detection of a detectable marker over time is indicative of a subject no longer having a cancer (e.g., type of cancer or stage of cancer) and treatment may be modified or discontinued.

In certain embodiments, an increase the amount of a detectable marker (e.g., increase by at least 5%, 10%, 20%, 30%, 40%, 50%, 60%, 70%, 80%, 90%, 100%, 200%, 300%, 400%, 500%, 600%, 700%, 800%, 900%, or 1000%) detected in a subsequent biological sample (e.g., a tissue sample (such as a blood sample, a hard tissue sample, a soft tissue sample, etc.), a urine sample, mucous sample, saliva sample, fecal sample, seminal fluid sample, or cerebrospinal fluid sample) from a subject administered a sensor of the present disclosure compared to one or more previous samples from the subject indicates that a tumor is progressing. In certain embodiments, a similar amount of a detectable marker (e.g., no change in the amount, or a change (increase or decrease) of 1-5%) detected in a subsequent biological sample (e.g., a tissue sample (such as a blood sample, a hard tissue sample, a soft tissue sample, etc.), a urine sample, mucous sample, saliva sample, fecal sample, seminal fluid sample, or cerebrospinal fluid sample) from a subject administered a sensor of the present disclosure compared to one or more previous samples from the subject indicates that a tumor is stable. In certain embodiments, a decrease the amount of a detectable marker (e.g., increase by at least 5%, 10%, 20%, 30%, 40%, 50%, 60%, 70%, 80%, 90%, 100%, 200%, 300%, 400%, 500%, 600%, 700%, 800%, 900%, or 1000%) detected in a subsequent biological sample (e.g., a tissue sample (such as a blood sample, a hard tissue sample, a soft tissue sample, etc.), a urine sample, mucous sample, saliva sample, fecal sample, seminal fluid sample, or cerebrospinal fluid sample) from a subject administered a sensor of the present disclosure compared to one or more previous samples from the subject indicates that a tumor is in remission.

Without being bound by a particular theory, a protease imaging sensor comprising a tumor imaging peptide with a detectable marker (e.g., a tracer) may produce a low signal when not localized to a cell (e.g., in the absence of a tumor), but produce a high signal that is detectable when localized to a cell (e.g., in the presence of a tumor).

Administration

Compositions comprising any of the sensors described herein can be administered to any suitable subject. In some embodiments, the sensors of the disclosure are administered to the subject in an effective amount for detecting a tumor (e.g., a primary tumor, a metastatic tumor, or a combination thereof). An "effective amount", for instance, is an amount necessary or sufficient to cause release of a detectable marker in the presence of an enzyme, detection of a tumor in situ, or a combination thereof. The effective amount of an sensor of the present disclosure described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Aspects of the disclosure relate to systemic administration of an sensor to a subject. In some embodiments, the systemic administration is injection, optionally subcutaneous injection. The sensors of the present disclosure may also be administered through any suitable routes. For instance, the compounds of the present invention can be administered intravenously, intradermally, intratracheally, intraarterially, intralesionally, intratumorally, intracranially, intraarticularly, intraprostaticaly, intrapleurally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

EXAMPLES

Protease-Responsive Imaging Sensors Detect and Image Colorectal Cancer (CRC) Metastasis.

This Example evaluated the ability of protease-responsive imaging sensors (PRISMs) to detect and image colorectal cancer (CRC) metastasis. In particular, mouse models of CRC liver and lung metastasis were used.

To advance sensitive detection of cancer metastases and increase efficacy of treatments, new sensors that harness metastasis-specific proteases as triggers to release urinary biomarkers for sensitive detection and imaging of tumor metastases were developed. This approach integrates the activatable release of a urinary reporter for early disease detection with a pathological pH-triggered signal amplification for the precise imaging of CRC metastases by PET/CT. Two strategies endowed ultrasensitivity to these sensors: (1) a peptide substrate susceptible to cleavage by a metastasis-specific protease sheds labeled fragments into the urine via proteolytic cleavage, and (2) a pH low insertion peptide (pHLIP) localizes the cancer-specific signal by engaging active tumor trafficking and insertion triggered by acidic microenvironments (FIG. 1, I & II).

Figure 2A:
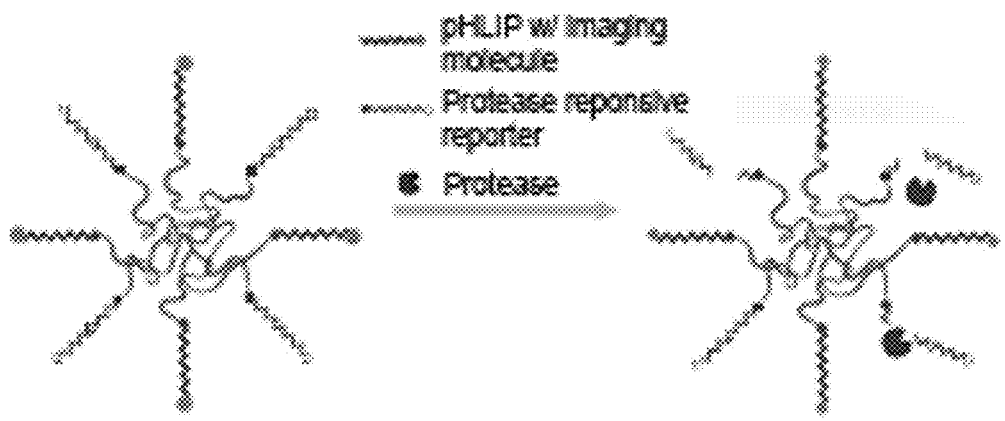
FIGS. 2A-2J show that PRISM detects CRC liver metastasis in a pre-clinical immunocompetent mouse model.

Activity-based urinary detection encompasses two steps of amplification by allowing single proteases to cleave thousands of substrates, which then are concentrated over 20 fold in the urine (from ~5 L of blood to ~0.2 L void volume). When applied to a disseminated ovarian cancer model, targeted activity-based sensors detected tumor nodules with median diameters of <2 mm, whereas the blood biomarker HE4 was only able to detect tumors at an average total burden of 88 $mm^3$ (Kwon et al., Nat Biomed Eng. 2017; 1). With this level of predictive power, once the urinary signal turns positive, one can leverage advanced medical imaging to carefully screen and stratify patients in order to establish an effective treatment regimen (FIG. 1, III & IV). In addition to the powerful urinary signal detection, the advanced medical imaging, here PET/CT, provides a noninvasive approach that monitors disease progression in primary or metastatic tumors, and also patients' response to specific treatments (Longo et al., Cancer Res. 2016 Nov. 15; 76(22):6463-6470; Sun et al., Sci Transl Med. 2018 Mar. 7; 10(431); Farwell et al., Cancer. 2014 Nov. 15; 120(22):3433-45; Zinnhardt et al., Cancer Res. 2017 Apr. 15; 77(8):1831-1841). PET and CT are both standard imaging tools used by healthcare providers to pinpoint disease sites in the body. The PET scan demonstrates biological function of the body (i.e., cell physiology). The CT scan provides information on anatomy including size, shape, and location of structures in the body (Farwell et al., Cancer. 2014 Nov. 15; 120(22):3433-45). Combining these two noninvasive technologies, PET/CT can more accurately and quickly diagnose, stage, and monitor treatment for cancer. Radioactive PET tracers used in clinics, such as $^{18}$F-2-deoxyfluoroglucose (FDG), visualize differences in metabolic activity that accompany inflammation but lack the discriminatory power that tumor-targeting moieties (peptides, antibodies, or their fragments) might afford (Sun et al., Sci Transl Med. 2018 Mar. 7; 10(431); Rashidian et al., Proc Natl Acad Sci USA. 2015 May 12; 112(19):6146-51). However, these moieties tend to accumulate in kidneys and other organs of elimination, resulting in suboptimal signal-to-noise ratios. Considering the benefits of PEG-based reporters of protease cleavage and PEGylation for optimized imaging signal, a first iteration of PRISM was constructed using multivalent polyethylene glycol scaffolds. These sensors carried two functional components: (1) a peptide substrate that sheds labeled fragments into the urine via proteolytic cleavage of MMP9, which is significantly upregulated in both primary and metastatic CRC (Kwon et al., Nat Biomed Eng. 2017; 1), and (2) a pH low insertion peptide (pHLIP) that engages active tumor trafficking and insertion triggered by acidic microenvironments to localize the cancer-specific imaging signal (FIG. 2A). Specifically, both pHLIP and the MMP9-activated urinary reporter were immobilized on polychain PEG by click chemistry. By modifying pHLIP with fluorophores, tracers, or a combination thereof at the N-terminus, one can enable tumor-specific imaging with desired imaging techniques. The scaffold (8-arm PEG) was directly conjugated with the enzyme-specific substrate and the pH low insertion peptide through covalent linkage, using DBCO-azide click chemistry.

Figure 2B:
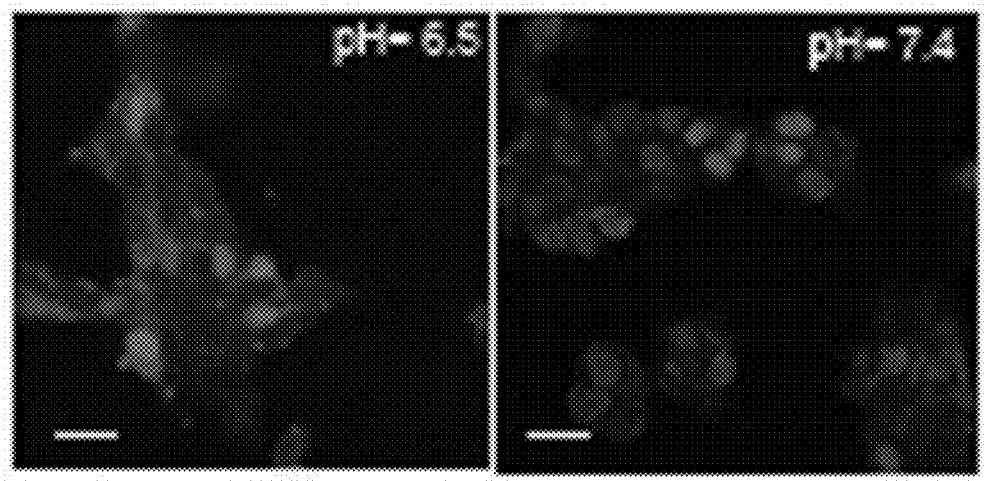
Figure 2C:
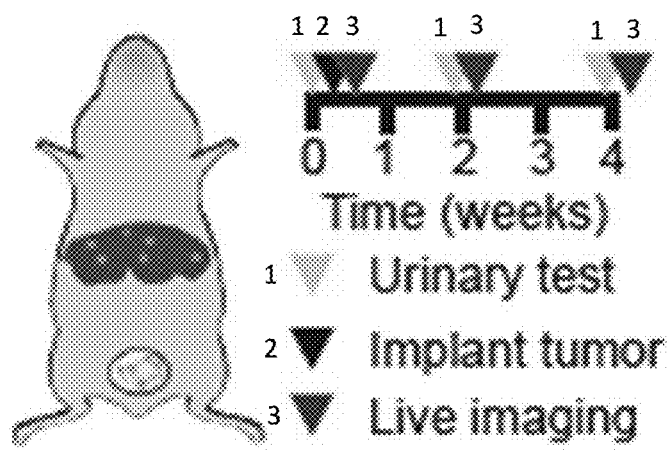
Figure 2D:
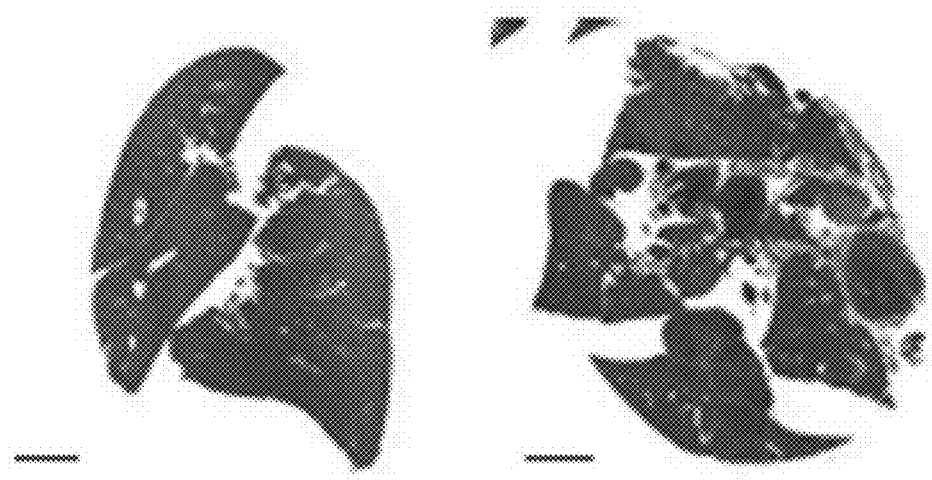
Figure 2E:
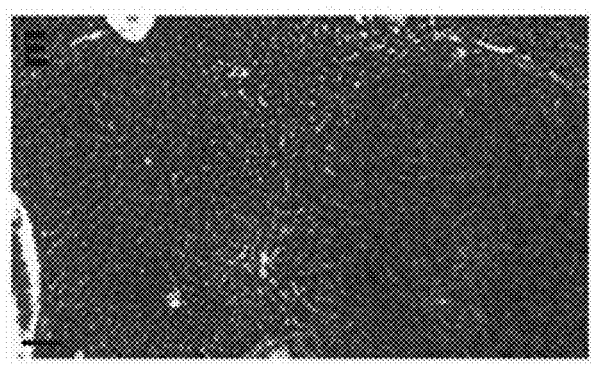
Figure 2F:
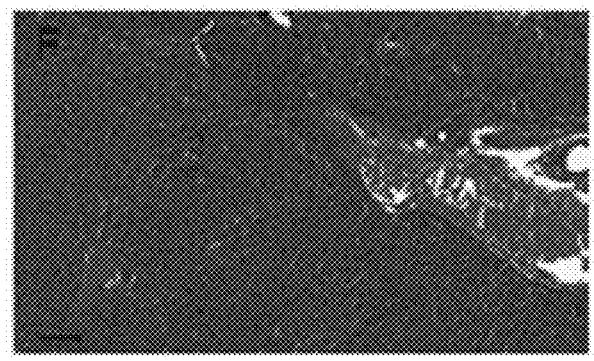
Figure 2G:
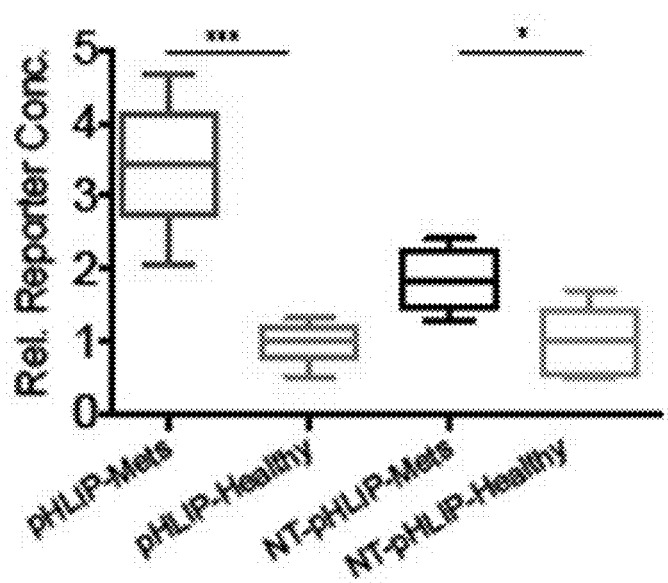
Figure 2H:
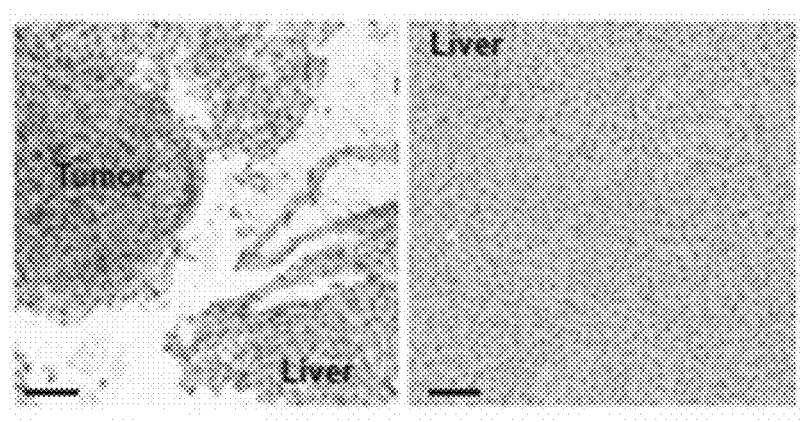
Figure 2I:
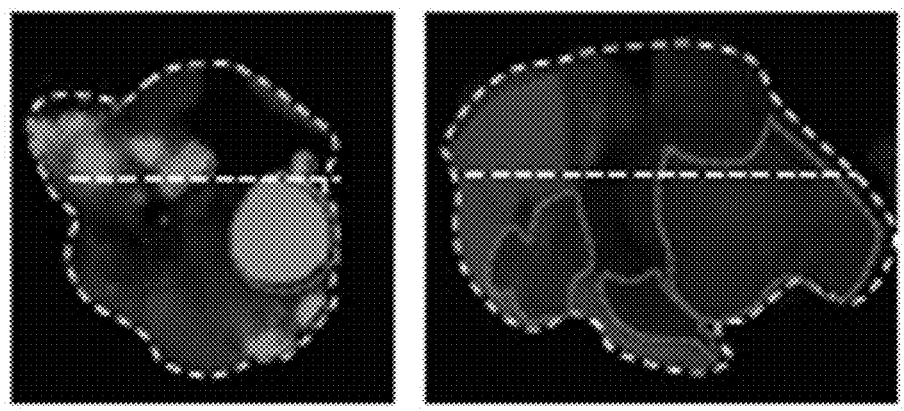
Figure 2J:
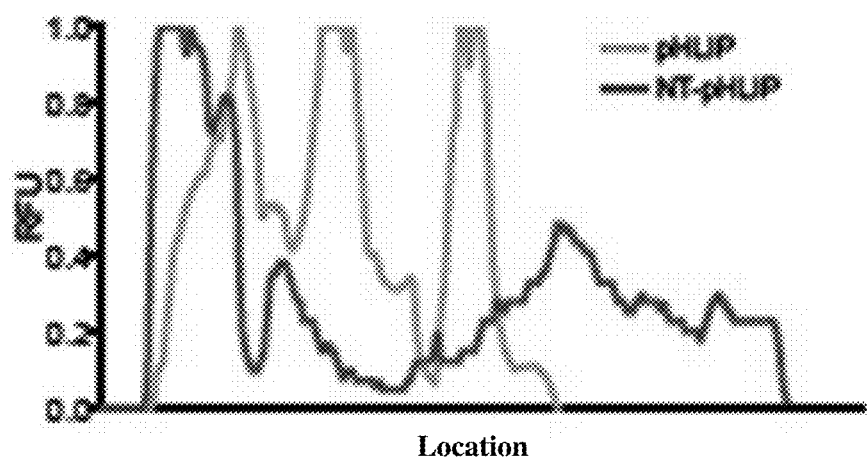
Figure 3A:
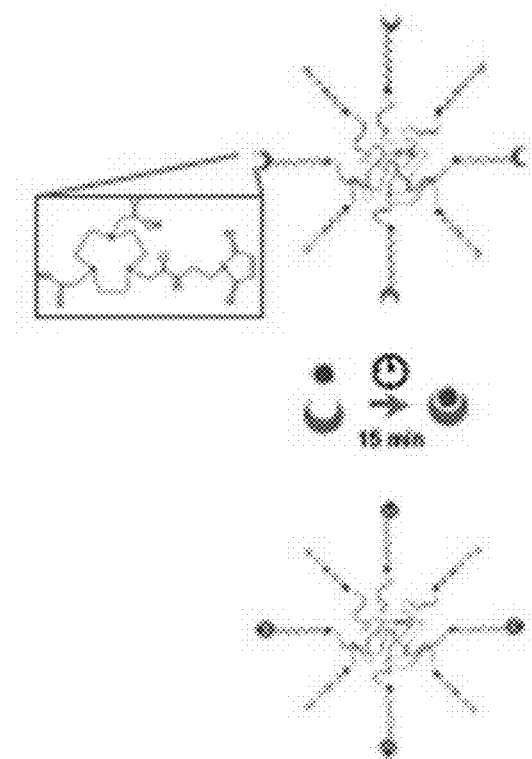
FIGS. 3A-3H show $^{64}$Cu-labeled PRISM detects CRC liver metastasis.
Figure 3B:
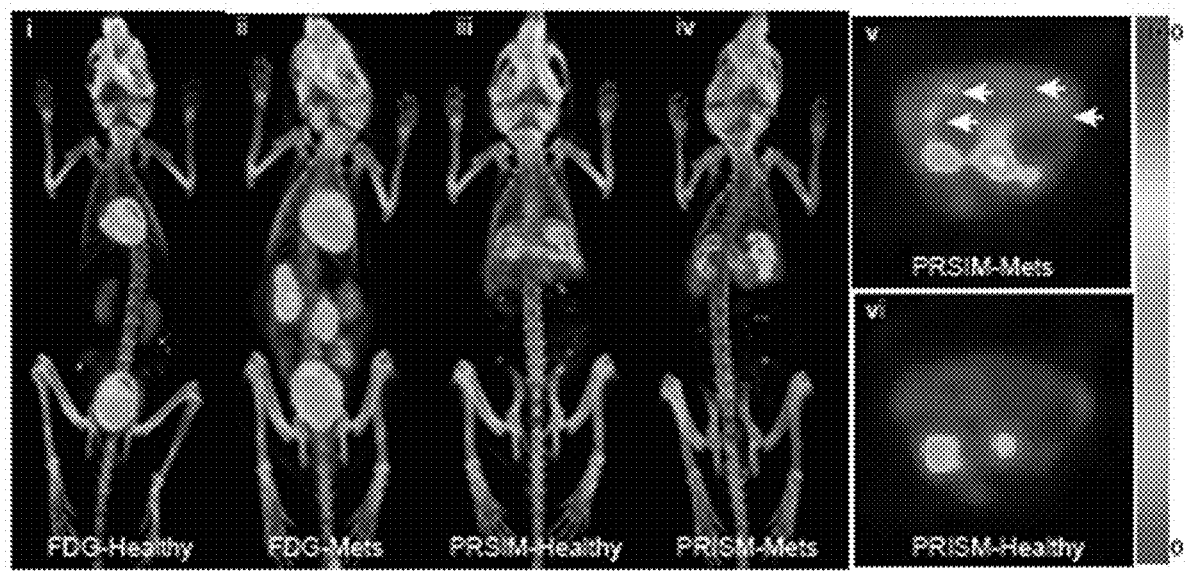
Figure 3C:
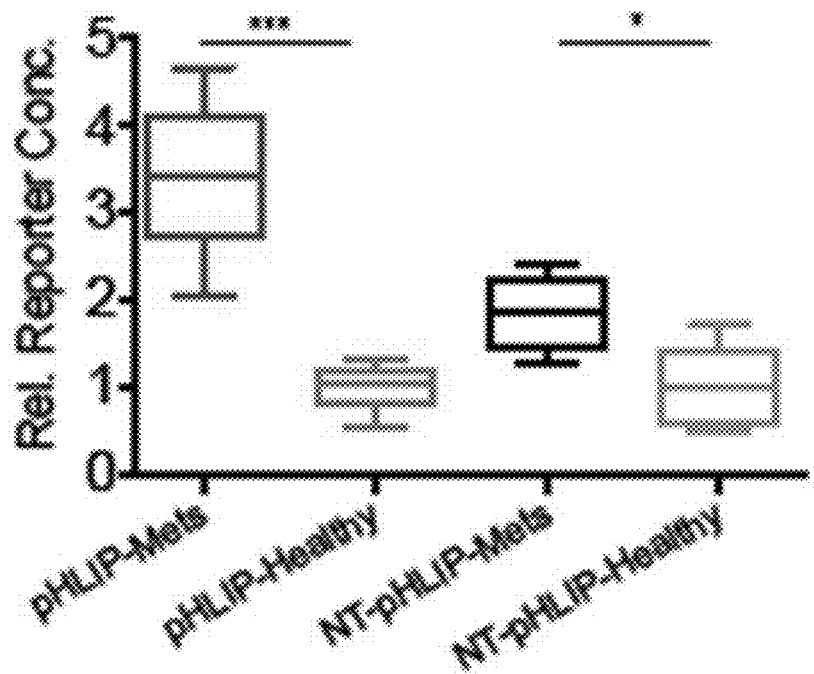
Figure 3D:
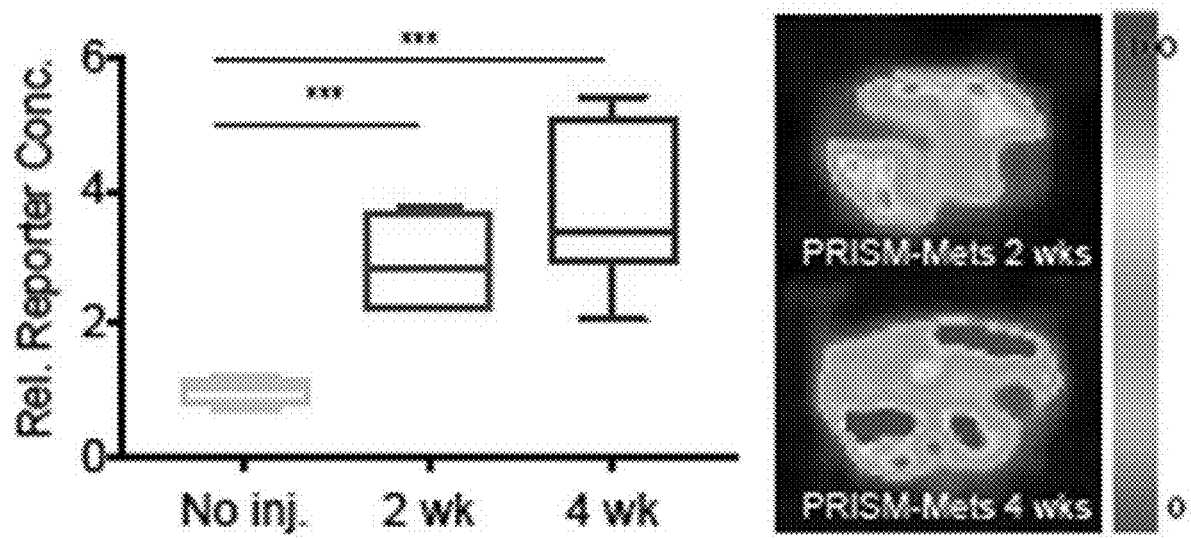
Figure 3E:
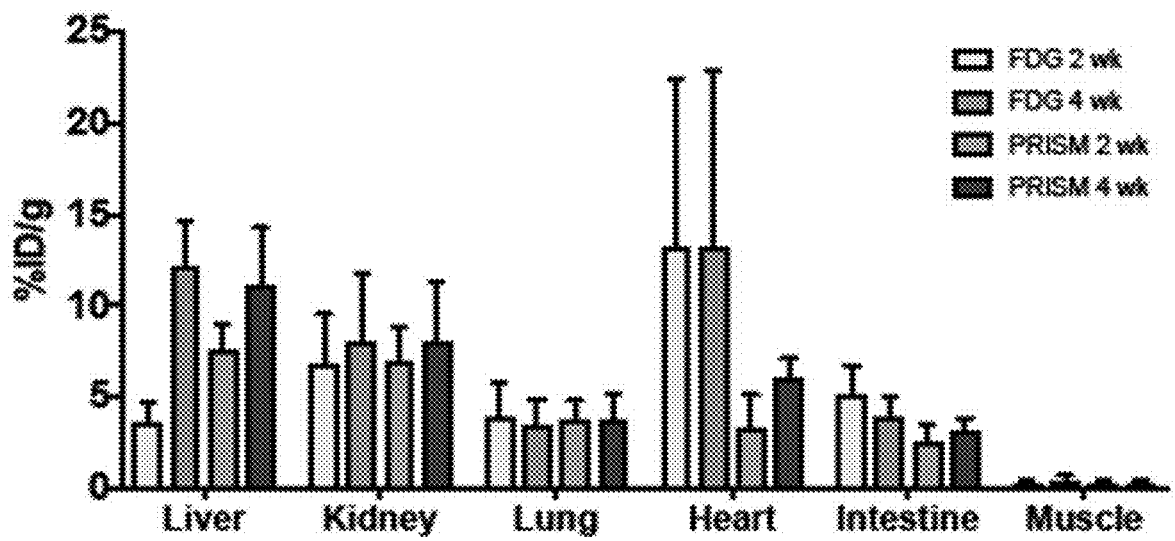
Figure 3F:
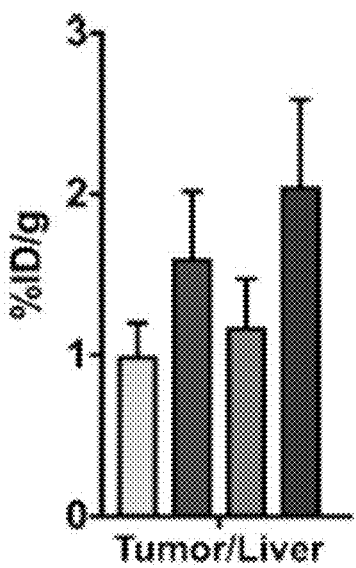
Figure 3G:
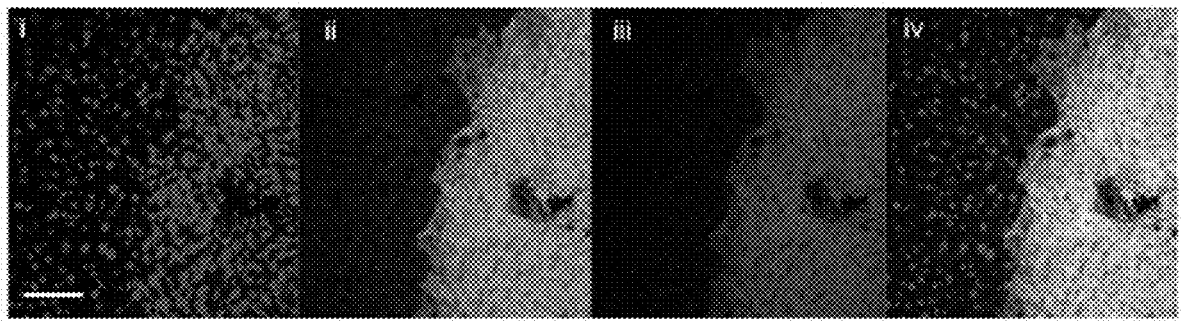
Figure 3H:
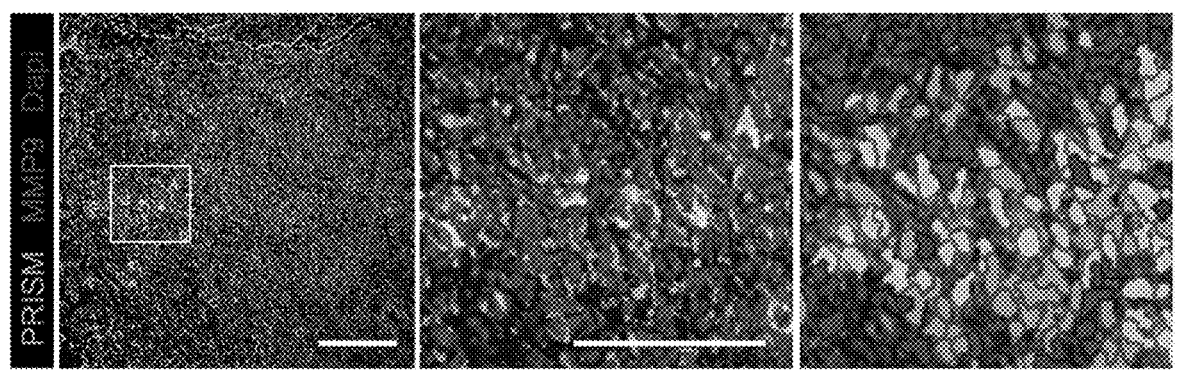

PRISM is 15 nm in diameter and carries ~1:1 of pHLIP and MMP9-activated urinary reporters. When incubated with cancer cells at acidic pH (6.5), PRISM exhibited significantly higher cell accumulation than that observed at pH 7.4 (FIG. 2B). An intrasplenic injection model of liver metastases was developed. Following a midline incision and externalization of the spleen in Balb/c mice, the luciferized MMP9-secreting CRC cell line (MC26) was inoculated into the subsplenic capsule, allowed cells to traverse vasculature to seed the liver, and then removed the spleen to prevent ectopic tumor growth (FIGS. 2C, 2D, 2E & 2F) (Danino et al., Sci Transl Med. 2015 May 27; 7(289):289ra84). Upon intravenous administration of sensors, urine samples from tumor-bearing and healthy control mice were collected after 1 hr, and the reporter levels were detected by ELISA. Comparison of urinary signals generated by two sets of sensors bearing pHLIP or its non-targeting counterpart revealed a 1.8-fold increase in cancer-specific signal generation, suggesting pH-selective targeting of PRISM enhanced sensitivity of detection (FIG. 2G). At 2 and 6 hr post-injection, mice underwent small animal PET/CT imaging for longitudinal assessment of pHLIP reporter. 1,4,7-triazacyclononane-triacetic acid (NOTA) was site-specifically conjugated to pHLIP by maleimide chemistry (FIG. 3A). For real-time in vivo imaging, singly-labeled $^{64}$Cu successfully imaged CRC liver and lung metastases in immunocompetent Balb/c mice, resulting in positive-to-negative tumor ratios of 2.2:1 (FIG. 3B). Quantification of urinary reporters collected at different time points, and longitudinal observation of individual animals indicated growth of metastatic sites in the liver (FIG. 3D). The PRISM probe was benchmarked against the conventional PET tracer used in clinics, $^{18}$F-FDG, and found that the standard uptake value in major organs such as liver, kidney, lung, intestine are comparable (FIG. 3E). In particular, similar tumor versus liver ratios were observed in mice imaged with $^{18}$F-FDG and $^{64}$Cu-PRISM, respectively, demonstrating that PRISM is effective in imaging of metastases in vivo (FIG. 3F). At the end of the determined time point, the mice were sacrificed and livers with metastases were collected and subjected to ex vivo immunofluorescence and immunohistochemistry analysis. The extracellular protease, MMP9, accumulated along the metastasis invasion front, and PRISM sensors were colocalized with abnormal physiologic conditions such as hypoxia (FIGS. 2H and 3G).

Figure 4A:
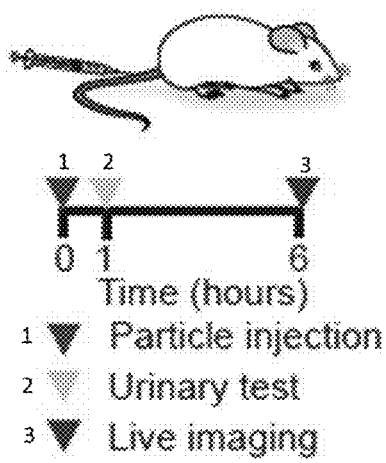
FIGS. 4A-4K show PRISM for detection and imaging in CRC lung metastasis model.
Figure 4B:
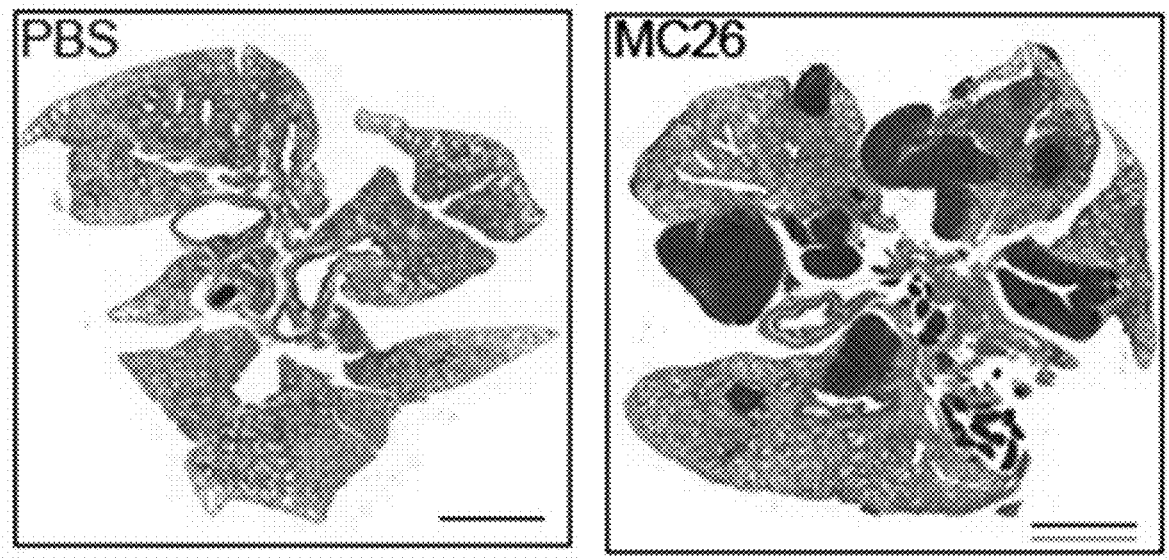
Figure 4C:
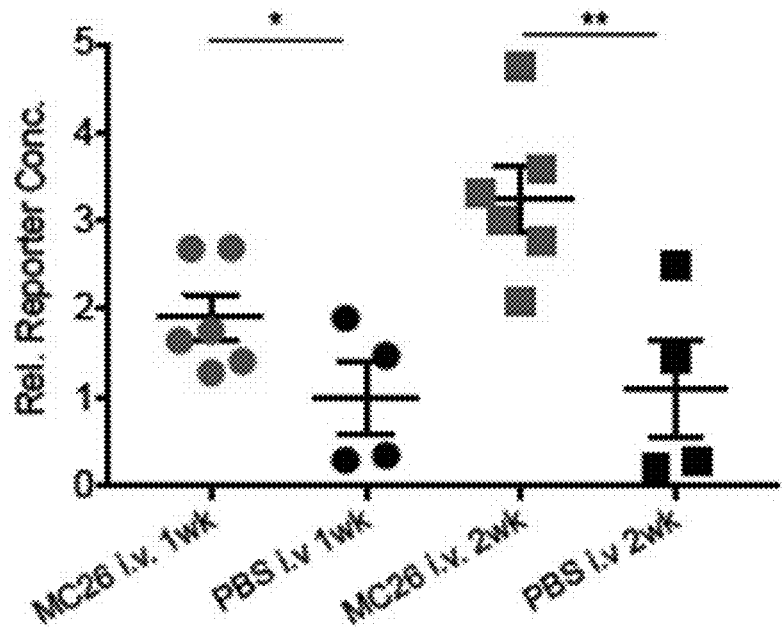
Figure 4D:
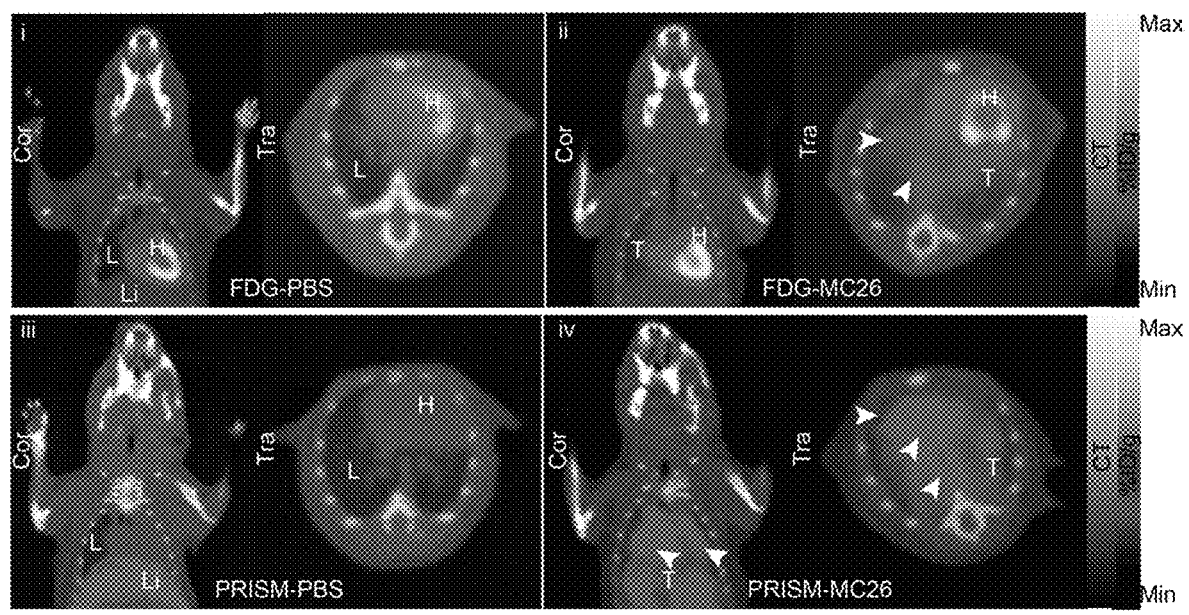
Figure 4E:
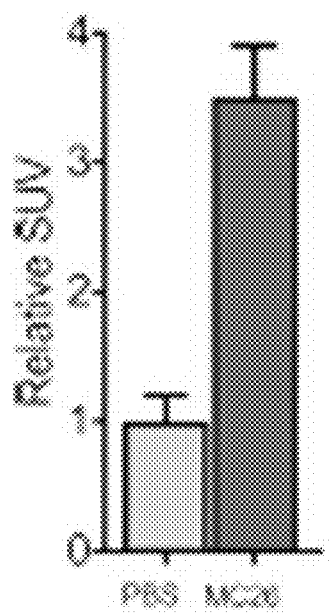
Figure 4F:
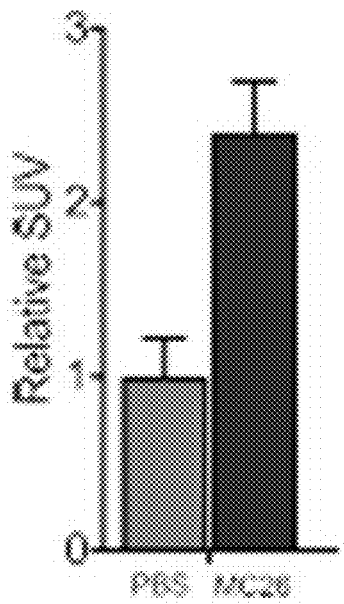
Figure 4G:
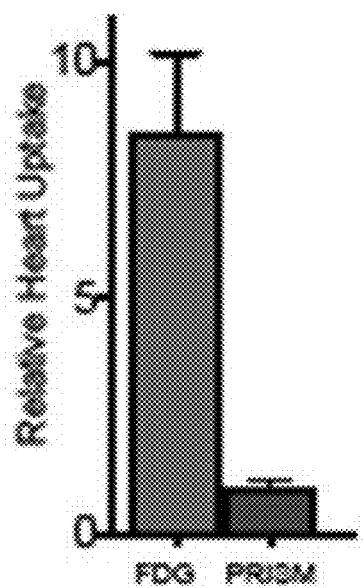
Figure 4H:
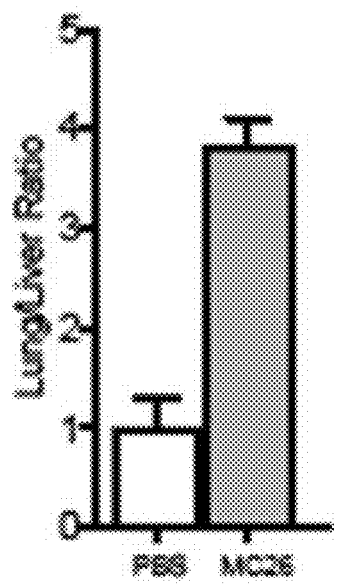
Figure 4I:
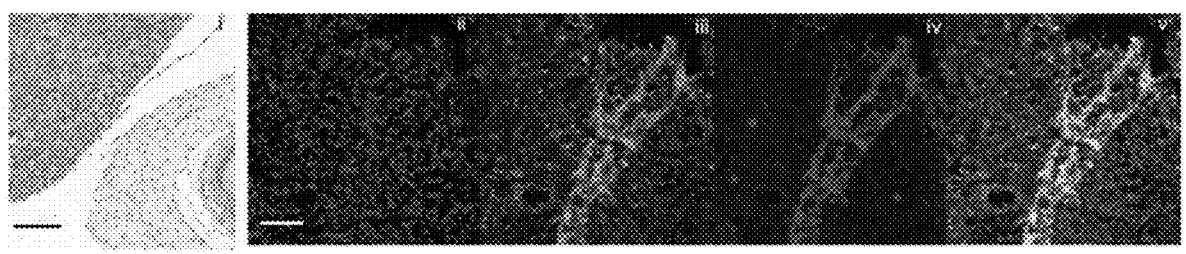
Figure 4J:
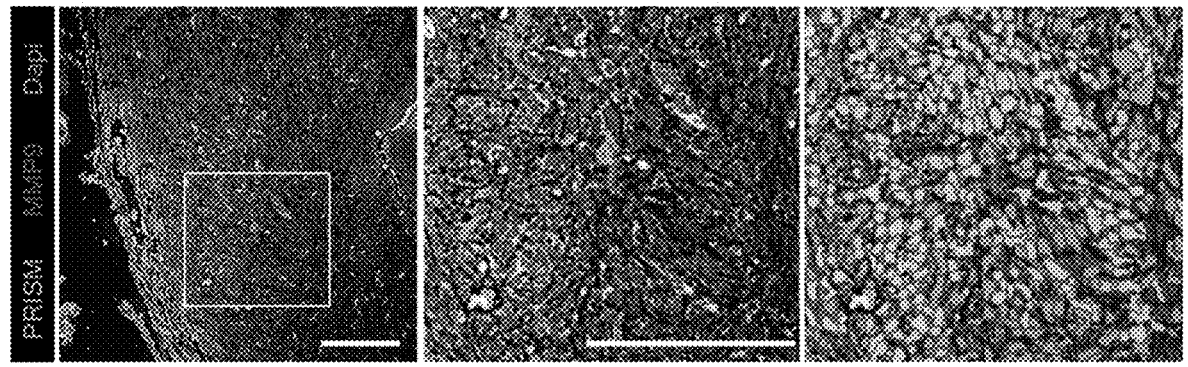
Figure 4K:
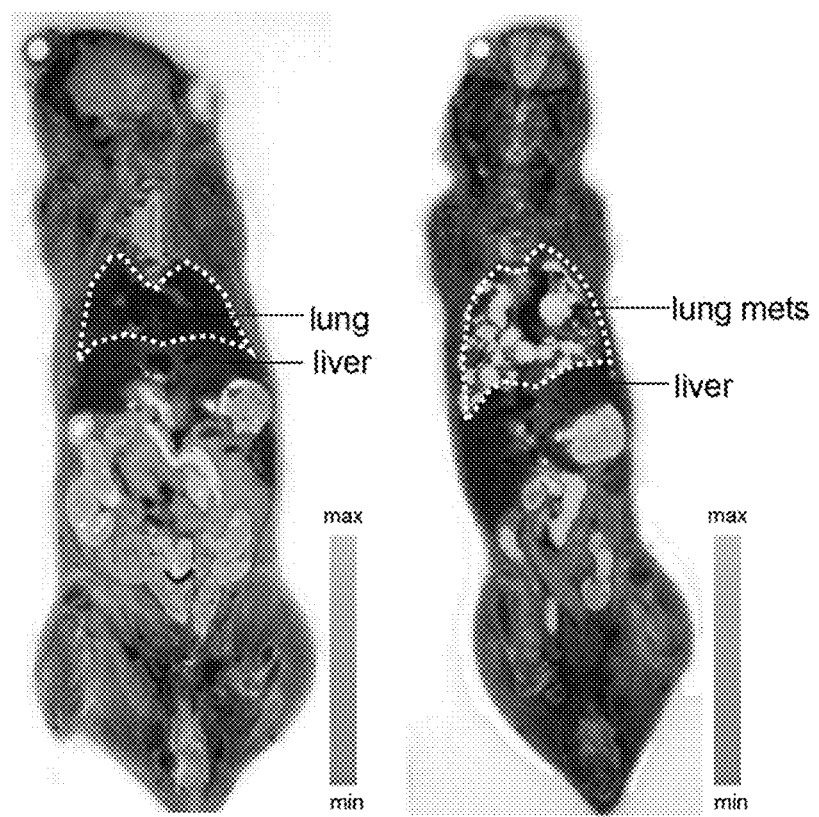

The efficacy of the sensors were also demonstrated in mice bearing CRC lung metastases, which exhibit low glucose uptake tumor (LS174T, data not shown). The CRC lung model was established through intravenous injection of MMP9-secreting MC26 cells in female Balb/c mice. Massive metastasis formation was observed within 2-3 weeks of tumor inoculation (FIG. 4B). Upon intravenous administration of sensors, urine samples from tumor-bearing and healthy control mice were collected after 1 hr, and the ELISA readouts of reporter levels increased as tumor growth progressed (FIG. 4C). Singly-labeled $^{64}$Cu-PRISM successfully imaged CRC lung metastases, resulting in positive-to-negative tumor ratios of 2.4:1 (FIGS. 4D and 4E). Then the PET/CT images of the same mice were compared, imaged with $^{64}$Cu-PRISM and $^{18}$F-FDG. Although the standard uptake value is comparable, FDG has a strong accumulation in the heart, and the resulting high background signal obscures covers some of the lung-derived signal, whereas the application of PRISM gave rise to significantly less background signal in the chest (FIGS. 4D, 4F, 4G, and 4H). Therefore, PRISM holds great potential in tracking tumors in certain organs compared with conventional PET tracer. In the CRC lung metastasis model, PRISM also specifically localized to the tumor invasion front, and colocalized with hypoxic regions (FIG. 4I).

PRISM Monitors Treatment Efficacy in Mouse Models of CRC Metastasis.

Figure 5A:
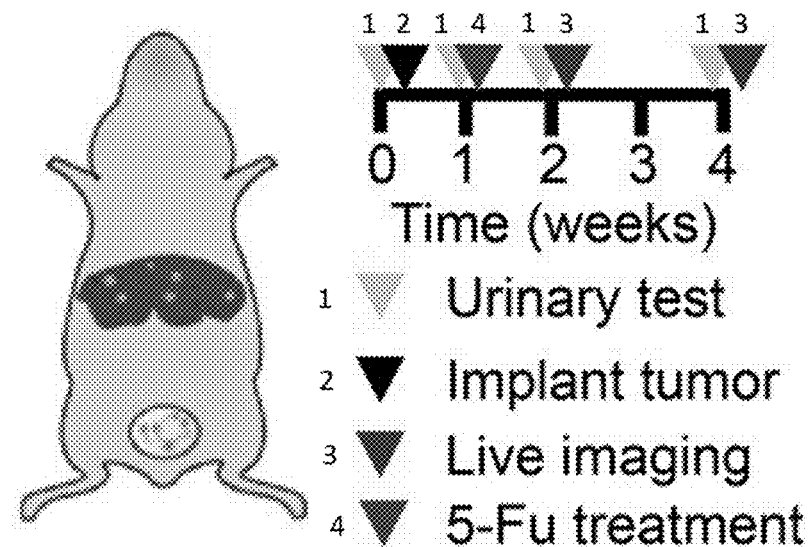
FIGS. 5A-5G show PRISM for chemotherapy treatment monitoring in CRC liver metastasis model.
Figure 5B:
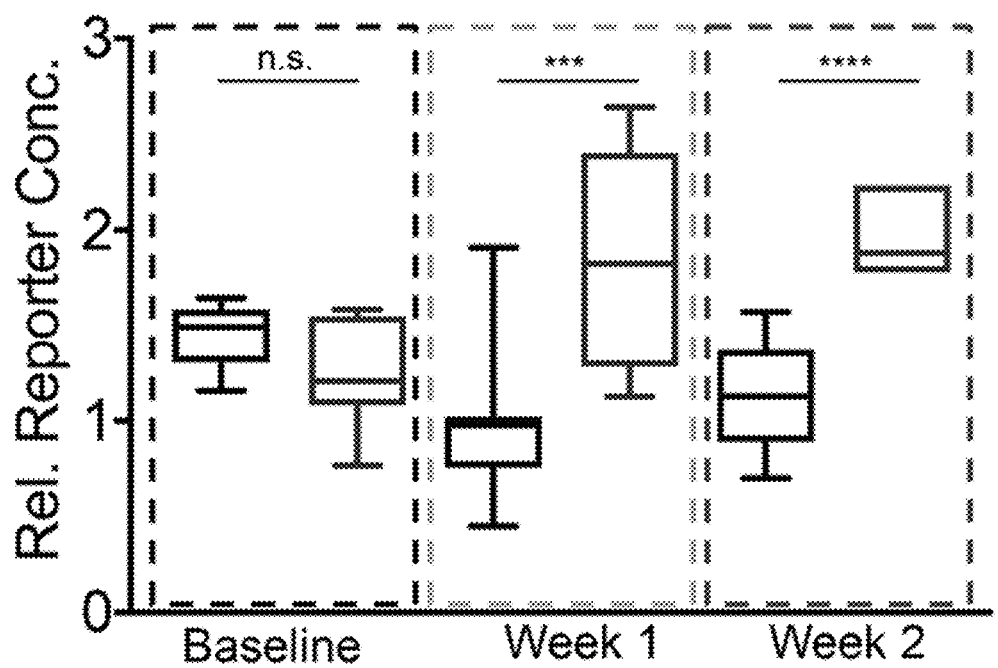
Figure 5C:
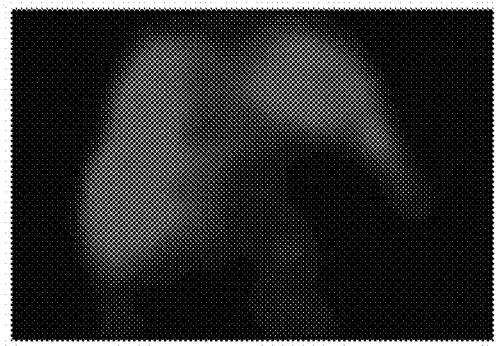
Figure 5D:
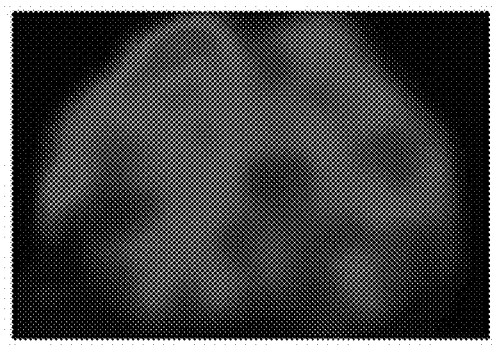
Figure 5E:
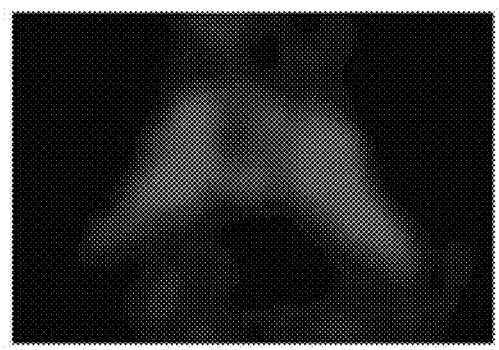
Figure 5F:
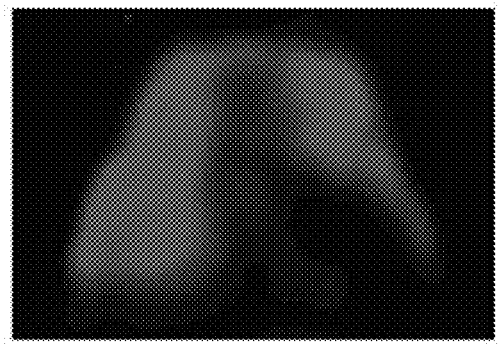
Figure 5G:
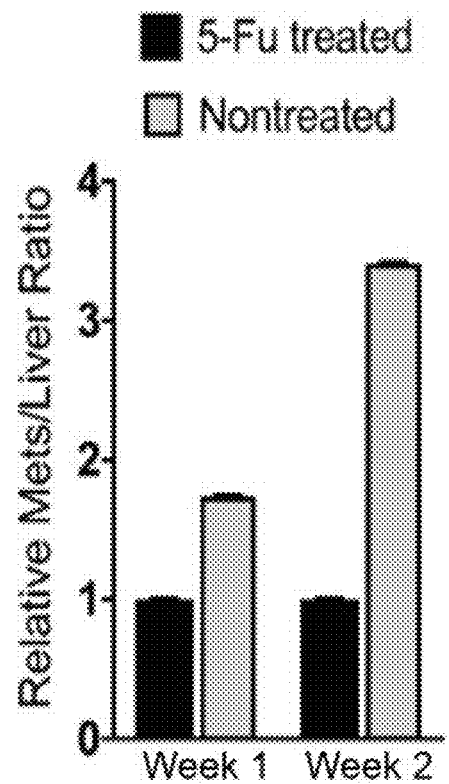

After validation of the efficacy of tailored PRISM nanoparticles, these sensors were applied to study how proteolytic activities correlate with changes in the progression of disease over time and in response to drug treatment. In addition, molecular imaging was safely performed for any lesion for multiple times, providing information related to regional heterogeneity in a given tumor. To evaluate PRISM in monitoring treatment responses, mice were grouped into two categories (n=5 each) to allow monitoring the effect of standard chemotherapy 5-FU treatment: one group received drug (15 mg/kg) by i.p. injection (daily injection for 4 days and once every other day till end of study); and the second group received vehicle as control. To monitor therapeutic responses in treating metastases, PRISM was intravenously injected in each group of mice. After 1 hr of sensor injection, urinary reporter level was assayed to track local proteolytic activity, reflecting tumor invasion capacity. At 6 hrs post-injection, mice were scanned using a small animal PET/CT imager for longitudinal assessment of the tumor progression. Starting 5-FU treatment two weeks after tumor inoculation in the CRC liver metastasis model significantly inhibited tumor progression, consistent with the decreased urinary reporter level compared with the non-treated cohort (FIG. 5B). Real-time images were analyzed and standard uptake value of radioactive reporters were quantified using VivoQuant software. Over 2 weeks of treatment, untreated mice showed substantially increased tumor burden in the liver (FIGS. 5C-5D). In contrast, 5-FU treatment significantly slowed tumor growth compared with the untreated controls (FIGS. 5D-5E).

Figure 6A:
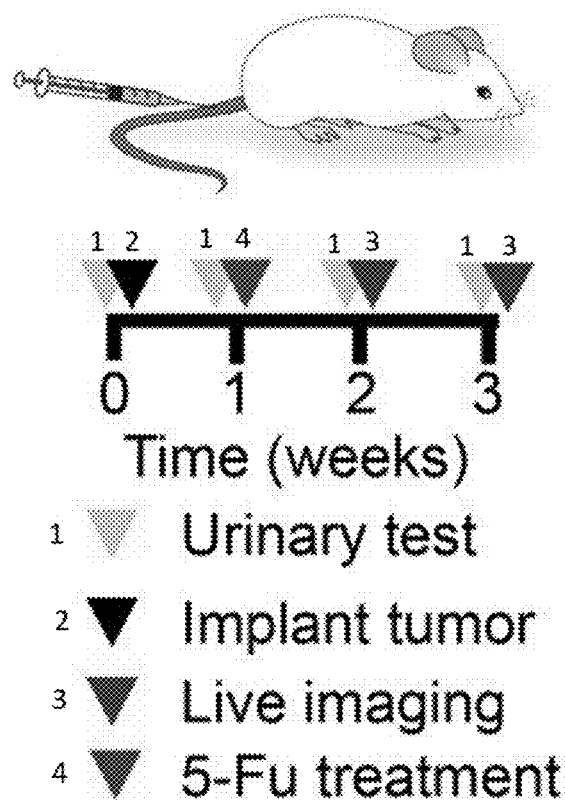
FIGS. 6A-6G show PRISM for treatment monitoring in CRC lung metastasis model.
Figure 6B:
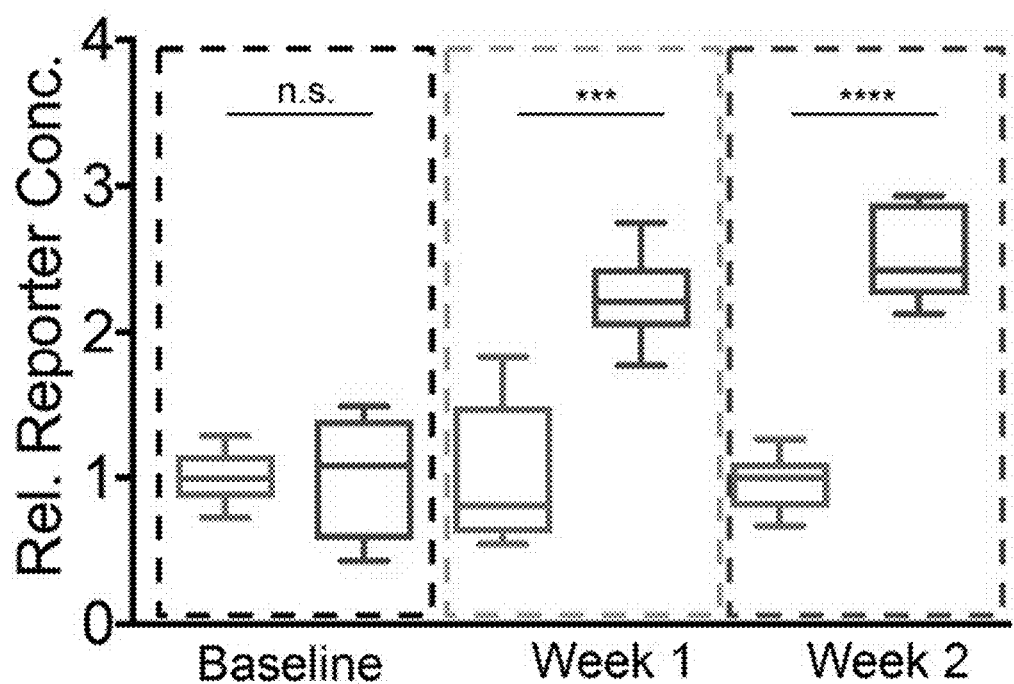
Figure 6C:
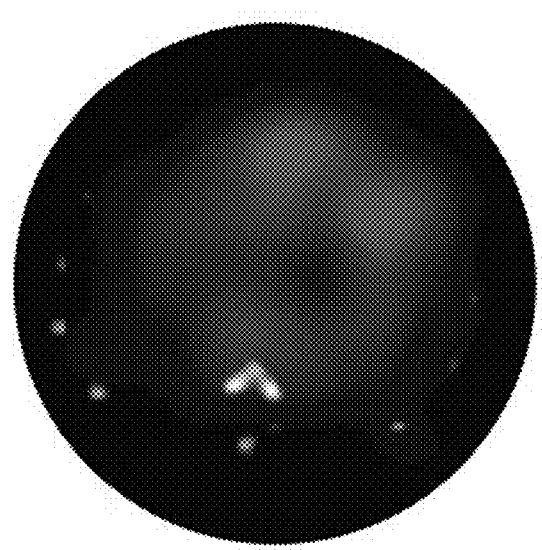
Figure 6D:
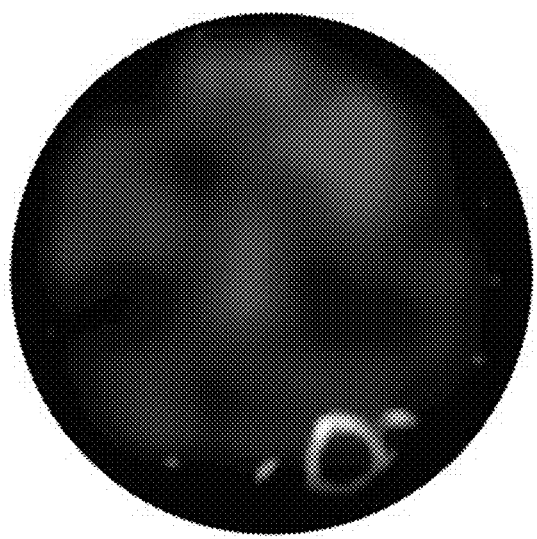
Figure 6E:
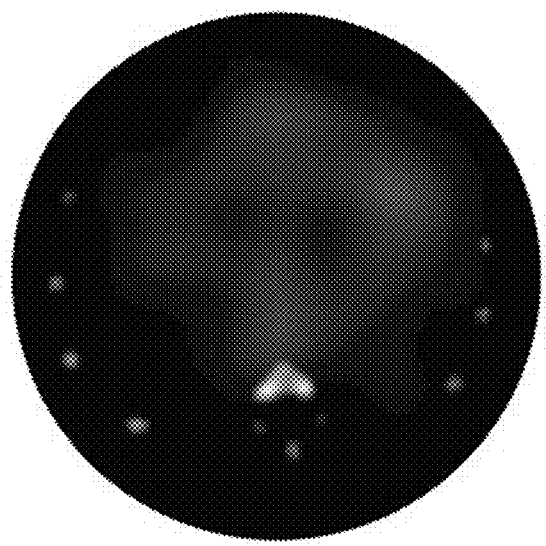
Figure 6F:
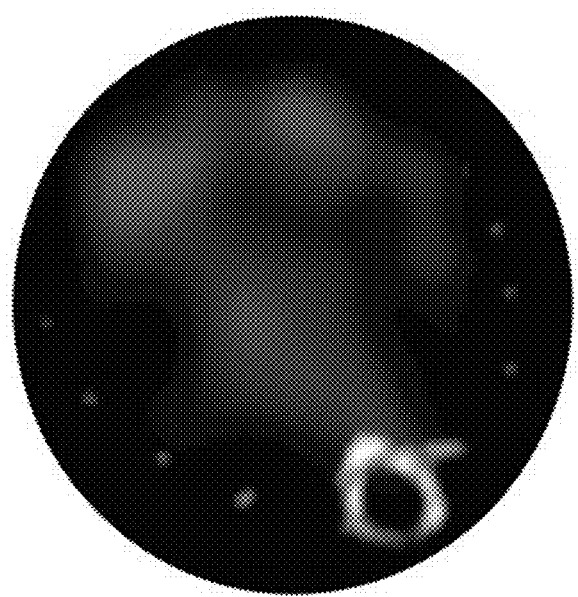
Figure 6G:
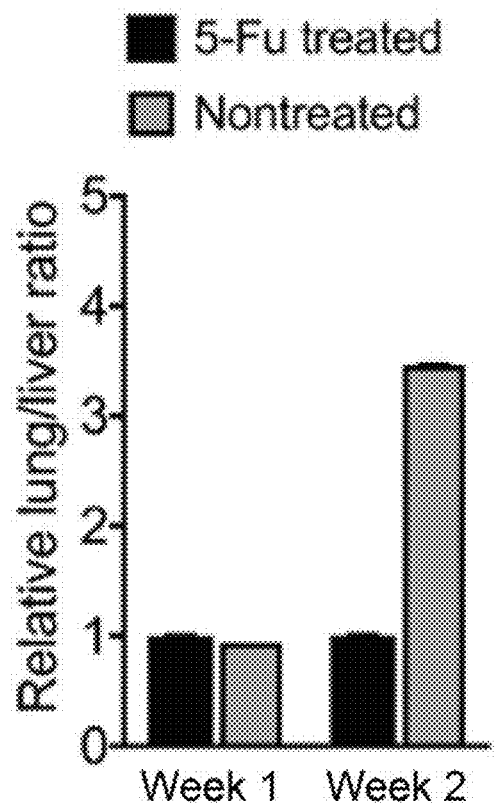

To monitor therapeutic responses when metastases in the CRC lung metastasis model were treated, PRISM was again intravenously injected in two group of mice on a weekly basis. One hour following sensor injection, urinary reporter level was read to track the local proteolytic activity. Significantly reduced urinary reporter levels were observed in 5-FU treated mice, reflecting decreased tumor invasion capacity compared with untreated control group. 6 hours after sensor injection, PET/CT were applied to monitor tumor growth or regression, which provides a longitudinal, noninvasive assessment of the efficacy of anti-tumor drug treatment. Every mouse that received 5-FU showed slower tumor growth compared with the untreated controls. Consistently, the relative lung/liver ratio of PET/CT signal in the cohort that received no treatment was over 3 times higher than that of the cohort treated with chemotherapy (n=5) (FIG. 6G).

Table 5 includes a list of pH low insertion peptides used in this Example. In Table 5, lower case letters indicate a D-form amino acid, "N3" indicates an azide side chain, and "Cy7" indicates cyanine.

TABLE 5

Peptides.

| Name of Peptide | Sequence (N→C) | Type of pHLIP |
|---|---|---|
| pHLIP | AAEQNPIYWARYADWLFTTPLLLLDL ALLVDADEGTC (SEQ ID NO: 31) | pHLIP |
| pHLIP-F | AAEQNPIYWARYADWLFTTPLLLLDL ALLVDADEGTC(Cy7) (SEQ ID NO: 32) | pHLIP with fluorophore |
| pHLIP-V3 | ACDDQNPWRAYLDLLFPTDTLLLDLL Wkk (SEQ ID NO: 33) | modified pHLIP (used in this Example) |
| pHLIP-V3-F | AC(Cy7)DDQNPWRAYLDLLFPTDTLL LDLLWkk (SEQ ID NO: 34) | modified pHLIP (used in this Example) |
| pHLIP-V3-L | K(N3)GGACDDQNPWRAYLDLLFPTD TLLLDLLWkk (SEQ ID NO: 35) | modified pHLIP (used in this Example) |
| D-pHLIP-V3-L | K(N3)GGacddqnpwrayldllfptdtllldllwkk (SEQ ID NO: 36) | modified pHLIP (used in this Example) |
| NT-pHLIP-V3 | ACDDQNPWRAYLKLLFPTKTLLLKLL Wkk (SEQ ID NO: 37) | non-targeting control peptide (used in this Example) |
| NT-pHLIP-V3-F | AC(Cy7)DDQNPWRAYLKLLFPTKTLL LKLLWkk (SEQ ID NO: 38) | non-targeting control peptide (used in this Example) |
| NT-pHLIP-V3-L | K(N3)GGACDDQNPWRAYLKLLFPTK TLLLKLLWkk (SEQ ID NO: 39) | non-targeting control peptide (used in this Example) |

TABLE 5-continued

Peptides.

| Name of Peptide | Sequence (N→C) | Type of pHLIP |
|---|---|---|
| D-NT-pHLIP-V3-L | K(N3)GGacddqnpwrayldllfptdtllldllwkk (SEQ ID NO: 40) | non-targeting control peptide (used in this Example) |

Additional Embodiments

Paragraph 1. A protease imaging sensor comprising:
(a) a scaffold linked to an enzyme-specific substrate that is attached to a first detectable marker, wherein the first detectable marker is capable of being released from the sensor when exposed to an enzyme, and,
(b) a tumor imaging agent comprising a second detectable marker, wherein the tumor imaging agent is linked to the scaffold and wherein the tumor imaging agent does not include a cell penetrating domain.

Paragraph 2. The protease imaging sensor of paragraph 1, wherein the tumor imaging agent further comprises a pH low insertion peptide.

Paragraph 3. The protease imaging sensor of paragraph 1 or 2, wherein the scaffold comprises a protein, a polymer, or a nanoparticle, optionally wherein the protein, polymer or nanoparticle is greater than about 5 nm in diameter.

Paragraph 4. The protease imaging sensor of any one of paragraphs 1 to 3, wherein the scaffold comprises a multi-arm polyethylene glycol molecule (multi-arm PEG), optionally wherein the multi-arm PEG comprises 2-20 arms, optionally wherein the multi-arm PEG comprises 8 arms.

Paragraph 5. The protease imaging sensor of paragraph 4, wherein the multi-arm PEG has a total diameter between 5 nm and 20 nm, optionally wherein the multi-arm PEG has a total diameter of about 15 nm.

Paragraph 6. The protease imaging sensor of any one of paragraphs 1 to 5, wherein the scaffold comprises an iron oxide nanoparticle (IONP), optionally wherein the IONP is between about 10 nm and about 20 nm in size.

Paragraph 7. The protease imaging sensor of any one of paragraphs 1 to 6, wherein each enzyme-specific substrate comprises a cancer substrate, optionally wherein the cancer substrate is cleaved by an enzyme associated with colorectal cancer (CRC).

Paragraph 8. The protease imaging sensor of paragraph 7, wherein the cancer substrate is a cancer metastasis substrate, optionally wherein the cancer metastasis substrate is cleaved by an enzyme associated with colorectal cancer metastasis.

Paragraph 9. The protease imaging sensor of any one of paragraphs 1 to 8, wherein the first detectable marker comprises a peptide, a nucleic acid, a small molecule, a fluorophore, a carbohydrate, a particle, a radiolabel, a MRI-active compound, a ligand encoded reporter, or a isotope coded reporter molecule (iCORE).

Paragraph 10. The protease imaging sensor of paragraph 9, wherein the second detectable marker comprises a radiolabel and is detectable by positron emission tomography or computerized tomography.

Paragraph 11. The protease imaging sensor of paragraph 10, wherein the radiolabel is selected from the group consisting of $^{64}$Cu, Gd(DOTA), $^{201}$Tl, $^{99m}$Tc, $^{18}$F-2-deoxyfluoroglucose (FDG), (18)F-fluoride, gadodiamide, radioisotopes of Pb(II), $^{111}$In, and $^{89}$Zr.

Paragraph 12. The protease imaging sensor of any one of paragraphs 10 or 11, wherein the second detectable marker comprises a metal chelator selected from the group consisting of 1,4,7-Triazacyclononane-1,4,7-triacetic acid (NOTA), 1,4,7,10-tetraazacyclododecane-N,N',N'',N'''-tetraacetic acid (DOTA), Diethylenetriaminepentaacetic Anhydride (DTPA), 1,4,8,11-tetraazacyclotetradecane-1,4,8,11-tetraacetic acid (TETA), and deferoxamine (for $^{89}$Zr).

Paragraph 13. The protease imaging sensor of any one of paragraphs 2 to 12, wherein the pH low insertion peptide is selected from the group consisting of SEQ ID NOs: 14-40.

Paragraph 14. The protease imaging sensor of any one of paragraphs 1 to 13, wherein the wherein the pH low insertion peptide comprises a D-amino acid, an azide side chain, and/or cyanine.

Paragraph 15. The protease imaging sensor of any one of paragraphs 1 to 14, wherein the tumor imaging peptide is N-terminally linked to the scaffold.

Paragraph 16. The protease imaging sensor of any one of paragraphs 1 to 15, wherein the scaffold comprises a single enzyme-specific substrate, a single tumor imaging peptide, or a combination thereof.

Paragraph 17. The protease imaging sensor of any one of paragraphs 1 to 16, wherein the scaffold comprises multiple enzyme-specific substrates, multiple tumor imaging peptides, or a combination thereof.

Paragraph 18. The protease imaging sensor of any one of paragraphs 1 to 17, wherein the ratio of the number of enzyme-specific substrates to the number of tumor imaging peptides is 1:1.

Paragraph 19. A method for detecting a tumor in a subject, the method comprising:
(a) administering to a subject a protease imaging sensor, wherein the protease imaging sensor comprises
(i) a scaffold linked to an enzyme-specific substrate that is attached to a first detectable marker, wherein the first detectable marker is capable of being released from the sensor when exposed to a cancer-associated enzyme at a site within the subject, and
(ii) a tumor imaging peptide comprising a second detectable marker, wherein the tumor imaging peptide is linked to the scaffold and wherein the tumor imaging agent does not include a cell penetrating domain; and
(b) detecting in a biological sample obtained from the subject the first detectable marker, wherein detection of the first detectable marker in the biological sample is indicative of the subject having a tumor and/or detecting in the subject the second detectable marker, wherein detection of the second detectable marker indicates the site of exposure to the cancer-associated enzyme.

Paragraph 20. The method of paragraph 19, wherein the tumor imaging peptide comprises a pH low insertion peptide.

Paragraph 21. The method of paragraph 19 or 20, wherein (b) comprises detecting the first detectable marker and detecting the second detectable marker.

Paragraph 22. The method of any one of paragraphs 19 to 21, wherein the biological sample is not derived from the site of exposure to the cancer-associated enzyme, optionally wherein the sample is a urine sample, blood sample, or tissue sample.

Paragraph 23. The method of any one of paragraphs 19 to 22, wherein the site of exposure to the cancer-associated enzyme is a site of metastasis.

Paragraph 24. The method of paragraph 23, wherein the site of metastasis is selected from the group consisting of lung, liver, or heart.

Paragraph 25. The method of any one of paragraphs 19 to 24, further comprising quantifying the amount of the second detectable marker.

Paragraph 26. The method of any one of paragraphs 19 to 25, wherein the detecting of the first detectable marker in (b) comprises a method selected from mass spectrometry, PCR analysis, DNA microarray, fluorescence analysis, a capture assay (e.g., ELISA), optical imaging, magnetic resonance imaging (MRI), positron emission tomography (PET) imaging, computerized tomography (CT) imaging, intraoperative imaging or any combination thereof.

Paragraph 27. The method of any one of paragraphs 19 to 26, wherein the detecting of the second detectable marker in (b) comprises a method selected from fluorescence analysis, optical imaging, magnetic resonance imaging (MRI), positron emission tomography (PET) imaging, computerized tomography (CT) imaging, intraoperative imaging, or any combination thereof.

Paragraph 28. The method of any one of paragraphs 19 to 27, wherein the subject is suspected of having, at risk for, or has cancer, optionally wherein the cancer is colorectal cancer.

Paragraph 29. The method of paragraph 28, wherein the subject has been administered a therapeutic agent.

Paragraph 30. The method of any one of paragraphs 19 to 29, further comprising (c) classifying a cancer as metastatic or non-metastatic.

Paragraph 31. A method for monitoring tumor progression in a subject, the method comprising:
(a) administering to a subject having a tumor a protease imaging sensor, wherein the protease imaging sensor comprises
  (i) a scaffold linked to an enzyme-specific substrate that is attached to a first detectable marker, wherein the first detectable marker is capable of being released from the sensor when exposed to a cancer-associated enzyme at a site within the subject, and
  (ii) a tumor imaging peptide comprising a second detectable marker, wherein the tumor imaging peptide is linked to the scaffold and wherein the tumor imaging agent does not include a cell penetrating domain;
(b) detecting in a biological sample obtained from the subject the first detectable marker, wherein detection of the first detectable marker in the biological sample is indicative of the subject having a tumor and/or detecting in the subject the second detectable marker, wherein detection of the second detectable marker indicates the site of exposure to the cancer-associated enzyme; and
(c) repeating (a) and (b) at least once, thereby monitoring tumor progression in the subject.

Paragraph 32. The method of paragraph 31, wherein the subject has been administered a first therapeutic agent, a first therapeutic intervention has been performed on the subject, or a combination thereof.

Paragraph 33. The method of paragraph 31 or 32, wherein (b) comprises detecting the first detectable marker and detecting the second detectable marker.

Paragraph 34. The method of any one of paragraphs 31 to 33, wherein the tumor imaging peptide comprises a pH low insertion peptide.

Paragraph 35. The method of any one of paragraphs 31 to 34, wherein the biological sample is not derived from the site of exposure to the cancer-associated enzyme, optionally wherein the sample is a urine sample, blood sample, or tissue sample.

Paragraph 36. The method of any one of paragraphs 31 to 35, wherein the site of exposure to the cancer-associated enzyme is a site of metastasis.

Paragraph 37. The method of paragraph 36, wherein the site of metastasis is selected from the group consisting of lung, liver, or heart.

Paragraph 38. The method of any one of paragraphs 31 to 37, further comprising quantifying the amount of the second detectable marker.

Paragraph 39. The method of any one of paragraphs 31 to 38, wherein the detecting of the first detectable marker in (b) comprises a method selected from mass spectrometry, PCR analysis, DNA microarray, fluorescence analysis, a capture assay (e.g., ELISA), optical imaging, magnetic resonance imaging (MRI), positron emission tomography (PET) imaging, computerized tomography (CT) imaging, intraoperative imaging or any combination thereof.

Paragraph 40. The method of any one of paragraphs 31 to 39, wherein the detecting of the second detectable marker in (b) comprises a method selected from fluorescence analysis, optical imaging, magnetic resonance imaging (MRI), positron emission tomography (PET) imaging, computerized tomography (CT) imaging, intraoperative imaging, or any combination thereof.

Paragraph 41. The method of any one of paragraphs 31 to 40, wherein the subject has colorectal cancer.

Paragraph 42. The method of any one of paragraphs 31 to 41, wherein the method further comprises (d) classifying a tumor as progressing, in remission, or stable.

What is claimed is:

1. A protease imaging sensor comprising:
   (a) a scaffold linked to an enzyme-specific substrate that is attached to a first detectable marker, wherein the first detectable marker is capable of being released from the sensor when exposed to a cancer-associated enzyme and detected at a remote bodily site, and
   (b) a tumor imaging agent that localizes the protease imaging sensor to the tumor cell, said tumor imaging agent comprising a pH low insertion peptide that is attached to a second detectable marker, wherein the tumor imaging agent is linked to the scaffold and does not include a cell penetrating domain, and wherein the pH low insertion peptide comprises an amino acid sequence selected from the group consisting of SEQ ID NOs: 33-36.

2. The protease imaging sensor of claim 1, wherein each enzyme-specific substrate comprises a cancer substrate.

3. The protease imaging sensor of claim 2, wherein the cancer substrate is cleaved by an enzyme associated with colorectal cancer metastasis.

4. The protease imaging sensor of claim 1, wherein the second detectable marker comprises a radiolabel and is detectable by positron emission tomography or computerized tomography.

5. The protease imaging sensor of claim 4, wherein the radiolabel is selected from the group consisting of $^{64}$Cu, Gd(DOTA), $^{201}$Tl, $^{99m}$Tc, $^{18}$F-2-deoxyfluoroglucose (FDG), (18)F-fluoride, gadodiamide, radioisotopes of Pb(II), $^{111}$In, and $^{89}$Zr.

6. The protease imaging sensor of claim 4, wherein the second detectable marker comprises a metal chelator selected from the group consisting of 1,4,7-Triazacyclononane-1,4,7-triacetic acid (NOTA), 1,4,7,10-tetraazacyclododecane-N,N',N'',N'''-tetraacetic acid (DOTA), Diethylenetriaminepentaacetic Anhydride (DTPA), 1,4,8,1-tetraazacyclotetradecane-1,4,8,11-tetraacetic acid (TETA), and deferoxamine.

7. The protease imaging sensor of claim 1, wherein the pH low insertion peptide comprises a D-amino acid, an azide side chain, and/or cyanine.

8. The protease imaging sensor of claim 1, wherein the ratio of the number of enzyme-specific substrates to the number of tumor imaging agent is 1:1.

9. The protease imaging sensor of claim 2, wherein the cancer substrate is cleaved by an enzyme associated with colorectal cancer (CRC).

10. The protease imaging sensor of claim 1, wherein the pH low insertion peptide comprises a D-amino acid.

11. The protease imaging sensor of claim 1, wherein the pH low insertion peptide comprises SEQ ID NO: 17.

12. The protease imaging sensor of claim 1, wherein lysines in the WKK sequence of the amino acid sequence are D-amino acids.

13. The protease imaging sensor of claim 1, wherein tryptophan in the WKK sequence of the amino acid sequence is a L-amino acid.

14. The protease imaging sensor of claim 1, wherein the WKK sequence of the amino acid sequence is located at the C-terminus of the pH low insertion peptide.

15. The protease imaging sensor of claim 1, wherein the tumor imaging peptide is N-terminally linked to the scaffold.

16. The protease imaging sensor of claim 1, wherein the pH low insertion peptide is N-terminally conjugated to the second detectable marker.

17. The protease imaging sensor of claim 1, wherein the first detectable marker comprises a peptide, a nucleic acid, a small molecule, a fluorophore, a carbohydrate, a particle, a radiolabel, a MRI-active compound, a ligand encoded reporter, or an isotope coded reporter molecule (iCORE).

18. The protease imaging sensor of claim 1, wherein the scaffold comprises a multi-arm polyethylene glycol molecule (multi-arm PEG).

19. The protease imaging sensor of claim 1, wherein the protease imaging sensor comprises multiple enzyme-specific substrates, multiple tumor imaging peptides, or a combination thereof.

* * * * *